United States Patent
Walker et al.

(10) Patent No.: US 11,691,976 B2
(45) Date of Patent: Jul. 4, 2023

(54) COELENTERAZINE ANALOGUES

(71) Applicant: PROMEGA CORPORATION, Madison, WI (US)

(72) Inventors: Joel R. Walker, San Luis Obispo, CA (US); Thomas A. Kirkland, Atascadero, CA (US); Wenhui Zhou, San Luis Obispo, CA (US); Mary P. Hall, Waunakee, WI (US); Harry Tetsuo Uyeda, Los Osos, CA (US)

(73) Assignee: Promega Corporation, Madison, WI (US)

( * ) Notice: Subject to any disclaimer, the term of this patent is extended or adjusted under 35 U.S.C. 154(b) by 334 days.

(21) Appl. No.: 16/548,214

(22) Filed: Aug. 22, 2019

(65) Prior Publication Data

US 2020/0062766 A1    Feb. 27, 2020

Related U.S. Application Data

(60) Provisional application No. 62/721,708, filed on Aug. 23, 2018.

(51) Int. Cl.
*C07D 487/04* (2006.01)
*A61K 49/00* (2006.01)
*G01N 21/76* (2006.01)

(52) U.S. Cl.
CPC ........ *C07D 487/04* (2013.01); *A61K 49/0021* (2013.01); *G01N 21/763* (2013.01)

(58) Field of Classification Search
CPC . A61K 49/0021; G01N 21/763; C07D 487/04
See application file for complete search history.

(56) References Cited

U.S. PATENT DOCUMENTS

| | | |
|---|---|---|
| 5,650,135 A | 7/1997 | Contag et al. |
| 10,024,862 B2 | 7/2018 | Hitko et al. |
| 10,067,149 B2 | 9/2018 | Hitko et al. |
| 2007/0015790 A1 | 1/2007 | Cali et al. |
| 2012/0117667 A1 | 5/2012 | Klaubert et al. |
| 2014/0194307 A1 | 7/2014 | Hitko et al. |
| 2014/0194325 A1 | 7/2014 | Hitko et al. |
| 2014/0304842 A1 | 10/2014 | Hitko |
| 2017/0233789 A1 | 8/2017 | Shakhmin et al. |
| 2018/0030059 A1 | 2/2018 | Hall et al. |
| 2018/0155350 A1* | 6/2018 | Hall ............. G01N 33/581 |
| 2019/0337939 A1 | 11/2019 | Binkowski et al. |
| 2019/0382365 A1 | 12/2019 | Walker et al. |

FOREIGN PATENT DOCUMENTS

| | | | |
|---|---|---|---|
| CN | 105 968 114 | 9/2016 | |
| EP | 3 395 803 | 10/2018 | |
| WO | 2006/130551 | 12/2006 | |
| WO | 2014/053605 | 4/2014 | |
| WO | 2014/159044 | 10/2014 | |
| WO | 2016/210294 | 12/2016 | |
| WO | WO-2018022865 A1 * | 2/2018 | ......... A61K 49/0021 |
| WO | 2018/125992 | 7/2018 | |

OTHER PUBLICATIONS

Shimomura et al. "Semi-synthetic aequorins with improved sensitivity to Ca2+ ions", Biochem. J. (1989) 261, 913-920 (Year: 1989).*
International Search Report and Written Opinion, Int'l Patent Application No. PCT/US2019/047688, dated Feb. 4, 2020, 23 pages.
Cosby et al. Custom Enzyme Substrates for Luciferase-based Assays, Cell Notes (2007) 18, pp. 9-11.
Contag, P., et al., Bioluminescent indicators in living mammals, Nature Medicine 4(2):245-247, 1998.
Contag, C., et al., Photonic Monitoring of Infectious Disease and Gene Regulation, OSA TOPS on Biomedical Optica Spectroscopy and Diagnostics 3:220-224, 1996.
Contag, C. H., Visualizing Gene Expression in Living Mammals Using a Bioluminescent Reporter, Photochemistry and Photobiology 66(4):523-531, 1997.
Contag, C. H. et al, Photonic detection of bacterial pathogens in living hosts, Molecular Microbiology 18(4):593-603, 1995.
Eloi P. Coutant et al.: "Gram-scale synthesis of luciferins derived from coelenterazine and original insights into their bioluminescence properties" Organic and Biomolecular Chemistry, vol. 17, No. 15, Jan. 1, 2019, pp. 3709-3713.
Ronan Gealageas et al: "Bioluminescent properties of obelin and aequorin with novel coelenterazine analogues" Analytical and Bioanalytical Chemistry, vol. 406, No. 11, Feb. 20, 2014, pp. 2695-2707.

* cited by examiner

*Primary Examiner* — James W Rogers
(74) *Attorney, Agent, or Firm* — Casimir Jones, S.C.; Anne M. Reynolds

(57) ABSTRACT

Described are coelenterazine analogues, methods for making the analogues, kits comprising the analogues, and methods of using the compounds for the detection of luminescence in luciferase-based assays.

17 Claims, 2 Drawing Sheets

COELENTERAZINE ANALOGUES

CROSS-REFERENCE TO RELATED APPLICATIONS

This application claims priority to U.S. Provisional Patent Application No. 62/721,708, filed on Aug. 23, 2018, the entire contents of which are fully incorporated herein by reference.

TECHNICAL FIELD

The present disclosure relates to coelenterazine analogues, methods for making coelenterazine analogues, and methods of using coelenterazine analogues in luciferase-based assays.

BACKGROUND

Bioluminescent assays are used extensively in the investigation of cellular physiology, especially processes associated with gene expression. In particular, luciferase reporter enzymes are quite valuable tools in this field, and, to date, there has been intense protein engineering to obtain small and environmentally insensitive luciferases that may be useful in bioluminescent assays. There exist a number of efficient luciferase reporters enabling whole-cell biosensor measurements, drug discovery through high-throughput screening, and in vivo imaging, which also permits the study of protein-protein interactions in living cells, apoptosis, and cell viability. Luciferases that use coelenterazine and coelenterazine analogues as substrates are among the most widely used systems due to their brightness and acceptance in whole cell applications.

SUMMARY OF THE INVENTION

Many known coelenterazine analogues have deficiencies, which limit their effectiveness as luciferase substrates and usefulness in luciferase-based assays. These deficiencies include cell toxicity, light sensitivity, thermodynamic instability, low aqueous solubility, and low cell permeability. Accordingly, there exists a need for coelenterazine analogues with improved properties and methods for synthesizing the analogues.

In one aspect, disclosed are compounds of formula (I),

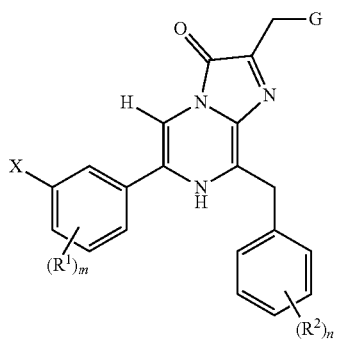

(I)

or a tautomer or a salt thereof, wherein:

X is $C_{1-10}$alkyl, halogen, CN, nitro, $C_{1-10}$haloalkyl, $C_{1-4}$haloalkylene-$OC_{1-4}$alkyl, $C_{2-10}$alkenyl, $C_{2-10}$alkynyl, —C(O)$OR^{x1}$, —CONR$^{x1}R^{x2}$, —OC(O)NR$^{x1}R^{x2}$, —NR$^{x3}$C(O)$OR^{x1}$, —$OR^{x1}$, —$C_{1-10}$alkylene-$OR^{x1}$, —OC(O)$R^{x1}$, —NR$^{x1}R^{x2}$, —$C_{1-10}$alkylene-NR$^{x1}R^{x2}$; —NR$^{x3}$C(O)$R^{x1}$, —NR$^{x3}$C(O)NR$^{x1}R^{x2}$, —$SO_2R^{x1}$, —$SO_2NR^{x1}R^{x2}$, —NR$^{x3}SO_2R^{x1}$, —$SO_2OR^{x1}$, —$OSO_2R^{x1}$, —$OSO_3R^{x1}$, —OP(O)(OH)$OR^{x1}$, —OSi($C_{1-10}$alkyl)$_3$, —$OR^{x0}$, —$OG^E$, or —NR$^{x1}G^E$;

m is 0, 1, 2, 3, or 4;

$R^1$, at each occurrence, is independently halogen, CN, nitro, $C_{1-10}$alkyl, $C_{1-10}$haloalkyl, —$OR^{A1}$, —NR$^{B1}R^{C1}$, —$OG^E$, or —NR$^{B1}G^E$;

wherein optionally two adjacent $R^1$ groups, or X and an adjacent $R^1$ group, together with the carbon atoms to which they are attached form a fused ring selected from a 5- to 7-membered cycloalkyl, a 5- to 7-membered cycloalkenyl, a phenyl, a 5- to 6-membered heteroaryl, or a 5- to 7-membered heterocyclyl, the optional fused ring being optionally substituted with 1-4 substituents independently selected from the group consisting of halogen, CN, nitro, $C_{1-10}$alkyl, $C_{1-10}$haloalkyl, —$OR^{A1}$, and —NR$^{B1}R^{C1}$;

$G^E$, at each occurrence, independently comprises an enzyme substrate, wherein biotransformation by an enzyme converts $G^E$ to H;

n is 0, 1, 2, 3, 4, or 5;

$R^2$, at each occurrence, is independently halogen, CN, nitro, $C_{1-10}$alkyl, $C_{1-10}$haloalkyl, —$OR^{A2}$, or —NR$^{B2}R^{C2}$; wherein two adjacent $R^2$ groups together with the carbon atoms to which they are attached optionally form a fused ring selected from a 5- to 7-membered cycloalkyl, a 5- to 7-membered cycloalkenyl, a phenyl, a 5- to 6-membered heteroaryl, or a 5- to 7-membered heterocyclyl, the optional fused ring being optionally substituted with 1-4 substituents independently selected from the group consisting of halogen, CN, nitro, $C_{1-10}$alkyl, $C_{1-10}$haloalkyl, —$OR^{A2}$, and —NR$^{B2}R^{C2}$;

$R^{A1}$ and $R^{A2}$, at each occurrence, are independently H, $C_{1-10}$alkyl, $C_{1-10}$haloalkyl, $C_{3-12}$cycloalkyl, —C(O)$C_{1-10}$alkyl, —C(O)$C_{3-12}$ cycloalkyl, or —C(O)$C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;

$R^{B1}$, $R^{B2}$, $R^{C1}$, and $R^{C2}$, at each occurrence, are independently H, $C_{1-10}$alkyl, $C_{1-10}$haloalkyl, $C_{3-12}$cycloalkyl, —C(O)$C_{1-10}$alkyl, —C(O)$C_{3-12}$ cycloalkyl, —C(O)$C_{1-3}$alkylene-$C_{3-12}$cycloalkyl, —$SO_2C_{1-10}$alkyl, —$SO_2C_{3-12}$cycloalkyl, or —$SO_2C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;

alternatively, $R^{B1}$ and $R^{C1}$ and/or $R^{B2}$ and $R^{C2}$, together with the nitrogen atom to which each attaches form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

G is furan-2-yl substituted with 1, 2, or 3 $R^D$ groups, a 6- to 12-membered aryl, or a 5- to 12-membered heteroaryl other than furan-2-yl, wherein the aryl and heteroaryl are optionally substituted with 1, 2, 3, 4, or 5 $R^E$ groups;

$R^D$ and $R^E$, at each occurrence, are independently halogen, $C_{1-10}$alkyl, $C_{1-10}$haloalkyl, or -L-$R^W$;

L is a bond, $C_{1-10}$alkylene, or —$OC_{1-10}$alkylene-;

$R^W$ is —CN, —$NO_2$, —$OR^{x4}$, —NR$^{x4}R^{x5}$, —C(O)$OR^{x4}$, —OC(O)$R^{x4}$, —NR$^{x6}$C(O)$R^{x2}$, —C(O)NR$^{x4}R^{x5}$, —NR$^{x6}$C(O)$OR^{x4}$, —OC(O)NR$^{x4}R^{x5}$, —$SO_2R^{x4}$, —$SO_2NR^{x4}R^{x5}$, —NR$^{x6}SO_2R^{x4}$, —$OSO_2R^{x4}$, —$SO_2OR^{x4}$, —$OSO_3R^{x4}$, —OP(O)(OH)$OR^{x4}$, or —NR$^{x6}$C(O)NR$^{x4}R^{x5}$;

$R^{x1}$, $R^{x2}$, $R^{x3}$, $R^{x4}$, $R^{x5}$, and $R^{x6}$, at each occurrence, are independently H, $C_{1-10}$alkyl, $C_{1-10}$haloalkyl, $C_{3-12}$cycloalkyl, or —$C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;

alternatively, $R^{x1}$ and $R^{x2}$ and/or $R^{x4}$ and $R^{x5}$, together with the nitrogen atom to which each attaches form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{x0}$ is a sugar moiety; and provided that the compound is not
8-benzyl-2-(4-hydroxybenzyl)-6-(3-hydroxyphenyl)imidazo[1,2-a]pyrazin-3(7H)-one;
6-(4-((8-benzyl-6-(3-hydroxyphenyl)-3-oxo-3,7-dihydroimidazo[1,2-a]pyrazin-2-yl)methyl)-2-chlorophenoxy) hexane-1-sulfonic acid; or
6-(4-((8-benzyl-6-(3-((tert-butyldimethylsilyl)oxy)phenyl)-3-oxo-3,7-dihydroimidazo[1,2-a]pyrazin-2-yl)methyl)-2-chlorophenoxy)hexane-1-sulfonic acid.

In another aspect, disclosed are compounds of formula (II),

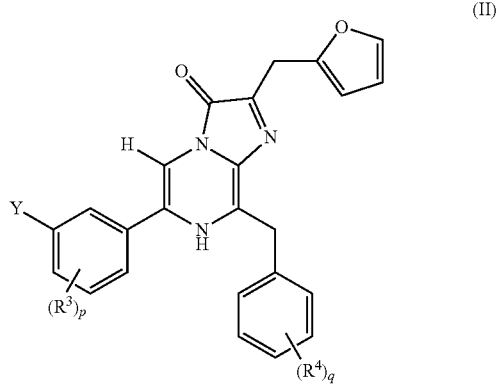

(II)

or a tautomer or a salt thereof, wherein:

Y is $C_{1-10}$alkyl, halogen, CN, nitro, $C_{1-10}$haloalkyl, $C_{1-4}$haloalkylene-$OC_{1-4}$alkyl, $C_{2-10}$alkenyl, $C_{2-10}$alkynyl, —C(O)$OR^{y1}$, —CON$R^{y1}R^{y2}$, —OC(O)N$R^{y1}R^{y2}$, —$NR^{y3}$C(O)$OR^{y1}$, —$OR^{y1}$, —$C_{1-10}$alkylene-$OR^{y1}$, —OC(O)$R^{y1}$, —$NR^{y1}R^{y2}$, —$C_{1-10}$alkylene-$NR^{y1}R^{y2}$; —$NR^{y3}$C(O)$R^{y1}$, —$NR^{y3}$C(O)$NR^{y1}R^{y2}$, —$SO_2R^{y1}$, —$SO_2NR^{y1}R^{y2}$, —$NR^{y3}SO_2R^{y1}$, —$SO_2OR^{y1}$, —$OSO_2R^{y1}$, —$OSO_3R^{y1}$, —OP(O)(OH)$OR^{y1}$, —OSi($C_{1-10}$alkyl)$_3$, —$OR^{y0}$, —$OG^E$, or —$NR^{y1}G^E$;

p is 0, 1, 2, 3, or 4;

q is 0, 1, 2, 3, 4, or 5;

$R^3$, at each occurrence, is independently halogen, CN, nitro, $C_{1-10}$alkyl, $C_{1-10}$haloalkyl, —$OR^{43}$, —$NR^{B3}R^{C3}$, —$OG^E$, or —$NR^{B3}G^E$;

wherein optionally two adjacent $R^3$ groups, or Y and an adjacent $R^3$ group, together with the carbon atoms to which they are attached form a fused ring selected from a 5- to 7-membered cycloalkyl, a 5- to 7-membered cycloalkenyl, a phenyl, a 5- to 6-membered heteroaryl, or a 5- to 7-membered heterocyclyl, the optional fused ring being optionally substituted with 1-4 substituents independently selected from the group consisting of halogen, CN, nitro, $C_{1-10}$alkyl, $C_{1-10}$haloalkyl, —$OR^{43}$, and —$NR^{B3}R^{C3}$;

$G^E$, at each occurrence, independently comprises an enzyme substrate, wherein biotransformation by an enzyme converts $G^E$ to H;

$R^4$, at each occurrence, is independently halogen, CN, nitro, $C_{1-10}$alkyl, $C_{1-10}$haloalkyl, —$OR^{44}$, or —$NR^{B4}R^{C4}$;

wherein two adjacent $R^4$ groups together with the carbon atoms to which they are attached optionally form a fused ring selected from a 5- to 7-membered cycloalkyl, a 5- to 7-membered cycloalkenyl, a phenyl, a 5- to 6-membered heteroaryl, or a 5- to 7-membered heterocyclyl, the optional fused ring being optionally substituted with 1-4 substituents independently selected from the group consisting of halogen, CN, nitro, $C_{1-10}$alkyl, $C_{1-10}$haloalkyl, —$OR^{44}$, and —$NR^{B4}R^{C4}$;

$R^{43}$ and $R^{44}$, at each occurrence, are independently H, $C_{1-10}$alkyl, $C_{1-10}$haloalkyl, $C_{3-12}$cycloalkyl, —C(O)$C_{1-10}$alkyl, —C(O)$C_{3-12}$cycloalkyl, or —C(O)$C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;

$R^{B3}$, $R^{B4}$, $R^{C3}$, and $R^{C4}$, at each occurrence, are independently H, $C_{1-10}$alkyl, $C_{1-10}$haloalkyl, $C_{3-12}$cycloalkyl, —C(O)$C_{1-10}$alkyl, —C(O)$C_{3-12}$cycloalkyl, —C(O)$C_{1-3}$alkylene-$C_{3-12}$cycloalkyl, —$SO_2C_{1-10}$alkyl, —$SO_2C_{3-12}$cycloalkyl, or —$SO_2C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;

alternatively, $R^{B3}$ and $R^{C3}$ and/or $R^{B4}$ and $R^{C4}$, together with the nitrogen atom to which each attaches form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;

$R^{y1}$, $R^{y2}$, and $R^{y3}$, at each occurrence, are independently H, $C_{1-10}$alkyl, $C_{1-10}$haloalkyl, $C_{3-12}$cycloalkyl, or $C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;

alternatively, $R^{y1}$ and $R^{y2}$ together with the nitrogen atom to which each attaches form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl; and $R^{y0}$ is a sugar moiety provided that the compound is not
8-benzyl-2-(furan-2-ylmethyl)-6-(3-methoxyphenyl)imidazo[1,2-a]pyrazin-3(7H)-one;
8-benzyl-2-(furan-2-ylmethyl)-6-(3-hydroxyphenyl)imidazo[1,2-a]pyrazin-3(7H)-one;
6-(3-aminophenyl)-8-benzyl-2-(furan-2-ylmethyl)imidazo[1,2-a]pyrazin-3(7H)-one;
8-benzyl-2-(furan-2-ylmethyl)-6-(naphthalen-1-yl)imidazo[1,2-a]pyrazin-3(7H)-one;
8-benzyl-2-(furan-2-ylmethyl)-6-(naphthalen-2-yl)imidazo[1,2-a]pyrazin-3(7H)-one;
6-(anthracen-9-yl)-8-benzyl-2-(furan-2-ylmethyl)imidazo[1,2-a]pyrazin-3(7H)-one;
8-benzyl-2-(furan-2-ylmethyl)-6-(phenanthren-9-yl)imidazo[1,2-a]pyrazin-3(7H)-one;
8-benzyl-2-(furan-2-ylmethyl)-6-(quinolin-6-yl)imidazo[1,2-a]pyrazin-3(7H)-one;
tert-butyl 3-(8-benzyl-2-(furan-2-ylmethyl)-3-oxo-3,7-dihydroimidazo[1,2-a]pyrazin-6-yl)benzoate; or 3-(8-benzyl-2-(furan-2-ylmethyl)-3-oxo-3,7-dihydroimidazo[1,2-a]pyrazin-6-yl)benzoic acid.

Also disclosed are methods of making the compounds, kits comprising the compounds, and methods of using the compounds as luciferase substrates in luciferase-based assays.

DETAILED DESCRIPTION

Figure 1:
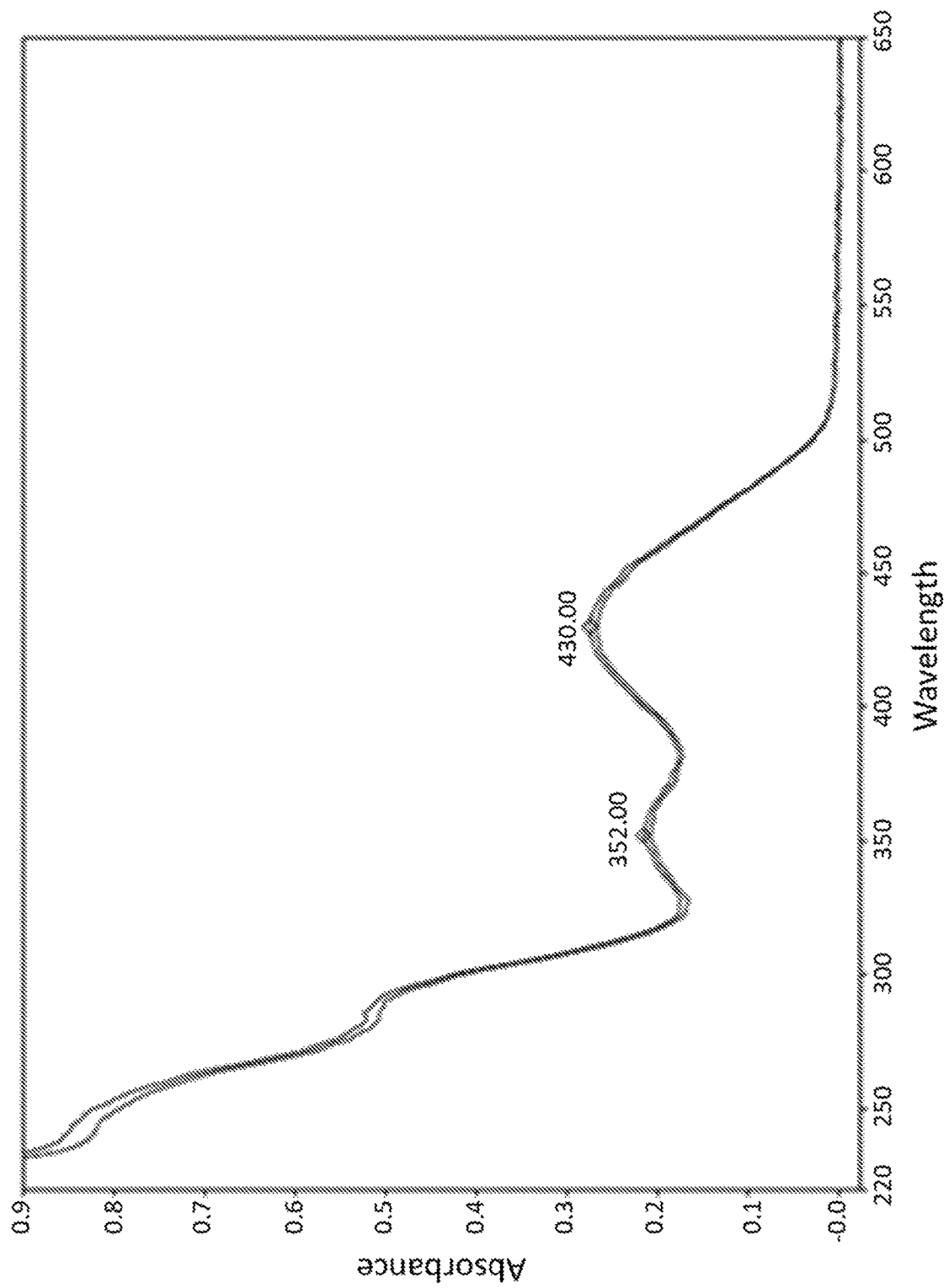
FIG. 1 shows UV absorbance spectra for 8.7 mM JW-1040 in ethanol/propylene glycol/hydroxypropyl-β-cyclodextrin/PEG 400/water (10:10:10:35:35) before (supernatant) and after filtration (filtrate).

Disclosed herein are coelenterazine analogues. The coelenterazine analogues can be compounds of formula (I) or formula (II) and can be useful substrates for proteins that utilize coelenterazine ("coelenterazine-utilizing enzymes") to produce luminescence, including, but not limited to, luciferases and photoproteins found in various marine organisms such as cnidarians (e.g., *Renilla* luciferase), jellyfish (e.g., aequorin from the *Aequorea* jellyfish) and decapods luciferases (e.g., luciferase complex of *Oplophorus gracilirosIns*).

In some embodiments, compounds of formula (I) and formula (II) display improved aqueous solubility compared to furimazine. In some embodiments, compounds of formula (I) and (II) display improved bioluminescence signal kinetics compared to coelenterazine compounds with the analogous substitution in the para position of the 6-phenyl group. Thus, the compounds of formula (I) and (II) may be useful for in vivo luminescent imaging applications as well as in other applications that utilize bioluminescence.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of," and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain saturated hydrocarbon containing from 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkynyl" as used herein, means a hydrocarbon chain containing at least one carbon-carbon triple bond.

The term "alkylene," as used herein, refers to a divalent group derived from a straight or branched saturated chain hydrocarbon, for example, of 1 to 6 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cycloalkyl," as used herein, refers to a carbocyclic ring system containing zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl," as used herein, means a non-aromatic monocyclic or multicyclic all-carbon ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a monocyclic aromatic, saturated, or partially saturated carbocyclic ring, a monocyclic heteroaryl, or a monocyclic heterocycle. The bicyclic heteroaryl is attached to the parent molecular moiety at an aromatic ring atom. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-6]pyridin-2-yl, thiazolo[5,4-<7]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, a monocyclic heterocycle fused to a monocyclic heteroaryl, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a non-aromatic ring atom (e.g., 2-oxaspiro[3.3]heptan-6-yl, indolin-1-yl, hexahydrocyclopenta[b]pyrrol-1 (2H)-yl). Representative examples of bicyclic heterocycles include, but are not limited to, benzopyranyl, benzothiopyrany 1, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1,13,7]decane). The monocyclic, bicyclic, and tricyclic heterocycles are connected to the parent molecular moiety at a non-aromatic ring atom.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

An "animal" as used herein refers to any vertebrate, including, but is not limited to, mammals, amphibians, birds, fish, insects, reptiles, etc. Mammals can include, but are not limited, to humans, non-human primates (e.g., gorilla, monkey, baboon, and chimpanzee, etc.), dogs, cats, goats, horses, pigs, cattle, sheep, and the like, and laboratory animals (e.g., rats, guinea pigs, mice, gerbils, hamsters, and the like. In some embodiments, the animal can be a human or a non-human. Suitable animals include both males and females and animals of any age, including embryonic (e.g., in utero or in ovo), infant, juvenile, adolescent, adult and geriatric animals.

"Fusion protein" and "fusion polypeptide" as used herein refers to a fusion comprising at least one bioluminescent protein in combination with a heterologous protein of interest, such as a fluorescent protein, as part of a single continuous chain of amino acids, which chain does not occur in nature.

"Operably linked" as used herein means that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

"Transgene" as used herein refers to a gene or genetic material containing a gene sequence that has been isolated and/or manipulated from one organism and is introduced into a different organism. The transgene may contain a transgenic sequence or a native or wild-type DNA sequence. This non-native segment of DNA can retain the ability to produce RNA or protein in the transgenic organism. For example, the transgene can encode a fusion protein, such as a fusion protein comprising a luciferase. A transgenic sequence can be partly or entirely species-heterologous, i.e., the transgenic sequence, or a portion thereof, can be from a species which is different from the cell into which it is introduced.

A "transgenic animal" refers to a genetically engineered animal or offspring of genetically engineered animals. A transgenic animal usually contains genetic material from at least one unrelated organism, such as from a virus, plant, or other animal.

The terms "transformation," "transfection," and "transduction" as used interchangeably herein refer to the introduction of a heterologous nucleic acid molecule, such as genetic material, into a cell. Such introduction into a cell can be stable or transient. Thus, in some embodiments, a host cell or host organism is stably transformed with a heterologous nucleic acid molecule, such as genetic material. In other embodiments, a host cell or host organism is transiently transformed with a heterologous nucleic acid molecule, such as genetic material. "Transient transformation" in the context of a polynucleotide means that a polynucleotide is introduced into the cell and does not integrate into the genome of the cell. By "stably introducing" or "stably introduced" in the context of a polynucleotide introduced into a cell is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein also includes the nuclear, the plasmid and the plastid genome, and therefore includes integration of the nucleic acid construct into, for example, the chloroplast or mitochondrial genome. Stable transformation as used herein can also refer to a transgene that is maintained extrachromasomally, for example, as a minichromosome or a plasmid. In some embodiments, the nucleotide sequences, constructs, expression cassettes can be expressed transiently and/or they can be stably incorporated into the genome of the host organism.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. COMPOUNDS

A first aspect of the invention provides compounds of formula (I), wherein $R^1$, $R^2$, X, G, m, and n are as defined herein. The embodiments of formula (I) provided herein include any combinations of the variables $R^1$, $R^2$, X, G, m, and n, as these variables are described herein, including with sub-variables such as $R^{x1}$, $R^{x2}$, $R^D$, etc.

In some embodiments, G is furan-2-yl substituted with 1, 2, or 3 $R^D$ groups, wherein $R^D$ is as defined herein. In some embodiments, the furan-2-yl is substituted with a single $R^D$ group

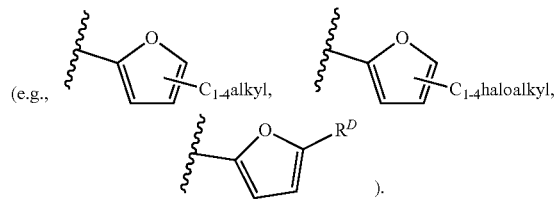

In further embodiments, $R^D$ is $C_{1-4}$alkyl (e.g., $CH_3$) or $C_{1-4}$haloalkyl (e.g., $CF_3$).

In some embodiments, G is a 6- to 12-membered aryl, optionally substituted with 1, 2, 3, 4, or 5 $R^E$ groups, wherein $R^E$ is as defined herein. In further embodiments, the 6- to 12-membered aryl is phenyl. In other embodiments, the 6- to 12-membered aryl is phenyl fused to a 5- to 7-membered heterocyclic ring containing 1-2 oxygen atoms (e.g., benzodioxole). In further embodiments, the aryl (e.g., phenyl) is optionally substituted with 1-3 $R^E$, such as halogen, $C_{1-4}$alkyl, —$OC_{1-4}$alkyl, and —$C_{1-10}$alkylene-$OC_{1-4}$alkyl

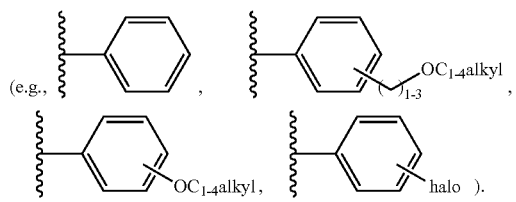

In further embodiments, the phenyl is optionally substituted with 1-3 $R^E$ groups independently selected from the group consisting of halogen, —$OR^{x4}$, $C_{1-10}$alkylene-$OR^{x4}$, and —$OC_{1-10}$alkylene-$SO_2OR^{x4}$ (e.g., —$OC_6$alkylene-$SO_3H$).

In other embodiments, G is a 5- to 12-membered heteroaryl other than furan-2-yl, optionally substituted with 1, 2, 3, 4, or 5 $R^E$ groups. In further embodiments, the heteroaryl is thienyl, imidazolyl, pyridinyl, or thiazolyl, for example,

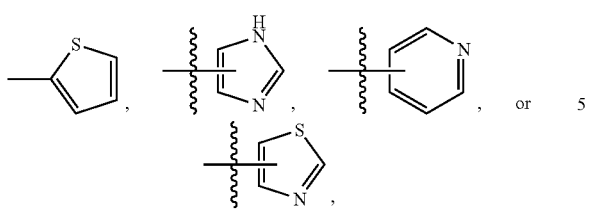

each optionally substituted with 1, 2, or 3 $R^E$ groups.

In further embodiments, G is selected from the group consisting of

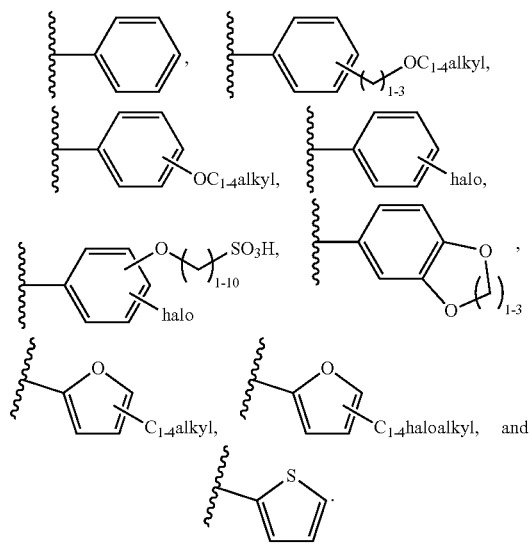

In some embodiments, X is $OR^{x1}$ or $NR^{x1}R^{x2}$, wherein $R^{x1}$ and $R^{x2}$ are as defined herein. In further embodiments, X is $OR^{x1}$. In other further embodiments, X is $NR^{x1}R^{x2}$. In these embodiments, are still further embodiments, wherein $R^{x1}$ and $R^{x2}$ are hydrogen. In other embodiments, X is $-OSi(C_{1-10}alkyl)_3$ (e.g., $-OSi(t-Bu)(Me)_2$.

In some embodiments, $R^1$, at each occurrence, is halogen, CN, nitro, $C_{1-10}$alkyl, $C_{1-10}$haloalkyl, $-OR^{A1}$, or $-NR^{B1}R^{C1}$, wherein $R^{A1}$, $R^{B1}$, and $R^{C1}$ are as defined herein. In further embodiments, $R^1$ is halogen, CN, nitro, $C_{1-4}$alkyl (e.g., methyl, ethyl), $C_{1-4}$haloalkyl (e.g., $CF_3$), $-OR^{A1}$, or $-NR^{B1}R^{C1}$, wherein $R^{A1}$, $R^{B1}$, and $R^{C1}$ are independently, at each occurrence, H, $C_{1-4}$alkyl (e.g., methyl, ethyl), $C_{1-4}$haloalkyl (e.g., $CF_3$), or $C_{3-6}$cycloalkyl (e.g., cyclopropyl).

In some embodiments, $R^2$, at each occurrence, is independently halogen, CN, nitro, $C_{1-10}$alkyl, $C_{1-10}$haloalkyl, $-OR^{A2}$, or $-NR^{B2}R^{C2}$, wherein $R^{A2}$, $R^{B2}$, and $R^{C2}$ are as defined herein. In further embodiments, $R^2$ is halogen, CN, nitro, $C_{1-4}$alkyl (e.g., methyl, ethyl), $C_{1-4}$haloalkyl (e.g., $CF_3$), $-OR^{A2}$, or $-NR^{B2}R^{C2}$, wherein $R^{A2}$, $R^{B2}$, and $R^{C2}$ are independently, at each occurrence, H, $C_{1-4}$alkyl (e.g., methyl, ethyl), $C_{1-4}$haloalkyl (e.g., $CF_3$), or $C_{3-6}$cycloalkyl (e.g., cyclopropyl).

In the embodiments of formula (I) described herein are embodiments where m is 0, and $R^2$, X, G, and n are as defined herein. In the embodiments of formula (I) described herein are embodiments where n is 0, and $R^1$, X, G, and m are as defined herein. For example, in some embodiments of formula (I), m is 0 and n is 0, and X and G are as defined herein.

In an exemplary combination, m is 0 and n is 0, X is OH or $NH_2$, and G is as defined herein. In a further exemplary combination G is furan-2-yl is substituted with a single $R^D$ group;

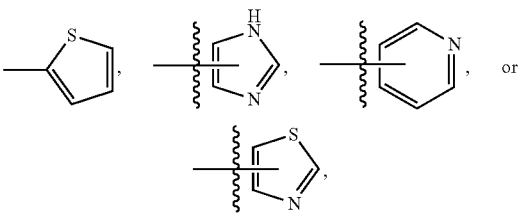

each optionally substituted with 1-3 $R^E$ groups; or aryl optionally substituted with 1-3 $R^E$ groups, wherein the aryl is phenyl or phenyl fused to a 5- to 7-membered heterocyclic ring containing 1-2 oxygen atoms (e.g., benzodioxole). The number and identity of $R^D$ and $R^E$ substituents are as described elsewhere herein.

In the embodiments of formula (I), described herein are embodiments where m is 1, $R^1$ is halogen, and $R^2$, X, G, and n are as defined herein. For example, in some embodiments of formula (I), m is 1 and n is 0, and X and G are as defined herein. In exemplary embodiments, m is 1, $R^1$ is fluorine, n is 0, X is OH or $NH_2$, and G is as defined herein.

Representative compounds of formula (I) include

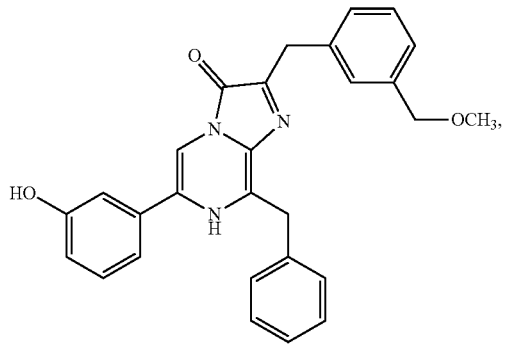

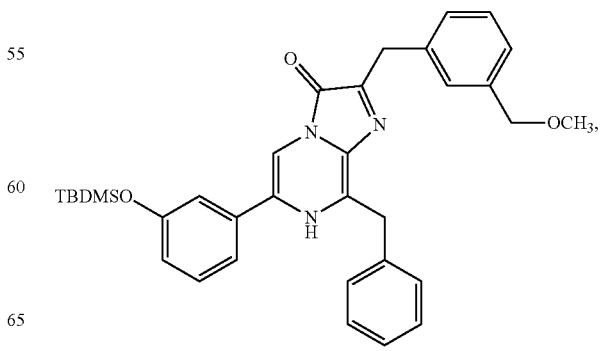

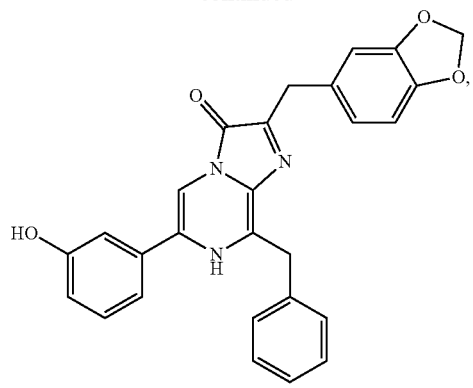
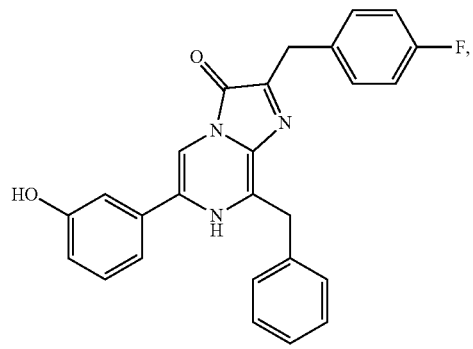
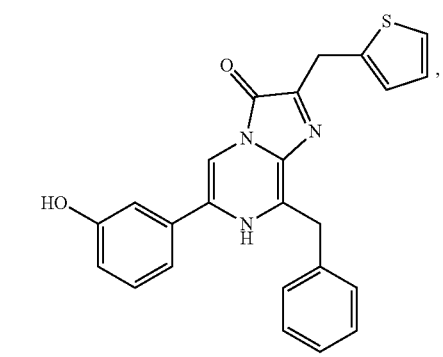
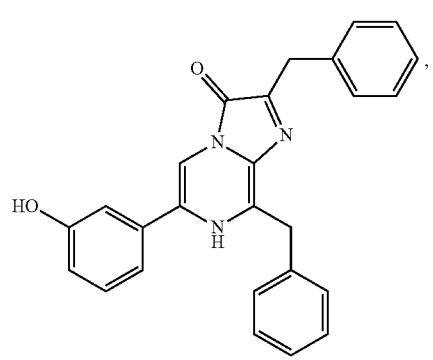
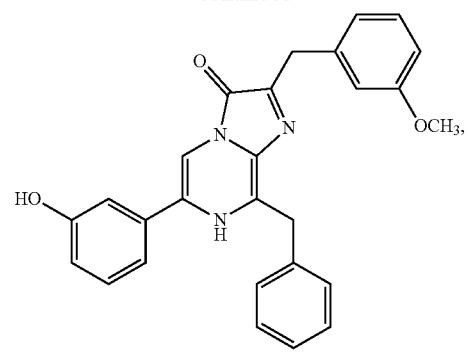
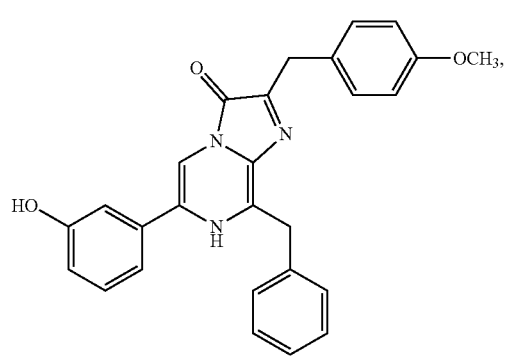
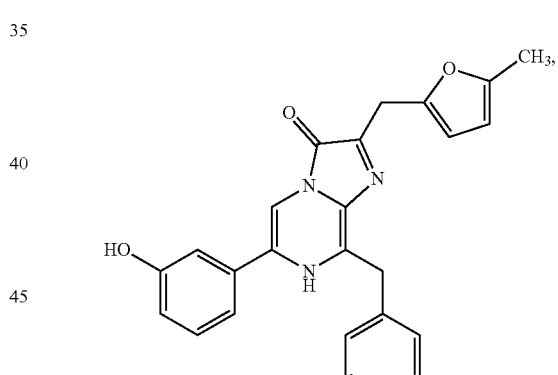
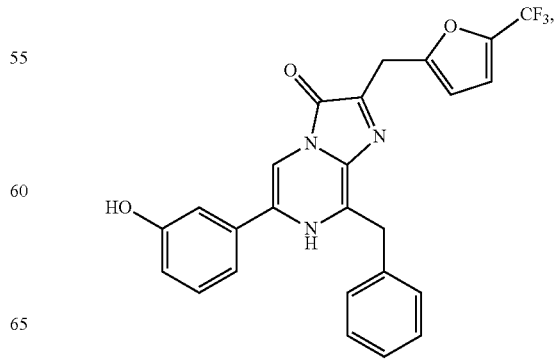

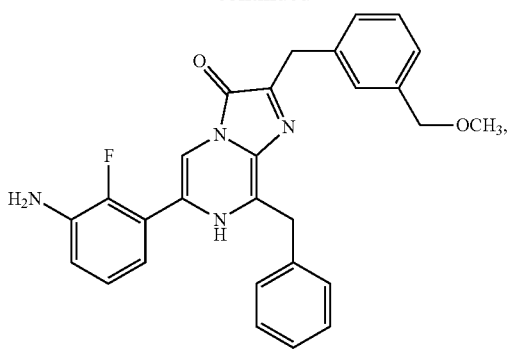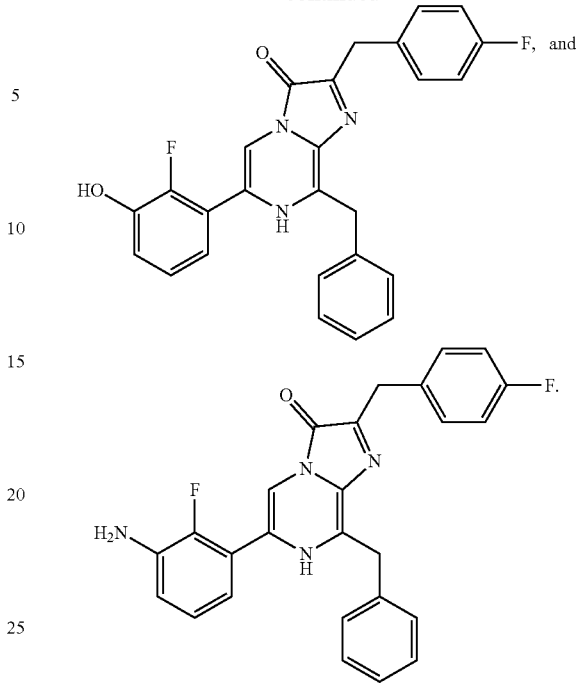

Another aspect of the invention provides compounds of formula (II), wherein $R^3$, $R^4$, Y, p, and q are as defined herein. The embodiments of formula (II) provided herein include any combinations of the variables $R^3$, $R^4$, Y, p, and q, as these variables are described herein, including with sub-variables such as $R^{y1}$, $R^{y2}$, $R^{A3}$, etc.

In some embodiments, optionally two adjacent $R^3$ groups, or Y and an adjacent $R^3$ group, together with the carbon atoms to which they are attached form a fused ring selected from a 5- to 7-membered cycloalkyl, a 5- to 7-membered cycloalkenyl, or a 5- to 7-membered heterocyclyl, the optional fused ring being optionally substituted with 1-4 substituents independently selected from the group consisting of halogen, CN, nitro, $C_{1-10}$alkyl, $C_{1-10}$haloalkyl, —$OR^{A3}$, and —$NR^{B3}R^{C3}$.

In some embodiments, p+q is 0, 1, 2, 3, 4, 5, 6, 7, 8, or 9. In some embodiments, p+q is 1, 2, 3, 4, 5, 6, 7, 8, or 9. In some embodiments, p is 1, 2, 3, or 4. In some embodiments, q is 1, 2, 3, 4, or 5. In some embodiments, p is 0. In some embodiments, q is 0. In some embodiments, p+q is 0, 1, or 2. In some embodiments, p+q is 1 or 2. In some embodiments, p+q is 1. In some embodiments, p+q is 2. In some embodiments, p+q is 3.

In some embodiments, Y is nitro, $OR^{y1}$, or $NR^{y1}R^{y2}$, wherein $R^{y1}$ and $R^{y2}$ are as defined herein. In some embodiments, Y is $OR^{y1}$ or $NR^{y1}R^{y2}$, wherein $R^{y1}$ and $R^{y2}$ are as defined herein. In further embodiments, Y is nitro. In further embodiments, Y is $OR^{y1}$. In other further embodiments, Y is $NR^{y1}R^{y2}$. In these embodiments, are still further embodiments, wherein $R^{y1}$ and $R^{y2}$ are hydrogen.

In some embodiments, $R^3$, at each occurrence, is halogen, CN, nitro, $C_{1-10}$alkyl, $C_{1-10}$haloalkyl, —$OR^{A3}$, or —$NR^{B3}R^{C3}$, wherein $R^{A3}$, $R^{B3}$, and $R^{C3}$ are as defined herein. In further embodiments, $R^3$ is halogen, CN, nitro, $C_{1-4}$alkyl (e.g., methyl, ethyl), $C_{1-4}$haloalkyl (e.g., $CF_3$), —$OR^{A3}$, or —$NR^{B3}R^{C3}$, wherein $R^{A3}$, $R^{B3}$, and $R^{C3}$ are independently, at each occurrence, H, $C_{1-4}$alkyl (e.g., methyl, ethyl), $C_{1-4}$haloalkyl (e.g., $CF_3$), or $C_{3-6}$cycloalkyl (e.g., cyclopropyl). In some embodiments, p is 1 and R³ is halogen or C₁₋₄alkyl (e.g., methyl). In some embodiments, p is 1 and R³ is halogen. In exemplary embodiments, p is 1 and R³ is fluorine or chlorine. In other exemplary embodiments, p is 1 and R³ is fluorine. In other exemplary embodiments, p is 1 and R³ is chlorine. In further exemplary embodiments, p is 1 and R³ is C₁₋₄alkyl. In other exemplary embodiments, p is 1 and R³ is methyl.

In some embodiments, R⁴, at each occurrence, is independently halogen, CN, nitro, C₁₋₁₀alkyl, C₁₋₁₀haloalkyl, —OR^A4, or —NR^B4R^C4, wherein R^A4, R^B4, and R^C4 are as defined herein. In further embodiments, R⁴ is halogen, CN, nitro, C₁₋₄alkyl (e.g., methyl, ethyl), C₁₋₄haloalkyl (e.g., CF₃), —OR^A4, or —NR^B4R^C4, wherein R^A4, R^B4, and R^C4 are independently, at each occurrence, H, C₁₋₄alkyl (e.g., methyl, ethyl), C₁₋₄haloalkyl (e.g., CF₃), or C₃₋₆cycloalkyl (e.g., cyclopropyl). In some embodiments, q is 1 or 2 and each R⁴ is independently halogen or C₁₋₄alkyl. In some embodiments, q is 1 and R⁴ is C₁₋₄alkyl.

In some embodiments, R⁴, at each occurrence, is halogen. In some embodiments, R⁴ is fluorine. In exemplary embodiments, q is 1 or 2 and R⁴ is fluorine. In some embodiments, q is 1 and R⁴ is fluorine. In other embodiments, q is 2 and each R⁴ is fluorine.

In the embodiments of formula (II) described herein are embodiments where p is 1, 2, 3, or 4, and R³, R⁴, Y, and q are as defined herein. In further embodiments, p is 1 or 2 and R³, R⁴, Y, and q are as defined herein. In still further embodiments, p is 1 and R³, R⁴, Y, and q are as defined herein.

In the embodiments of formula (II) described herein are embodiments where q is 0, 1, 2, 3, 4, or 5, and R³, R⁴, Y, and p are as defined herein. In the embodiments of formula (II) described herein are embodiments where q is 1, 2, 3, 4, or 5, and R³, R⁴, Y, and p are as defined herein. In further embodiments, q is 1 or 2 and R³, R⁴, Y, and p are as defined herein. In still further embodiments, q is 0 and R³, Y, and p are as defined herein. In still further embodiments, q is 1 and R³, R⁴, Y, and p are as defined herein.

In some embodiments of formula (II), p is 1, q is 1, and R³, R⁴, and Y are as defined herein. In some embodiments of formula (II), p is 1, q is 2, and R³, R⁴, and Y are as defined herein. In some embodiments of formula (II), p is 1, q is 0, and R³, R⁴, and Y are as defined herein.

In an exemplary combination, p is 0 or 1 and q is 0 or 1, Y is nitro, OH, or NH₂, R³, and R⁴ are independently halogen, CN, nitro, C₁₋₄alkyl (e.g., methyl, ethyl), C₁₋₄haloalkyl (e.g., CF₃), —OR^A4, or —NR^B4R^C4, wherein R^A4, R^B4, and R^C4 are independently, at each occurrence, H, C₁₋₄alkyl (e.g., methyl, ethyl), C₁₋₄haloalkyl (e.g., CF₃), or C₃₋₆cycloalkyl (e.g., cyclopropyl).

In an exemplary combination, p is 0 or 1 and q is 1, Y is OH or NH₂, R³, and R⁴ are independently halogen, CN, nitro, C₁₋₄alkyl (e.g., methyl, ethyl), C₁₋₄haloalkyl (e.g., CF₃), —OR^A4, or —NR^B4R^C4, wherein R^A4, R^B4, and R^C4 are independently, at each occurrence, H, C₁₋₄alkyl (e.g., methyl, ethyl), C₁₋₄haloalkyl (e.g., CF₃), or C₃₋₆cycloalkyl (e.g., cyclopropyl).

In an exemplary combination, p is 1 and q is 1 or 2, Y is OH or NH₂, and R³ and R⁴ are halogen.

Representative compounds of formula (II) include

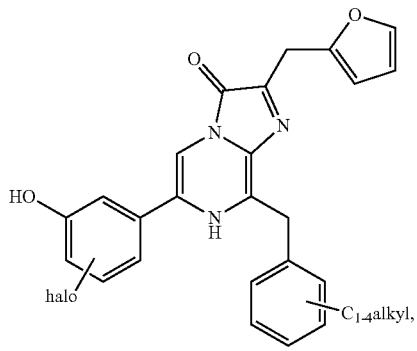

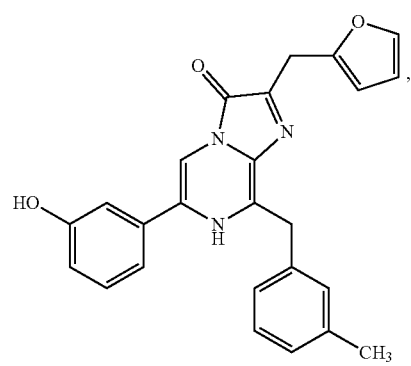

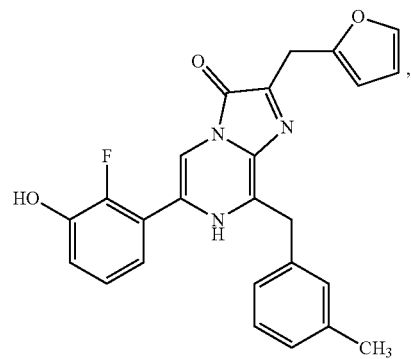

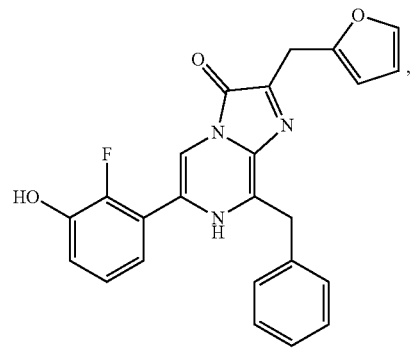

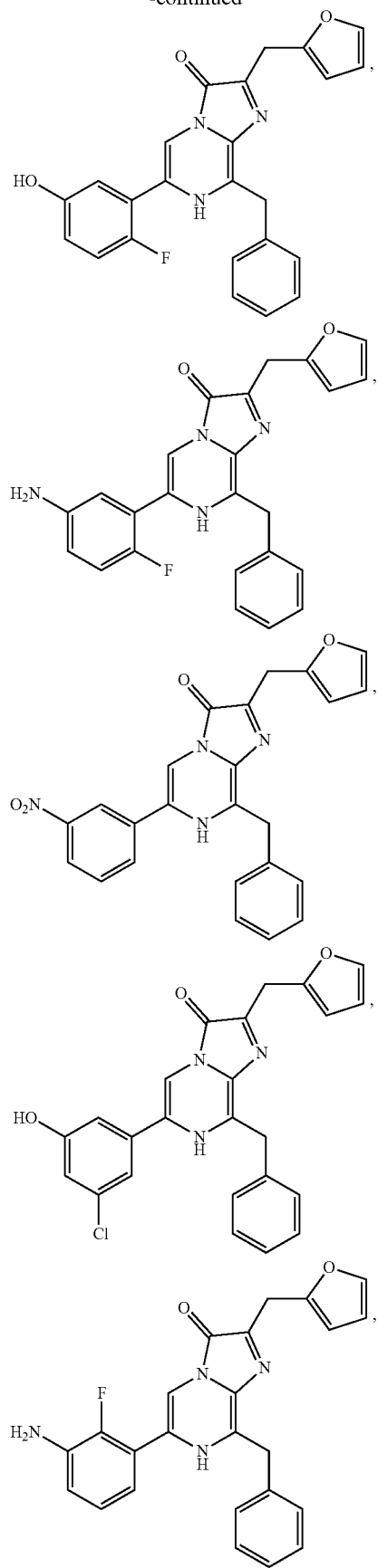
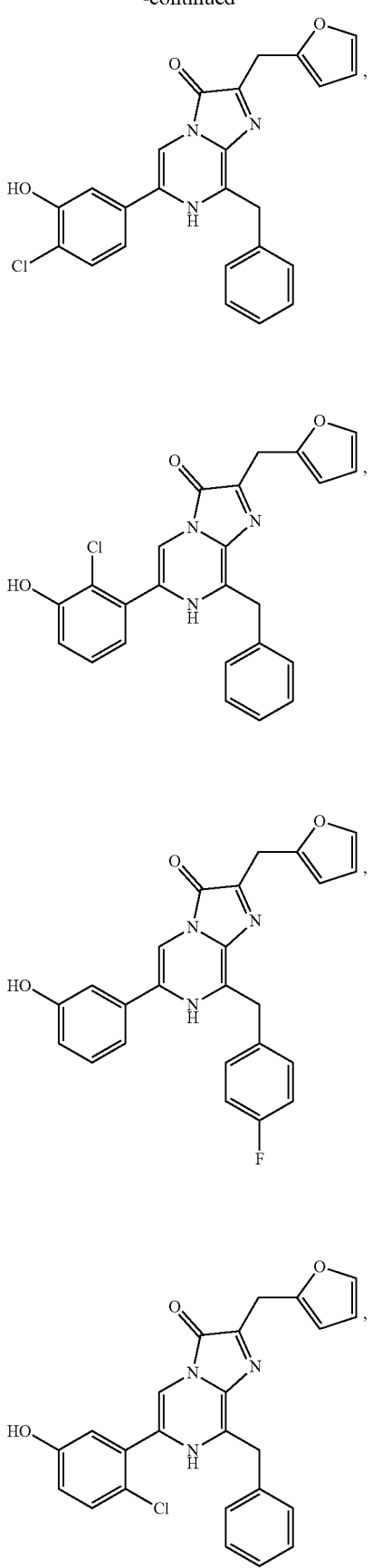

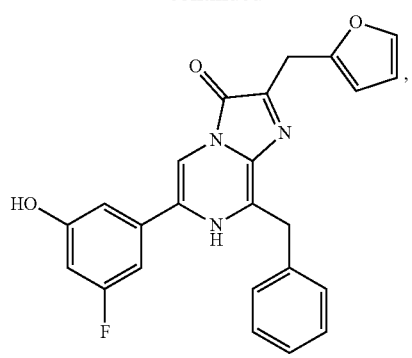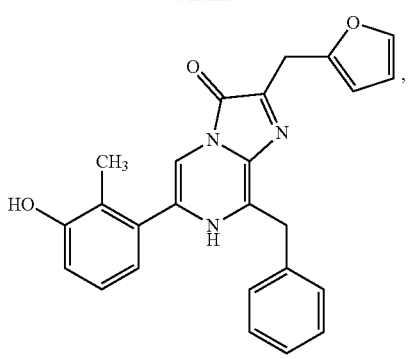

-continued

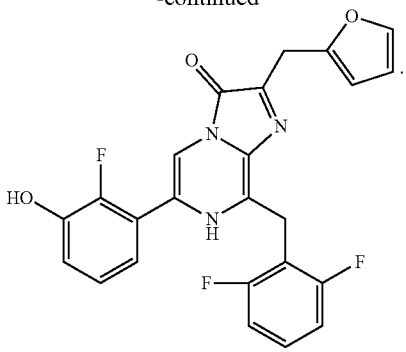

Scheme 1

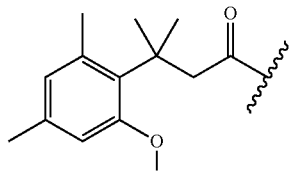

Trimethyl lock

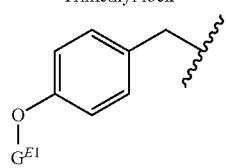

Quinone methide

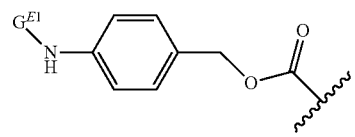

Para-amino benzyloxycarbonyl

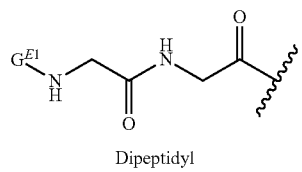

Dipeptidyl

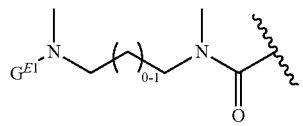

Alkylenediaminocarbonyl

In other embodiments, the compound of formula (I) or (II) may be a pro-substrate for a luciferase, i.e., a compound that does not support luminescence directly when combined with a luciferase, but can be converted into a luciferase substrate by biotransformation, e.g., with a second enzyme. Pro-substrates include, for example, a compound of formula (I) or (II) substituted with —$OG^E$, —$NR^{x1}G^E$, —$NR^{y1}G^E$, —$NR^{B1}G^E$, or —$NR^{B3}G^E$.

$G^E$ comprises an enzyme substrate, wherein biotransformation of the enzyme substrate by an enzyme converts $G^E$ to H. In some embodiments, $G^E$ is $G^{E1}$-$L^1$-; $G^{E1}$ is the enzyme substrate and $L^1$ is a linker connecting $G^{E1}$ to the remainder of the compound of formula (I) or (II) (i.e., the parent molecular moiety).

In some embodiments, $L^1$ is a bond or a divalent group composed of an arrangement of atoms stable under neutral ambient conditions, the atoms being selected from carbon, hydrogen, nitrogen, oxygen, sulfur, phosphorus, and silicon. The divalent group may include single (e.g., $CH_2$—$CH_2$, $CH_2$—O), double (e.g., C=O), or triple bonds (e.g., C≡C), and may contain or include ring structures (e.g., a cycloalkyl). In some embodiments, the divalent group is an arrangement of one or more of —$C_{1-10}$alkylene-, —$C_{2-10}$alkylene-O—, $C_{3-8}$cycloalkylene, —C(O)—, —O—, —S—, —S(O)—, —S(O)$_2$—, —NH—, —N($C_{1-4}$alkyl)-, —N(CO$C_{1-4}$alkyl)-, an amino acid moiety, a protected amino acid moiety, and phenylene, wherein the $C_{3-8}$cycloalkylene and phenylene are optionally independently substituted with 1-4 substituents independently selected from the group consisting of $C_{1-4}$alkyl, $C_{1-4}$haloalkyl, $C_{1-4}$alkoxy, halo, cyano, or hydroxy. In some embodiments, $L^1$ is $C_1$-$C_{10}$alkylene (e.g., $C_2$-$C_3$alkylene).

Linker $L^1$ may be a linker between a pro-substrate and an enzyme substrate as disclosed in WO2006/130551, WO2014/159044, US2007/0015790, or US2014/0304842, which are incorporated herein by reference in their entireties. For example, $L^1$ may be a traceless linker such as trimethyl lock, quinone methide, dipeptidyl, para-amino benzyloxycarbonyl, or alkylenediaminocarbonyl linkers as shown in Scheme 1. Enzymatic biotransformation of $G^{E1}$ results in cleavage of the bond to the heteroatom to which $G^{E1}$ is attached to release the linker that may spontaneously self-immolate to release a benzothiazole luciferin analog. Some traceless linkers (e.g., alkylene linkers) may be spontaneously eliminated by β-elimination, as described in WO2006/130551.

Representative examples of an enzyme substrate $G^{E1}$ include a substrate for a protease, a cytochrome (CYP) P450 reductase, a monoamineoxidase (MAO), a flavin monooxygenase (FMO), glutathione S transferase (GST), a dealkylase (e.g., demethylase), a deacetylase, a deformylase, a sulfatase, a phosphatase (e.g., alkaline phosphatase (AP)), a beta-lactamase, and alcohol dehydrogenase, as described in WO2006/130551 or US2007/0015790, which are incorporated herein by reference in their entireties.

Representative protease substrates include, but are not limited to, the peptides Z-DEVD-, Z-LETD-, GP-, Suc-LLVY-, Z-LRR-, Z-nLPnLD-, Z-QEVY-, VP-, Z-VDVAD-, Z-VEID-, Z-ATAD-, Z-IEPD-, Z-IETD-, Z-TSAVLQ- and Z-VNSTLQ- as described by Cosby et al. in Cell Notes (2007) 18, pp. 9-11, which is incorporated herein by reference in its entirety. In the case of these protease substrates, $L^1$ is a bond, as the enzyme substrate is directly attached to the O or N at X or Y and is cleaved directly.

Representative examples of $G^E$ with traceless linkers are shown in Scheme 2.

Scheme 2

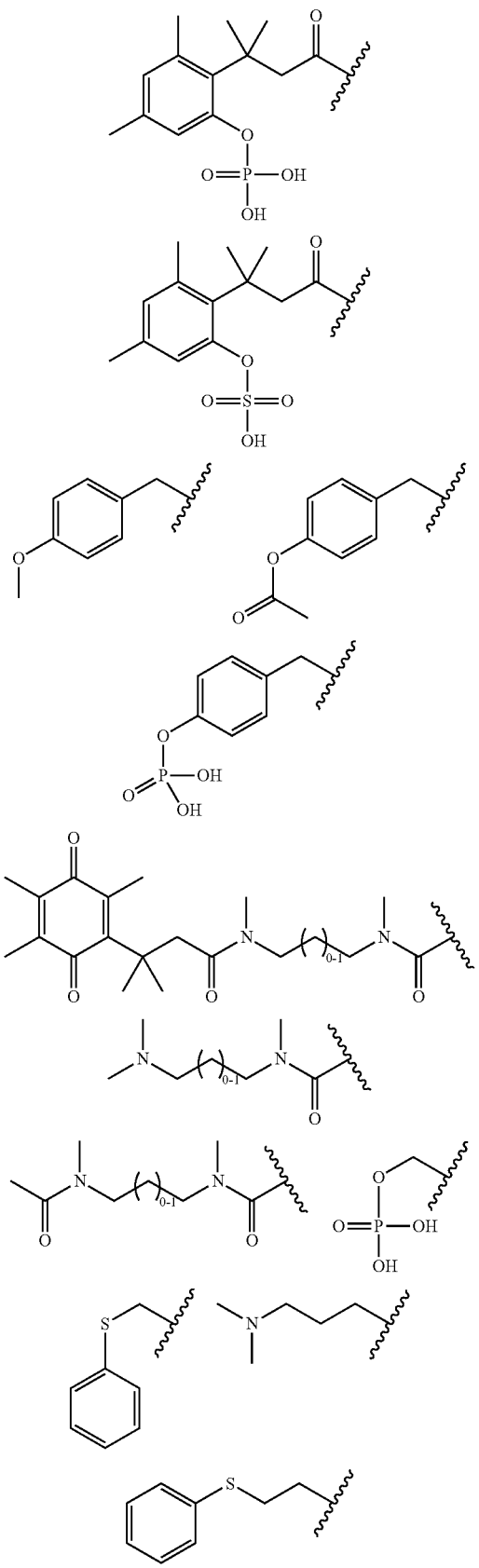
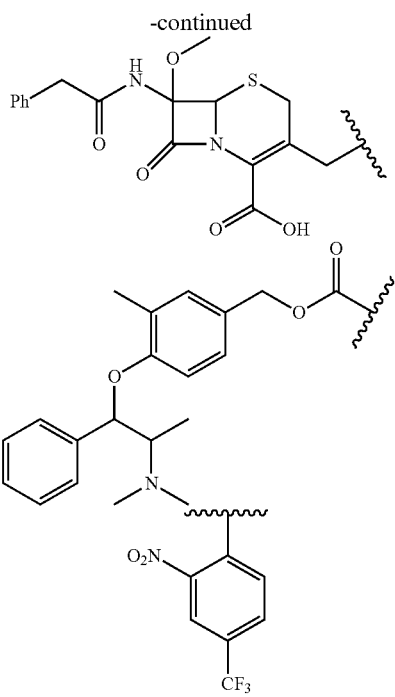

Compound names are assigned by using Struct=Name naming algorithm as part of CHEMDRAW® ULTRA.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry", 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention. A compound of the invention or a tautomer or a salt thereof includes: the compound, salts of the compound, tautomers of the compound, and tautomers of the salts of the compound.

The present disclosure also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Substitution with heavier isotopes such as deuterium, i.e., $^2$H, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

A compound described herein can be in the form of a salt. The selection of salts suitable for use in contact with the tissues of humans and lower animals without undue toxicity, irritation, allergic response and the like, and are commensurate with a reasonable benefit/risk ratio is within the scope of sound medical judgement. Pharmaceutically acceptable salts are well known in the art. For example, S. M. Berge, et al. describe pharmaceutically acceptable salts in detail in J Pharmaceutical Sciences, 1977, 66, 1-19, incorporated herein by reference. Acceptable salts of the compounds of this invention include those derived from suitable inorganic and organic acids and bases. Examples of acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pi crate, pivalate, propionate, stearate, succinate, sulfate, tartrate, thiocyanate, p-toluenesulfonate, undecanoate, valerate salts, and the like. Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzyl ethylenediamine, ethylenediamine, ethanolamine, diethanolamine, piperidine, piperazine, and the like.

A. Properties of the Compounds

The compounds of formula (I) and formula (II) may be substrates of luciferases to produce luminescence. The compounds may have improved water solubility, improved stability, improved cell permeability, increased biocompatibility with cells, reduced autoluminescence, and/or reduced toxicity.

"Luminescence" refers to the light output of a luciferase under appropriate conditions, e.g., in the presence of a suitable substrate such as a coelenterazine analogue. The light output may be measured as an instantaneous or near-instantaneous measure of light output (which is sometimes referred to as "T=0" luminescence or "flash") at the start of the luminescence reaction, which may be initiated upon addition of the coelenterazine substrate. The luminescence reaction in various embodiments is carried out in a solution. In other embodiments, the luminescence reaction is carried out on a solid support. The solution may contain a lysate, for example from the cells in a prokaryotic or eukaryotic expression system. In other embodiments, expression occurs in a cell-free system, or the luciferase protein is secreted into an extracellular medium, such that, in the latter case, it is not necessary to produce a lysate. In some embodiments, the reaction is started by injecting appropriate materials, e.g., coelenterazine analogue, buffer, etc., into a reaction chamber (e.g., a well of a multiwell plate such as a 96-well plate) containing the luminescent protein. In still other embodiments, the luciferase and/or coelenterazine analogues (e.g., compounds of formula (I) and (II)) are introduced into a host, and measurements of luminescence are made on the host or a portion thereof, which can include a whole organism or cells, tissues, explants, or extracts thereof. The reaction chamber may be situated in a reading device which can measure the light output, e.g., using a luminometer or photomultiplier. The light output or luminescence may also be measured over time, for example in the same reaction chamber for a period of seconds, minutes, hours, etc. The light output or luminescence may be reported as the average over time, the half-life of decay of signal, the sum of the signal over a period of time, or the peak output. Luminescence may be measured in Relative Light Units (RLUs).

Compounds of formula (I) and formula (II) can have an RLU of greater than or equal to 1, greater than or equal to 2, greater than or equal to 3, greater than or equal to 4, greater than or equal to 5, greater than or equal to 10, greater than or equal to 20, greater than or equal to 30, greater than or equal to 40, greater than or equal to 50, or greater than or equal to 100, relative to coelenterazine or a known coelenterazine analogue such as furimazine.

Compounds of formula (I) and formula (II) can have a λmax of 450-700 nanometers, 460-600 nanometers, 470-600 nanometers, 480-600 nanometers, 490-600 nanometers, 500-600 nanometers, 510-600 nanometers, 520-600 nanometers, 530-600 nanometers, 540-600 nanometers, 550-600 nanometers, 560-600 nanometers, 570-600 nanometers, 580-600 nanometers, 590-600 nanometers, 470-590 nanometers, 480-580 nanometers, 490-570 nanometers, 500-560 nanometers, or 510-550 nanometers. Compounds of formula (I) and formula (II) can have a λmax greater than or equal to 450 nanometers, greater than or equal to 460 nanometers, greater than or equal to 470 nanometers, greater than or equal to 480 nanometers, greater than or equal to 490 nanometers, greater than or equal to 500 nanometers, greater than or equal to 510 nanometers, greater than or equal to 520 nanometers, greater than or equal to 530 nanometers, greater than or equal to 540 nanometers, greater than or equal to 550 nanometers, greater than or equal to 560 nanometers, greater than or equal to 570 nanometers, greater than or equal to 580 nanometers, greater than or equal to 590 nanometers, greater than or equal to 600 nanometers, greater than or equal to 610 nanometers, greater than or equal to 620 nanometers, greater than or equal to 630 nanometers, greater than or equal to 640 nanometers, greater than or equal to 650 nanometers, greater than or equal to 660 nanometers, greater than or equal to 670 nanometers, greater than or equal to 680 nanometers, greater than or equal to 690 nanometers, or greater than or equal to 700 nanometers.

"Biocompatibility" refers to the tolerance of a cell (e.g., prokaryotic or eukaryotic) to a coelenterazine analogue (e.g., compounds of formula (I)). Biocompatibility of a coelenterazine analogue is related to the stress it causes on the host cell.

Enhanced biocompatibility of the coelenterazine analogues (e.g., compounds of formula (I)), may be determined by measuring cell viability and/or growth rate of cells. For example, enhanced biocompatibility of the coelenterazine analogues may be determined by measuring cell viability in the absence of luciferase expression of cells exposed to the coelenterazine analogues compared to native or known coelenterazines to determine how compatible and/or toxic the coelenterazine analogues are to the cells.

In particular, enhanced biocompatibility may be determined using cell viability analysis (e.g., using the CELL-TITER-GLO® Luminescent Cell Viability assay), an apoptosis assay (e.g., using the CASPASE-GLO® technology), or another method known in the art. The effect of the disclosed compounds on cell viability or apoptosis may be compared to the effect of native or known coelenterazine analogues on cell viability or apoptosis.

Enhanced biocompatibility may also be determined by measuring the effect of the coelenterazine analogues (e.g., compounds of formula (I)) on cell growth or gene expression. For example, enhanced biocompatibility of the compounds of formula (I) or formula (II) may be determined by measuring the cell number after a period of time or by determining the expression of stress response genes in a sample of cells that are exposed to compounds of formula (I) or formula (II) compared to cells exposed to a native or known coelenterazine or no coelenterazine. The effect of the disclosed compounds on cell growth or gene expression may be compared to a native or known coelenterazine.

B. Synthesis Methods

Compounds of formula (I) and formula (II) may be prepared by synthetic processes or by metabolic processes. Preparation of the compounds by metabolic processes includes those occurring in the human or animal body (in vivo) or processes occurring in vitro.

Compounds of formula (I) and formula (II), wherein the groups, can be synthesized as shown in Schemes 1-3. Suitable synthesis methods may also include, for example, those disclosed in U.S. Ser. No. 62/295,363 to Shakhmin et al., "COELENTERAZINE ANALOGUES," filed Feb. 15, 2016, which is incorporated by reference herein in its entirety.

Abbreviations which have been used in the descriptions of the Schemes that follow are: ACN for acetonitrile; CDI for carbonyldiimidazole; DCM for dichloromethane; DMF for dimethylformamide; eq for equivalents; EtOH for ethanol; h or hr for hour(s); HWE for Homer-Wadsworth-Emmons; MeOH for methanol; min. for minutes; RT/rt/r.t. for room temperature; TBDMS for tert-butyldimethylsilyl; TMG for 1,1,3,3-tetramethylguanidine; TFA for trifluoroacetic acid; THF for tetrahydrofuran; TMG for 1,1,3,3-tetramethylguanidine.

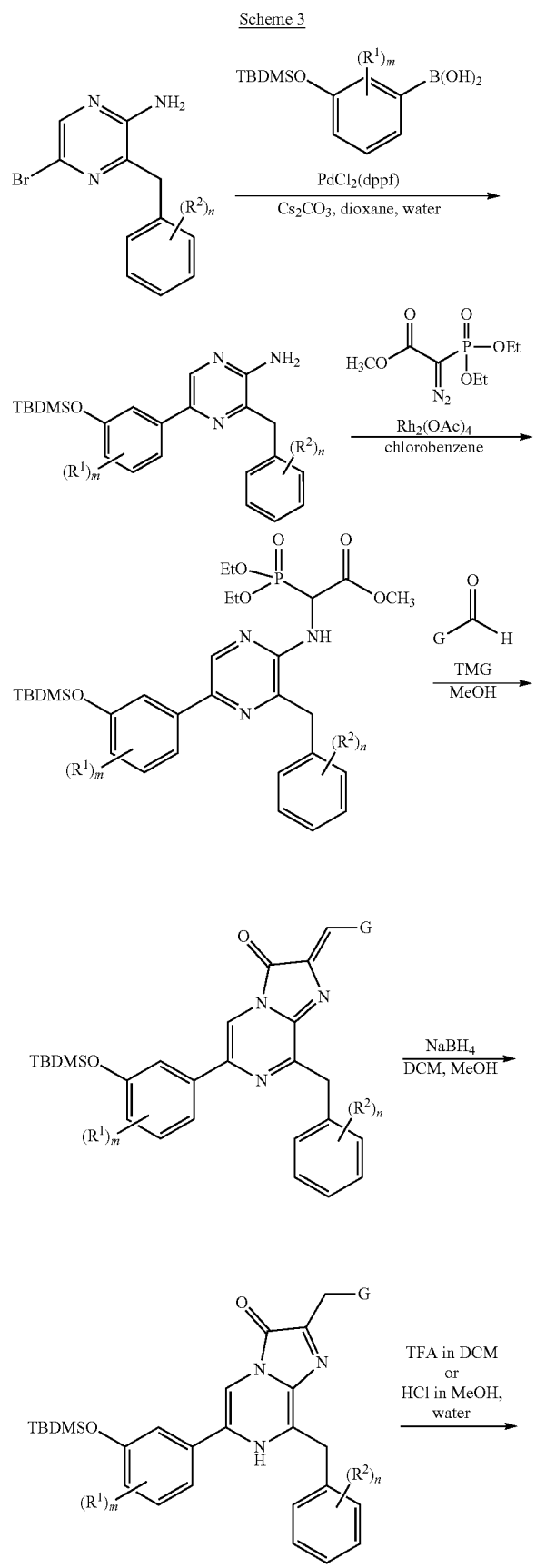

Scheme 3

31
-continued
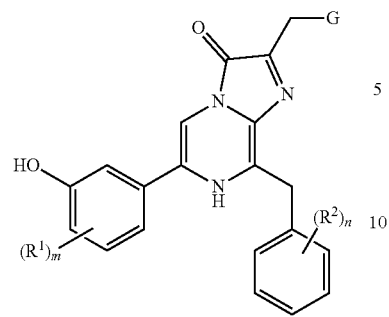
Scheme 3 shows a general synthetic route toward phenol containing coelenterazines of formula (I).
Scheme 4
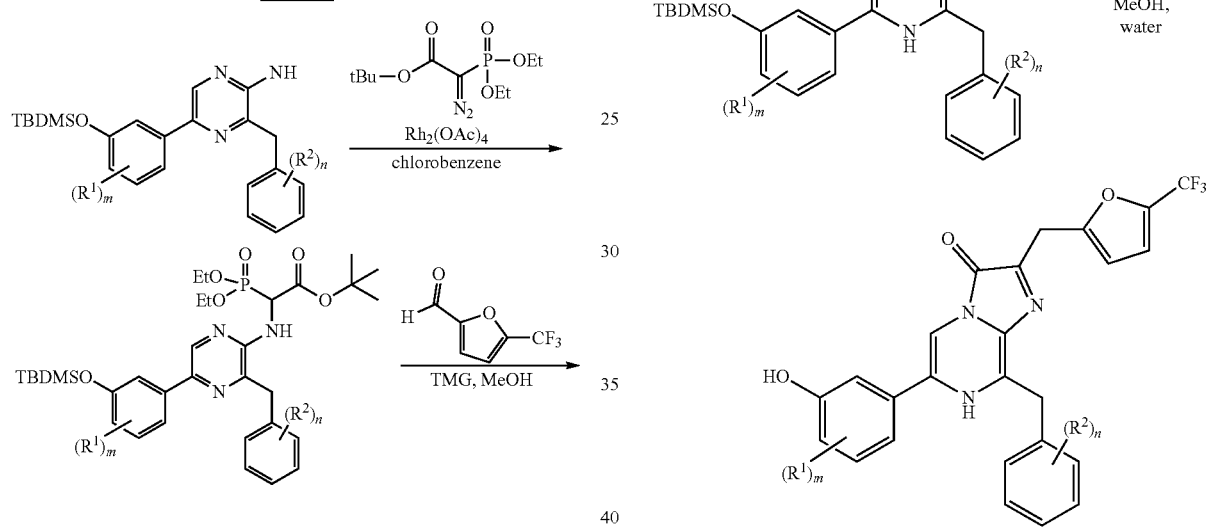
32
-continued
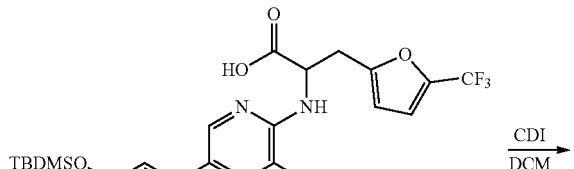
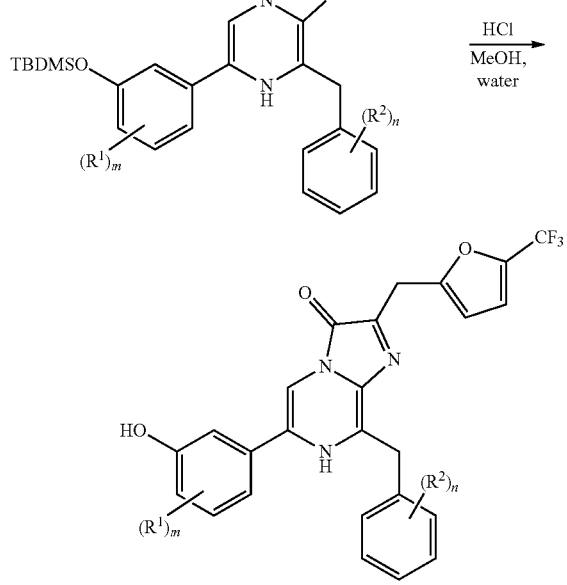
Scheme 4 shows a general synthesis of substituted furan-containing compounds of formula (I).
Scheme 5
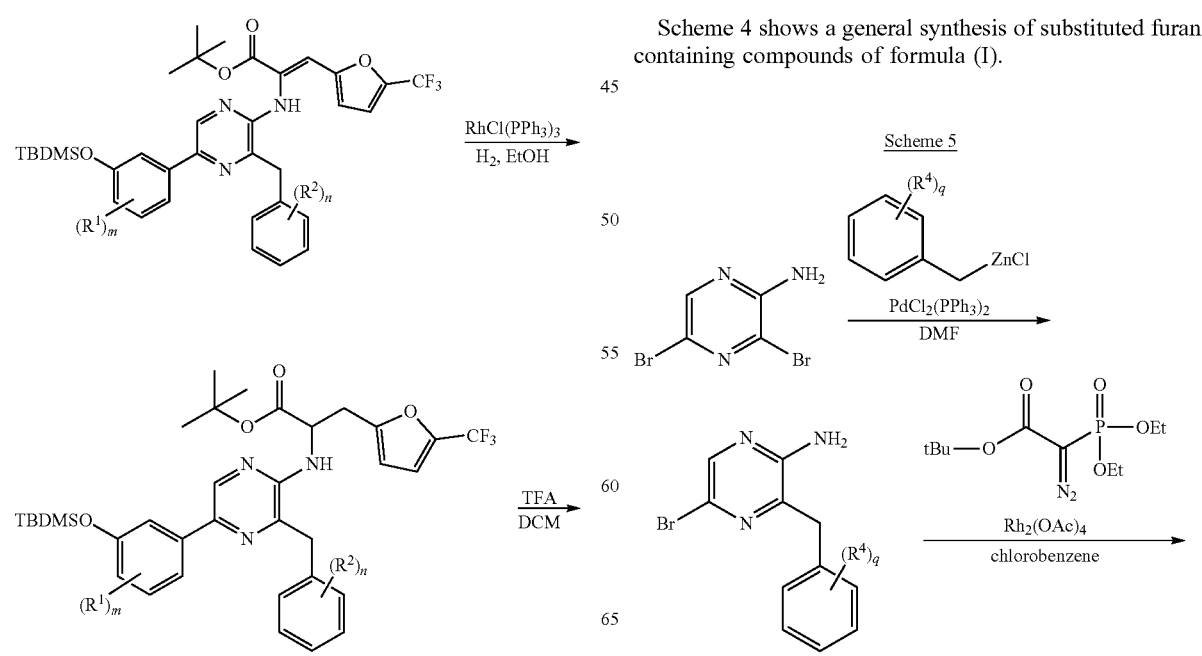

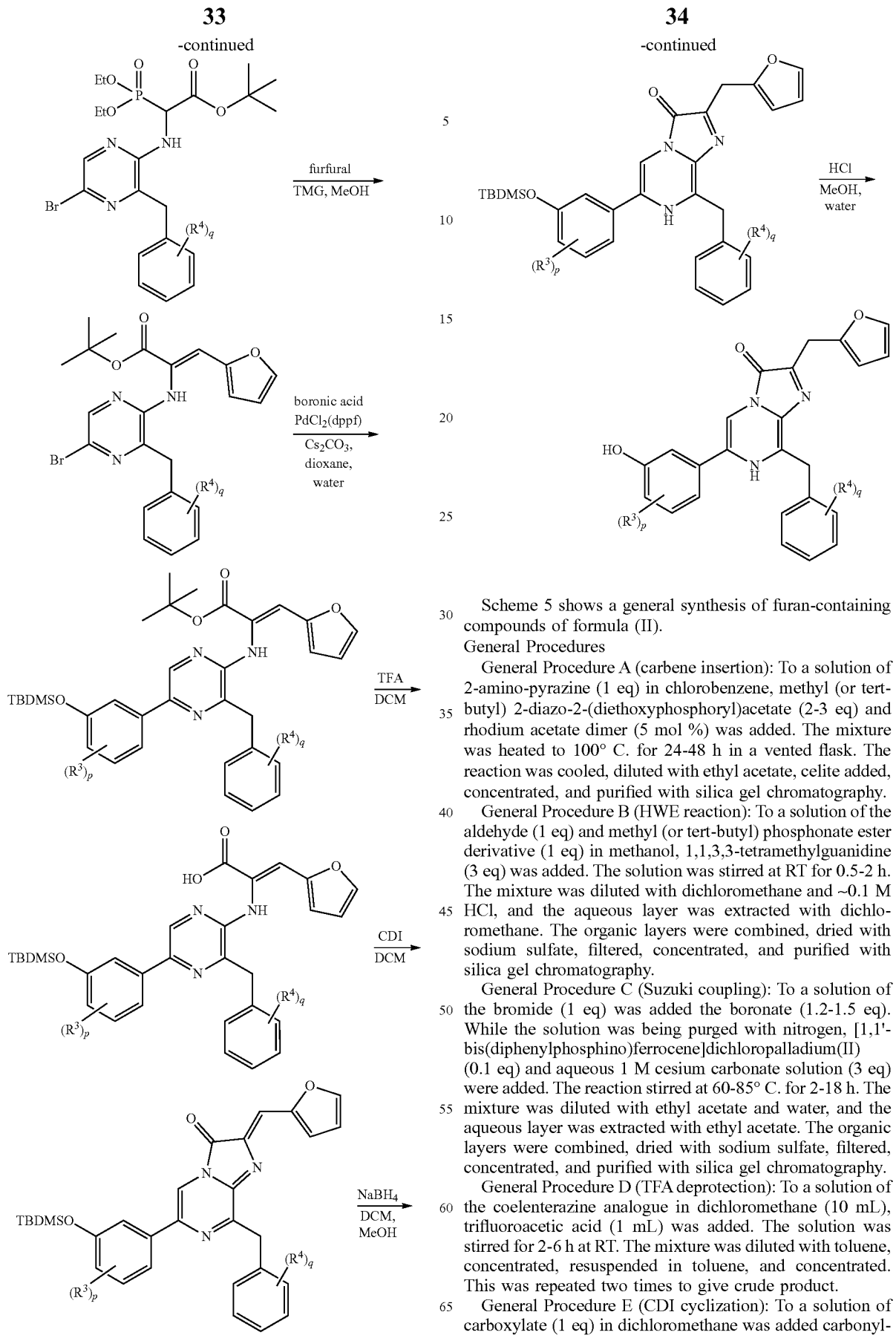

Scheme 5 shows a general synthesis of furan-containing compounds of formula (II).

General Procedures

General Procedure A (carbene insertion): To a solution of 2-amino-pyrazine (1 eq) in chlorobenzene, methyl (or tert-butyl) 2-diazo-2-(diethoxyphosphoryl)acetate (2-3 eq) and rhodium acetate dimer (5 mol %) was added. The mixture was heated to 100° C. for 24-48 h in a vented flask. The reaction was cooled, diluted with ethyl acetate, celite added, concentrated, and purified with silica gel chromatography.

General Procedure B (HWE reaction): To a solution of the aldehyde (1 eq) and methyl (or tert-butyl) phosphonate ester derivative (1 eq) in methanol, 1,1,3,3-tetramethylguanidine (3 eq) was added. The solution was stirred at RT for 0.5-2 h. The mixture was diluted with dichloromethane and ~0.1 M HCl, and the aqueous layer was extracted with dichloromethane. The organic layers were combined, dried with sodium sulfate, filtered, concentrated, and purified with silica gel chromatography.

General Procedure C (Suzuki coupling): To a solution of the bromide (1 eq) was added the boronate (1.2-1.5 eq). While the solution was being purged with nitrogen, [1,1'-bis(diphenylphosphino)ferrocene]dichloropalladium(II) (0.1 eq) and aqueous 1 M cesium carbonate solution (3 eq) were added. The reaction stirred at 60-85° C. for 2-18 h. The mixture was diluted with ethyl acetate and water, and the aqueous layer was extracted with ethyl acetate. The organic layers were combined, dried with sodium sulfate, filtered, concentrated, and purified with silica gel chromatography.

General Procedure D (TFA deprotection): To a solution of the coelenterazine analogue in dichloromethane (10 mL), trifluoroacetic acid (1 mL) was added. The solution was stirred for 2-6 h at RT. The mixture was diluted with toluene, concentrated, resuspended in toluene, and concentrated. This was repeated two times to give crude product.

General Procedure E (CDI cyclization): To a solution of carboxylate (1 eq) in dichloromethane was added carbonyldiimidazole (2 eq). The mixture stirred for 0.5-1 h at RT. The mixture was diluted with dichloromethane and ~0.1 M HCl, and the aqueous layer was extracted with dichloromethane. The organic layers were combined, dried with sodium sulfate, filtered, and concentrated to give crude product.

General Procedure F (reduction): A suspension of the dehydro-coelenterazine (1 eq) in dichloromethane and methanol (1:1) was chilled with an ice bath. Sodium borohydride (5 eq) was added, and the mixture stirred for 0.5-2 h. The mixture was diluted with dichloromethane and ~0.1 M HCl, and the aqueous layer was extracted with dichloromethane. The organic layers were combined, dried with sodium sulfate, filtered, concentrated, and purified with silica gel chromatography.

General Procedure G (HCl deprotection): To a solution of the coelenterazine analogue in methanol (10 mL), aqueous HCl (6M, 1 mL) was added. The solution stirred for 2-6 h at RT. The mixture was diluted with dichloromethane and water, and the aqueous layer was extracted with dichloromethane. The organic layers were combined, dried with sodium sulfate, filtered, concentrated, and purified with silica gel chromatography.

General Procedure H (Nitro reduction): To a solution of the nitro coelenterazine in ethanol, catalytic palladium on carbon (10%) was added. The solution was purged with nitrogen. Hydrogen (1 atm) was added, and the suspension stirred at RT for 2-8 h. The solution was purged with nitrogen and filtered over celite. The filtrate was collected, celite added, concentrated, and purified with silica gel chromatography.

Optimum reaction conditions and reaction times for each individual step can vary depending on the particular reactants employed and substituents present in the reactants used. Specific procedures are provided in the Examples section. Reactions can be worked up in the conventional manner, e.g., by eliminating the solvent from the residue and further purified according to methodologies generally known in the art such as, but not limited to, crystallization, distillation, extraction, trituration, and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step) or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

3. METHODS OF USE AND KITS

The compounds of the disclosure may be used in any way that luciferase substrates, e.g., coelenterazine analogues, have been used. For example, they may be used in a bioluminogenic method that employs an analogue of coelenterazine to detect one or more molecules in a sample, e.g., an enzyme, a cofactor for an enzymatic reaction, an enzyme substrate, an enzyme inhibitor, an enzyme activator, or OH radicals, or one or more conditions, e.g., redox conditions. The sample may include an animal (e.g., a vertebrate), a plant, a fungus, physiological fluid (e.g., blood, plasma, urine, mucous secretions), a cell, a cell lysate, a cell supernatant, or a purified fraction of a cell (e.g., a subcellular fraction). The presence, amount, spectral distribution, emission kinetics, or specific activity of such a molecule may be detected or quantified. The molecule may be detected or quantified in solution, including multiphasic solutions (e.g., emulsions or suspensions), or on solid supports (e.g., particles, capillaries, or assay vessels).

In certain embodiments, the compounds of formula (I) or formula (II) may be used to quantify a molecule of interest. In some embodiments, a coelenterazine analogue (e.g., a native or known coelenterazine or a compound of formula (I) or formula (II)) can be used as a probe of a specific biochemical activity, e.g., apoptosis or drug metabolism.

In certain embodiments, the compounds of formula (I) or formula (II) can be used with an inhibitor of *Oplophorus*-derived luciferases and/or *Oplophorus*-luciferase derived bioluminescent complexes. Exemplary inhibitors of *Oplophorus*-derived luciferases and/or *Oplophorus*-luciferase derived bioluminescent complexes are described, for example, in International Patent Publication Nos. WO2016/210294 and WO2018/125992, and in U.S. Pat. App. Ser. No. 62/679,205 filed Jun. 1, 2018, and U.S. Pat. App. Ser. No. 62/665,346, filed May 1, 2018, all of which are herein incorporated by reference in their entireties.

In certain embodiments, the compounds of formula (I) or formula (II) can be used for detecting luminescence in live cells, e.g., in vivo. In some embodiments, a luciferase can be expressed in cells (as a reporter or otherwise), and the cells treated with a coelenterazine analogue (e.g., a compound of formula (I) or formula (II)), which will permeate cells in culture, react with the luciferase, and generate luminescence. In addition to being cell permeant, the compounds of formula (I) or formula (II) show comparable biocompatibility to native coelenterazine in terms of cell viability. In some embodiments, the compounds of formula (I) or formula (II) containing chemical modifications known to increase the stability of native coelenterazine in media can be synthesized and used for more robust, live cell luciferase-based reporter assays. In still other embodiments, a sample (including cells, tissues, animals, etc.) containing a luciferase and a compound of formula (I) or formula (II) may be assayed using various microscopy and imaging techniques, e.g., in vivo imaging. In still other embodiments, a secretable luciferase is expressed in cells as part of a live-cell reporter system.

In certain embodiments, the compounds of formula (I) or formula (II) disclosed herein may be provided as part of a kit. In some embodiments, the kit may include one or more luciferases (in the form of a polypeptide, a polynucleotide, or both) and a coelenterazine analogue of formula (I) or formula (II), along with suitable reagents and instructions to enable a user to perform assays such as those disclosed herein. The kit may also include one or more buffers such as those disclosed herein. In some embodiments, the kit may further include an inhibitor of Oplophorus-derived luciferases and/or Oplophorus-luciferase derived bioluminescent complexes, as described above.

Buffers include citric acid or citrate buffer, MES, 1,4-Piperazinediethanesulfonic acid, or HEPES; inorganic phosphate, for example, in the form pyrophosphate or potassium phosphate; a chelator such as EDTA, CDTA or 1,2-Diaminocyclohexanetetraacetic acid; a salt such as sodium fluoride, magnesium sulfate; a surfactant or detergent such as TERGITOL® (e.g. a non-ionic nonylphenol ethoxylate), dodecyltrimethylammonium bromide (DTAB) or THESIT® (hydroxypolyethoxydodecane); a defoamer such as INDUSTROL® DF204 (organic defoamer) or MAZET® DF (silicone defoamer); a protein stabilizer such as gelatin, PRIONEX®10% (gelatin, Type A) or albumin (e.g. BSA, HSA) or glycerol; adenosine triphosphate (ATP) or adenosine monophosphate (AMP). Other components may include polyethylene glycol, polyvinyl pyridine, crown ether, or cyclodextrin.

A. In Vivo Imaging

The compounds of the disclosure can be used for imaging of live cells such as in vivo and ex vivo bioluminescence imaging. For example, the compounds of the disclosure can be used with a coelenterazine utilizing luciferase for bioluminescence imaging tissue sections or cells in a live animal. In vivo bioluminescence imaging is a versatile and sensitive tool based on the detection of emitted light from cells or tissues. Bioluminescence has been used to track tumor cells, bacterial and viral infections, gene expression and treatment response in a non-invasive manner. Bioluminescence imaging provides for longitudinal monitoring of a disease course in the same animal, a desirable alternative to analyzing a number of animals at many time points during the course of the disease. In some embodiments, the compounds of the disclosure can be used in vivo to monitor biological processes such as cell movement, tumor progression, gene expression, and viral infection in a variety of animal models. In some embodiments, the compounds of the disclosure can be used for imaging in a transgenic animal, such as a transgenic mouse. Transgenic animals, including cells or tissues, can represent models of cell function and disease in humans. Accordingly, these animals are useful in studying the mechanisms behind cell function and related events, in generating and testing products (e.g., antibodies, small molecules etc.), and in treating and diagnosing associated human diseases, including cancer and autoimmune conditions. In some embodiments, the transgenic animal can further provide an indication of the safety of a particular agent for administration to a human. The effect of the agent can be studied by administration of a particular agent and the compounds of the disclosure to specific cells or the whole body and performing bioluminescent imaging to look for specific affects. The animal- and cell-based models and compounds of the disclosure may be used to identify drugs, pharmaceuticals, therapies and interventions that may be effective in treating disease.

In some embodiments, the compounds of the disclosure can be used for bioluminescence imaging of cells or animals that have been transformed to express a fusion protein, such as a fusion protein comprising a luciferase. In some embodiments, the transgenic animal or cell can express a fusion protein comprising a luciferase. In some embodiments, the luciferase can be a coelenterazine-utilizing luciferase, such as an *Oplophorus* or *Oplophorus*-derived luciferase, a *Renilla* luciferase, a *Gaussia* luciferase, such as a *Gaussia princeps* luciferase, a *Metridia* luciferase, such as *Metridia longa* and *Metridia pacifica* luciferases, a *Vargula* luciferase, such as a *Vargula hilgendorfii* luciferase, a *Pleuromamma xiphias* luciferase, and variants, recombinants, and mutants thereof. In some embodiments, the polynucleotide sequence encoding the fusion protein is operably linked to a promoter. In some embodiments, the promoter can be a constitutive promoter, an inducible promoter, a repressible promoter, or a regulatable promoter. In some embodiments, the promoter can also be a tissue specific promoter.

In some embodiments, a fusion protein of a bioluminescent protein and a heterologous protein of interest, such as a fluorescent protein, may be connected directly to each other by peptide bonds or may be separated by intervening amino acid sequences. In some embodiments, the fusion polypeptides may also contain sequences exogenous to the bioluminescent protein and the heterologous protein of interest, such as a fluorescent protein. For example, the fusion protein may include targeting or localization sequences, tag sequences, sequences of other fluorescent proteins or bioluminescent proteins, or other chromophores. In some embodiments, the targeting sequence may direct localization of the fusion protein to a specific tissue, cell-type (e.g. muscle, heart, or neural cell), cellular compartment (e.g., mitochondria or other organelle, nucleus, cytoplasm, or plasma membrane), or protein. Moreover, the fusion may contain sequences from multiple fluorescent or bioluminescent proteins, or variants thereof, and/or other selected proteins. In some embodiments, the luciferase is fused to a HALOTAG® protein or a fluorescent protein, such as green fluorescent protein (GFP), red fluorescent protein (RFP), or orange-red fluorescent protein.

The bioluminescence produced within a cell, such as in a cell of a transgenic animal, is capable of being imaged or detected by a variety of means well known in the art. For example, the fusion protein and the compounds of the disclosure that have localized to their intended sites in a transgenic animal may be imaged in a number of ways. A reasonable estimate of the time to achieve localization may be made by one skilled in the art. Furthermore, the state of localization as a function of time may be followed by imaging the bioluminescence generated from the fusion protein and the compounds of the disclosure. Since the imaging, or measuring photon emission from the subject, may last up to tens of minutes, the transgenic animal can be immobilized during the imaging process.

In vivo imaging can be performed using the naked eye or any sort for camera (still or video). Imaging of the bioluminescence involves the use of, e.g., a photodetector capable of detecting extremely low levels of light—typically single photon events—and integrating photon emission until an image can be constructed. Examples of such sensitive photodetectors include devices that intensify the single photon events before the events are detected by a camera, and cameras (cooled, for example, with liquid nitrogen) that are capable of detecting single photons over the background noise inherent in a detection system. The "photodetector device" used should have a high enough sensitivity to enable the imaging of faint light from within a mammal in a reasonable amount of time, and to use the signal from such a device to construct an image.

The bioluminescence signal can be detected with a highly sensitive, intensified charge coupled device (CCD) camera. In certain embodiments, an intensified CCD camera sensitive enough to detect a bioluminescent signal and with wide enough dynamic range to also detect a fluorescent signal is used for imaging. Suitable cameras are known in the art and include, but are not limited to, an Olympus LV200 Bioluminescence Imaging System, an integrated imaging system (IVIS™ Imaging System, Caliper Life Sciences) controlled using LivingImage™ software (Caliper Life Sciences), or a custom-built two-photon fluorescence lifetime imaging microscope (Yasuda Curr Opin Neurobiol. 2006; 16:551-561). In some embodiments, the camera is mounted in a light-proof container that provides for anesthesia, platforms for the animal, such as a mouse, and internal lighting.

The in vivo imaging can be a non-invasive whole animal imaging that have been described (Contag, C., U.S. Pat. No. 5,650,135, Jul. 22, 1997), herein incorporated by reference; Contag, P., et al, *Nature Medicine* 4(2):245-247, 1998; Contag, C., et al, *OSA TOPS on Biomedical Optical Spectroscopy and Diagnostics* 3:220-224, 1996; Contag, C. H., *Photochemistry and Photobiology* 66(4):523-531, 1997; Contag, C. H., al, *Molecular Microbiology* 18(4):593-603, 1995). Sensitivity of detecting light emitted from internal organs depends on several factors, including the level of luciferase expression, the depth of labeled cells within the body (the distance that the photons must travel through tissue), and the sensitivity of the detection system.

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Image Processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

It will be understood that the entire animal or subject need not necessarily be in the detection field of the photodetection device. For example, if one is measuring a fusion protein targeted to a particular region of the subject, only light from that region, and a sufficient surrounding "dark" zone, need be measured to obtain the desired information.

Once a photon emission image is generated, it is typically superimposed on a "normal" reflected light image of the subject to provide a frame of reference for the source of the emitted photons (i.e., localize the fusion proteins with respect to the subject). A "composite" image formed by the superimposition of the photon emission image on the reflected light image is then analyzed to determine the location and/or amount of a target in the subject.

B. Bioluminescence Resonance Energy Transfer (BRET)

The disclosed compounds can be used in any method for detecting ligand-protein and/or protein-protein interactions. In some embodiments, the compounds of the disclosure can be used in an in vivo or in vitro bioluminescence resonance energy transfer (BRET) system. With respect to BRET, energy transfer from a bioluminescent donor to a fluorescent acceptor results in a shift in the spectral distribution of the emission of light. This energy transfer may enable real-time monitoring of protein-protein or ligand-protein interaction in vitro or in vivo, such as the interaction and dissociation of the partners. Examples of BRET systems, such as Nano-BRET™ systems, are described, for example, in U.S. Pat. No. 10,024,862, U S. Patent Publication No. 2014/0194307, U.S. Pat. No. 10,067,149, and U.S. Patent Publication No. 2014/0194325.

In some embodiments, the luminescent enzymes used in BRET analysis can be used to determine if two molecules are capable of binding to each other or co-localize in a cell. For example, a luminescent enzyme can be used as a bioluminescence donor molecule which is combined with a molecule or protein of interest to create a first fusion protein. In some embodiments, the luminescent enzyme can be conjugated with an antibody, a protein, a receptor, a drug, a drug carrier, a peptide, a sugar, a fatty acid, a nanoparticle, or other biomolecule. In various embodiments, the first fusion protein contains a luminescent enzyme and a protein of interest. In various embodiments, the first fusion proteins containing the luminescent enzyme can be used in BRET analysis to detect protein/protein interaction in systems including but not limited to cell lysates, intact cells, and living animals. In some embodiments, the BRET analysis can also include an inhibitor of *Oplophorus*-derived luciferases and/or *Oplophorus*-luciferase derived bioluminescent complexes, as described above.

In some embodiments, the fluorescent acceptor can be a fluorophore, such as a fluorescent protein, fluorescent molecule, fluorescent label, or fluorescent tracer. In some embodiments, the fluorescent tracer can be a small molecule tagged to a fluorophore. In some embodiments, the fluorescent acceptor can be a second fusion protein that includes a fluorescent acceptor conjugated to an antibody, a protein, a receptor, a drug, a drug carrier, a peptide, a sugar, a fatty acid, a nanoparticle, or other biomolecule.

In various embodiments, HALOTAG® can be used as a fluorescent acceptor molecule. In some embodiments, HALOTAG® or can be fused to a second protein of interest or to a luminescent enzyme. For example, a luminescent enzyme can be fused to HALOTAG®, expressed in cells or animals, and labeled with a fluorescent HALOTAG® ligand such as HALOTAG® TMR ligand. In another example, a luminescent enzyme can be fused to fluorescent protein and expressed in cells or animals. In some embodiments, BRET may be performed using luminescent enzymes in combination with fluorescent proteins, including but not limited to GFP, RFP, orange-red fluorescent protein, or fluorescent labels including fluorescein, rhodamine green, Oregon green, or Alexa 488, to name a few non-limiting examples.

In some embodiments, the disclosed compounds can be used in a target engagement assay, such as NANOBRET™ Target Engagement (TE) Assay, to measure compound binding at select target proteins, such as drug Target interaction, in intact cells in real time. For example, the NANOBRET™ TE Assay can include four components: an expressed cellular target protein that is fused to the bright NANOLUC® luciferase; a cell-permeable fluorescent tracer that specifically binds to the target protein; one or more of the disclosed compounds used as a substrate for the NANOLUC® luciferase; and a cell-impermeable inhibitor for NANOLUC® luciferase. The assay uses bioluminescence resonance energy transfer (BRET), achieved by transferring the luminescent energy from NANOLUC® luciferase to the fluorescent tracer that is bound to the target protein-NANOLUC® fusion. This energy transfer makes it possible to directly measure compound binding affinity as well as compound-target residence time.

In some embodiments, compounds that are applied to the cells and specifically can engage the intracellular target protein-NANOLUC® fusion and will result in a decrease in BRET. In some embodiments, to ensure accurate assessment of intracellular target engagement, a NANOLUC® inhibitor can be used to mitigate any extracellular NANOLUC® signal that may arise from cells compromised during handling, while not adversely affecting NANOLUC® luciferase expressed within healthy living cells.

The BRET system may further comprise a photodetector or imaging device for detecting light emitted from the bioluminescent fusion protein, such as, but not limited to, an optical microscope, a digital microscope, a luminometer, a charged coupled device (CCD) image sensor, a complementary metal-oxide-semi conductor (CMOS) image sensor, or a digital camera.

C. Formulation and Administration

For whole animal studies, the disclosed imaging probes are preferably formulated for parenteral administration. Parenteral formulations can be prepared as aqueous compositions using techniques known in the art. Typically, such compositions are prepared as solutions or suspensions; solid forms suitable to prepare solutions or suspensions upon the addition of a reconstitution medium; emulsions, such as water-in-oil (w/o) emulsions, oil-in-water (o/w) emulsions, and microemulsions thereof, liposomes, or emulsomes.

The term "parenteral," as used herein, refers to modes of administration which include intravenous, intramuscular, intraperitoneal, intrasternal, subcutaneous and intraarticular injection and infusion.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl) sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

4. EXAMPLES

Example 1. 8-benzyl-6-(3-((tert-butyldimethylsilyl)oxy)phenyl)-2-(3-(methoxymethyl)benzyl)imidazo[1,2-a]pyrazin-3(7H)-one (JRW-0372)

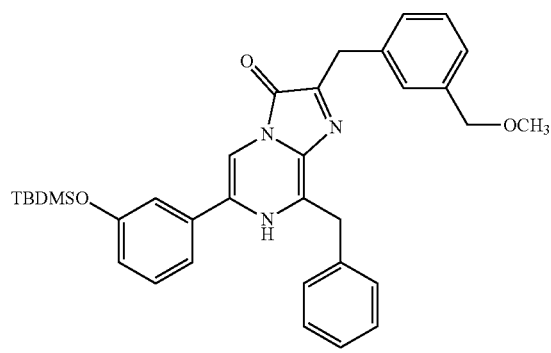 [SMILES: COCc1cccc(Cc2nc3c(Cc4ccccc4)[nH]c(-c4cccc(O[Si](C)(C)C(C)(C)C)c4)cn-3c2=O)c1]

Step 1. 3-benzyl-5-(3-((tert-butyldimethylsilyl)oxy)phenyl)pyrazin-2-amine (JRW-0218)

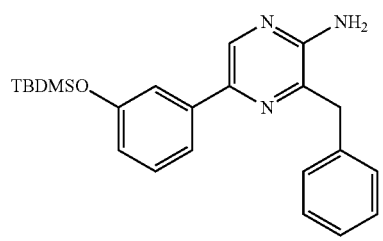 [SMILES: CC(C)(C)[Si](C)(C)Oc1cccc(-c2cnc(N)c(Cc3ccccc3)n2)c1]

To a solution of 3-benzyl-5-bromopyrazin-2-amine (300 mg, 1.14 mmol) in dioxane (5 mL), (3-((tert-butyldimethylsilyl)oxy)phenyl)boronic acid (430 mg, 1.70 mmol) was added. While the solution was being purged with nitrogen, [1,1'-bis(diphenylphosphino)ferrocene]dichloropalladium (II) (93 mg, 0.11 mmol) and cesium carbonate (3.4 mL, 1M, 3.4 mmol) were added. The reaction stirred at 60° C. for 30 min. The mixture was diluted with ethyl acetate and water, and the aqueous layer was extracted with ethyl acetate. The organic layers were combined, dried with sodium sulfate, filtered, concentrated, and purified with silica gel chromatography to give crude product (490 mg) as a brown solid. ESI MS m/z 392 [M+H]⁺.

Step 2. Methyl 2-((3-benzyl-5-(3-((tert-butyldimethylsilyl)oxy)phenyl)pyrazin-2-yl)amino)-2-(diethoxyphosphoryl)acetate (JRW-0226)

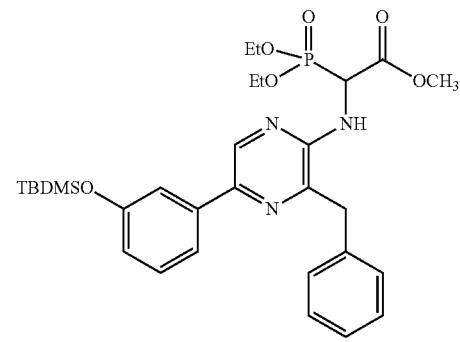 [SMILES: CCOP(=O)(OCC)C(Nc1ncc(-c2cccc(O[Si](C)(C)C(C)(C)C)c2)nc1Cc1ccccc1)C(=O)OC]

Following general procedure A, 3-benzyl-5-(3-((tert-butyldimethylsilyl)oxy)phenyl)pyrazin-2-amine (450 mg, 1.15 mmol) was reacted with methyl 2-diazo-2-(diethoxyphosphoryl)acetate (814 mg, 3.45 mmol) to afford the desired product (500 mg, 72%) as a brown solid. ESI MS m/z 600 [M+H]⁺.

Step 3. 8-benzyl-6-(3-((tert-butyldimethylsilyl)oxy)phenyl)-2-(3-(methoxymethyl)benzylidene)imidazo[1,2-a]pyrazin-3(2H)-one (JRW-0370)

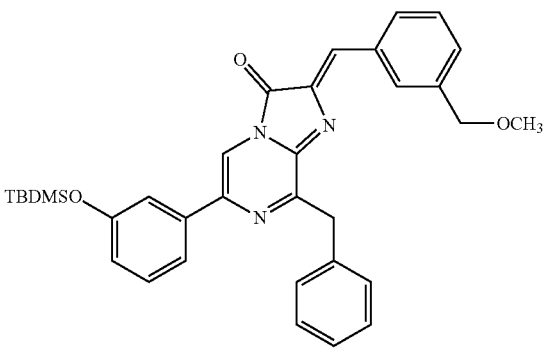 [SMILES: COCc1cccc(/C=C2\N=C3C(Cc4ccccc4)=NC(c4cccc(O[Si](C)(C)C(C)(C)C)c4)=CN3C2=O)c1]

Following general procedure B, methyl 2-((3-benzyl-5-(3-((tert-butyldimethylsilyl)oxy)phenyl)pyrazin-2-yl)amino)-2-(diethoxyphosphoryl)acetate (275 mg, 0.46 mmol) was reacted with 3-(methoxymethyl)benzaldehyde (75 mg, 0.50 mmol) to afford a mixture of the product and de-silylated product (157 mg) as a purple black solid. ESI MS m/z 564, 450 [M+H]⁺.

Step 4. 8-benzyl-6-(3-((tert-butyldimethylsilyl)oxy) phenyl)-2-(3-(methoxymethyl)benzyl)imidazo[1,2-a] pyrazin-3(7H)-one (JRW-0372)

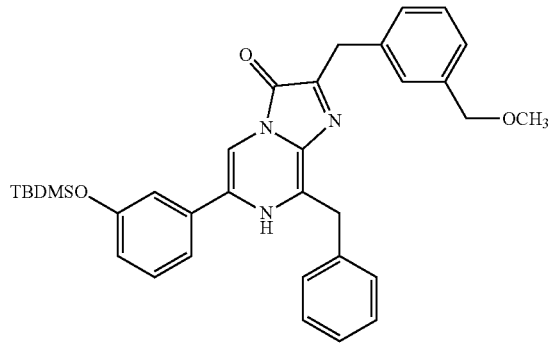 [SMILES: COCc1cccc(Cc2nc3c(Cc4ccccc4)[nH]c(-c4cccc(O[Si](C)(C)C(C)(C)C)c4)cn-3c2=O)c1]

Following general procedure F, 8-benzyl-6-(3-((tert-butyldimethylsilyl)oxy)phenyl)-2-(3-(methoxymethyl)benzylidene)imidazo[1,2-a]pyrazin-3(2H)-one (155 mg, 0.27 mmol) was reacted with sodium borohydride (52 mg, 1.37 mmol) to afford desired product (81 mg, 52%) as an orange solid. ESI MS m/z 566 [M+H]$^+$.

Example 2. 8-benzyl-6-(3-hydroxyphenyl)-2-(3-(methoxymethyl)benzyl)imidazo[1,2-a]pyrazin-3 (7H)-one (JRW-0373)

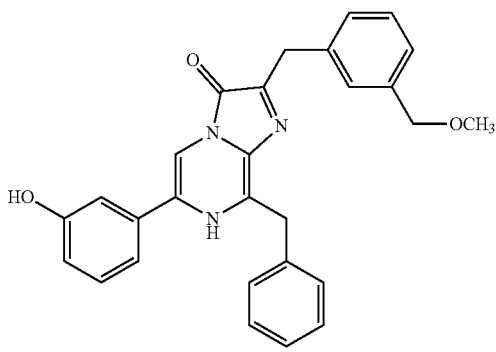 [SMILES: COCc1cccc(Cc2nc3c(Cc4ccccc4)[nH]c(-c4cccc(O)c4)cn-3c2=O)c1]

Following general procedure D, 8-benzyl-6-(3-((tert-butyldimethylsilyl)oxy)phenyl)-2-(3-(methoxymethyl)benzyl)imidazo[1,2-a]pyrazin-3(7H)-one (70 mg, 0.12 mmol) was reacted with TFA (1 mL) to afford the desired product (23 mg, 42%) as an orange solid. ESI MS m/z 452 [M+H]$^+$.

Example 3. 2-(benzo[d][1,3]dioxol-5-ylmethyl)-8-benzyl-6-(3-hydroxyphenyl)imidazo[1,2-a]pyrazin-3 (7H)-one (JRW-0777)

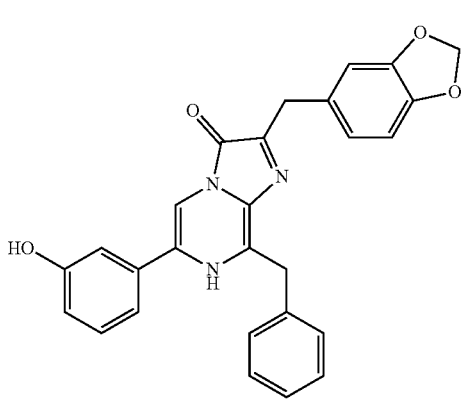 [SMILES: O=c1c(Cc2ccc3c(c2)OCO3)nc2c(Cc3ccccc3)[nH]c(-c3cccc(O)c3)cn1-2]

Step 1. 2-(benzo[d][1,3]dioxol-5-ylmethylene)-8-benzyl-6-(3-((tert-butyldimethylsilyl)oxy)phenyl) imidazo[1,2-a]pyrazin-3(2H)-one (JRW-0775)

Following general procedure B, methyl 2-((3-benzyl-5-(3-((tert-butyldimethylsilyl)oxy)phenyl)pyrazin-2-yl) amino)-2-(diethoxyphosphoryl)acetate (72 mg, 0.12 mmol) was reacted with benzo[d][1,3]dioxole-5-carbaldehyde (20 mg, 0.13 mmol) to afford a mixture of the product and de-silylated product (20 mg) as a red black solid. ESI MS m/z 564, 450 [M+H]$^+$.

Step 2. 2-(benzo[d][1,3]dioxol-5-ylmethyl)-8-benzyl-6-(3-((tert-butyldimethylsilyl)oxy)phenyl)imidazo[1,2-a]pyrazin-3(7H)-one (JRW-0776)

Example 4. 8-benzyl-2-(4-fluorobenzyl)-6-(3-hydroxyphenyl)imidazo[1,2-a]pyrazin-3(7H)-one (JRW-0786)

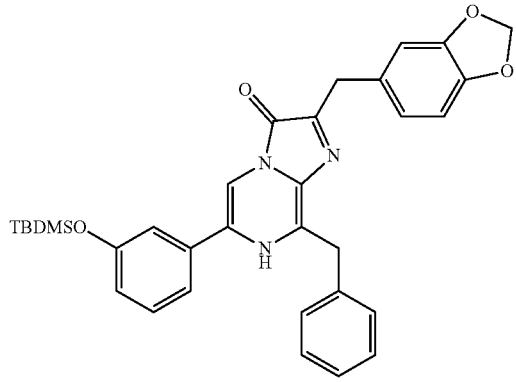 [SMILES: CC(C)(C)[Si](C)(C)Oc1cccc(-c2cn3c(=O)c(Cc4ccc5c(c4)OCO5)nc-3c(Cc3ccccc3)[nH]2)c1]

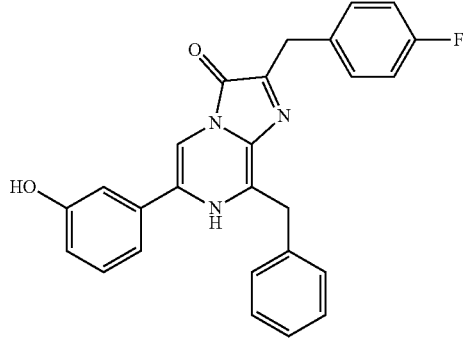

Following general procedure F, 2-(benzo[d][1,3]dioxol-5-ylmethylene)-8-benzyl-6-(3-((tert-butyldimethylsilyl)oxy)phenyl)imidazo[1,2-a]pyrazin-3(2H)-one (20 mg, 0.035 mmol) was reacted with sodium borohydride (7 mg, 0.18 mmol) to afford crude product as a yellow glass. ESI MS m/z 566 [M+H]$^+$.

Step 3. 2-(benzo[d][1,3]dioxol-5-ylmethyl)-8-benzyl-6-(3-hydroxyphenyl)imidazo[1,2-a]pyrazin-3(7H)-one (JRW-0777)

Step 1. 8-benzyl-6-(3-((tert-butyldimethylsilyl)oxy)phenyl)-2-(4-fluorobenzylidene)imidazo[1,2-a]pyrazin-3(2H)-one (JRW-0784)

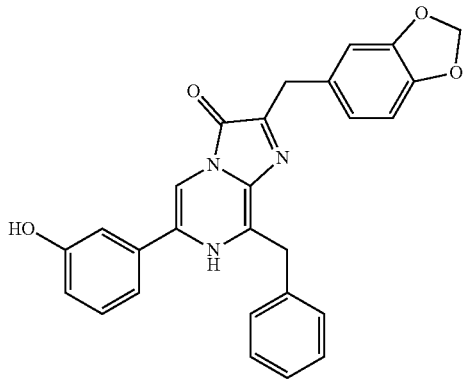 [SMILES: O=c1c(Cc2ccc3c(c2)OCO3)nc2c(Cc3ccccc3)[nH]c(-c3cccc(O)c3)cn1-2]

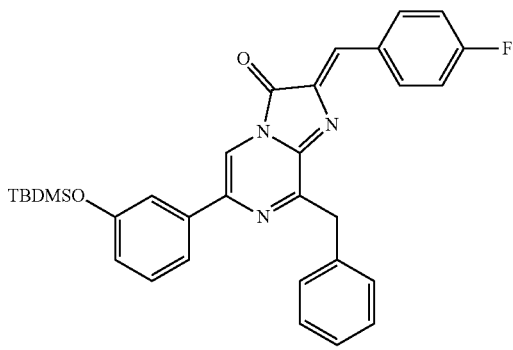 [SMILES: CC(C)(C)[Si](C)(C)Oc1cccc(C2=CN3C(=O)/C(=C/c4ccc(F)cc4)N=C3C(Cc3ccccc3)=N2)c1]

Following general procedure D, 2-(benzo[d][1,3]dioxol-5-ylmethyl)-8-benzyl-6-(3-((tert-butyldimethylsilyl)oxy)phenyl)imidazo[1,2-a]pyrazin-3(7H)-one (0.035 mmol) was reacted with TFA (1 mL) to afford the desired product (5 mg, 9% over three steps) as an orange solid. ESI MS m/z 452 [M+H]$^+$.

Following general procedure B, methyl 2-((3-benzyl-5-(3-((tert-butyldimethylsilyl)oxy)phenyl)pyrazin-2-yl)amino)-2-(diethoxyphosphoryl)acetate (130 mg, 0.22 mmol) was reacted with 4-fluorobenzaldehyde (32 mg, 0.26 mmol) to afford a mixture of the product and de-silylated product (110 mg) as a red black solid. ESI MS m/z 538, 424 [M+H]$^+$.

Step 2. 8-benzyl-6-(3-((tert-butyldimethylsilyl)oxy)phenyl)-2-(4-fluorobenzyl)imidazo[1,2-a]pyrazin-3(7H)-one (JRW-0785)

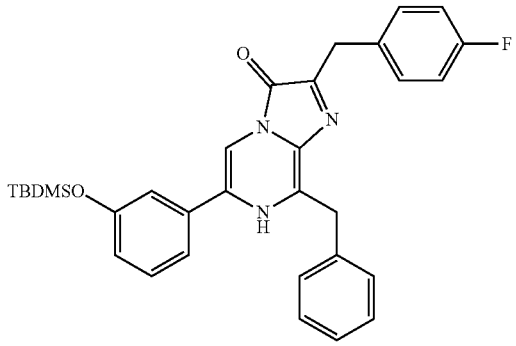 [SMILES: CC(C)(C)[Si](C)(C)Oc1cccc(-c2cn3c(=O)c(Cc4ccc(F)cc4)nc-3c(Cc3ccccc3)[nH]2)c1]

Following general procedure F, 8-benzyl-6-(3-((tert-butyldimethylsilyl)oxy)phenyl)-2-(4-fluorobenzylidene)imidazo[1,2-a]pyrazin-3(2H)-one (110 mg, 0.20 mmol) was reacted with sodium borohydride (39 mg, 1.0 mmol) to afford crude product (98 mg) as an orange foam. ESI MS m/z 540 [M+H]+.

Step 3. 8-benzyl-2-(4-fluorobenzyl)-6-(3-hydroxyphenyl)imidazo[1,2-a]pyrazin-3(7H)-one (JRW-0786)

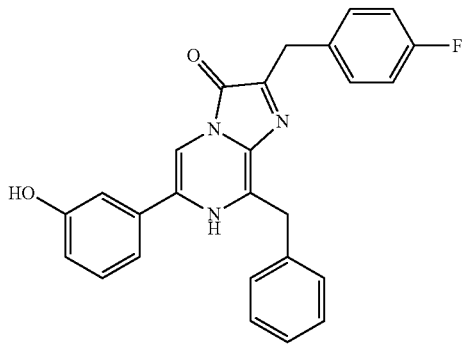 [SMILES: O=c1c(Cc2ccc(F)cc2)nc2c(Cc3ccccc3)[nH]c(-c3cccc(O)c3)cn1-2]

Following general procedure G, 8-benzyl-6-(3-((tert-butyldimethylsilyl)oxy)phenyl)-2-(4-fluorobenzyl)imidazo[1,2-a]pyrazin-3(7H)-one (98 mg, 0.18 mmol) was reacted with HCl (1 mL, 6M) to afford the desired product (50 mg, 54% over three steps) as an orange solid. ESI MS m/z 426 [M+H]+.

Example 5. 8-benzyl-6-(3-hydroxyphenyl)-2-(thiophen-2-ylmethyl)imidazo[1,2-a]pyrazin-3(7H)-one (JRW-1040)

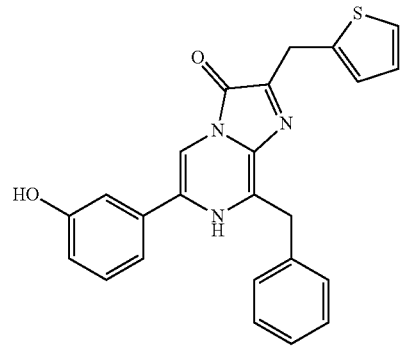 [SMILES: O=c1c(Cc2cccs2)nc2c(Cc3ccccc3)[nH]c(-c3cccc(O)c3)cn1-2]

Step 1. 8-benzyl-6-(3-((tert-butyldimethylsilyl)oxy)phenyl)-2-(thiophen-2-ylmethylene)imidazo[1,2-a]pyrazin-3(2H)-one (JRW-1038)

Following general procedure B, methyl 2-((3-benzyl-5-(3-((tert-butyldimethylsilyl)oxy)phenyl)pyrazin-2-yl)amino)-2-(diethoxyphosphoryl)acetate (110 mg, 0.18 mmol) was reacted with thiophene-2-carbaldehyde (25 mg, 0.22 mmol) to afford a crude product as a red black solid. ESI MS m/z 526 [M+H]+.

Step 2. 8-benzyl-6-(3-((tert-butyldimethylsilyl)oxy)phenyl)-2-(thiophen-2-ylmethyl)imidazo[1,2-a]pyrazin-3(7H)-one (JRW-1039)

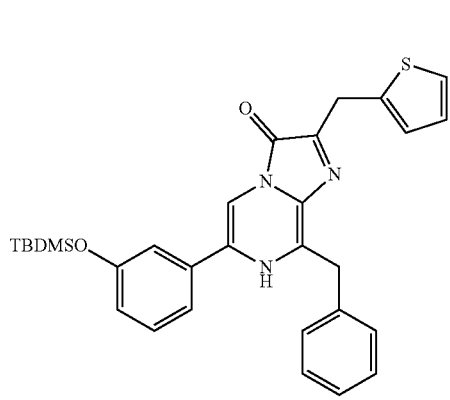 [SMILES: CC(C)(C)[Si](C)(C)Oc1cccc(-c2cn3c(=O)c(Cc4cccs4)nc-3c(Cc3ccccc3)[nH]2)c1]

Following general procedure F, 8-benzyl-6-(3-((tert-butyldimethylsilyl)oxy)phenyl)-2-(thiophen-2-ylmethylene)imidazo[1,2-a]pyrazin-3(2H)-one (0.18 mmol) was reacted with sodium borohydride (20 mg, 0.54 mmol) to afford the desired product (20 mg, 21%) as an orange foam. ESI MS m/z 528 [M+H]$^+$.

Step 3. 8-benzyl-6-(3-hydroxyphenyl)-2-(thiophen-2-ylmethyl)imidazo[1,2-a]pyrazin-3(7H)-one (JRW-1040)

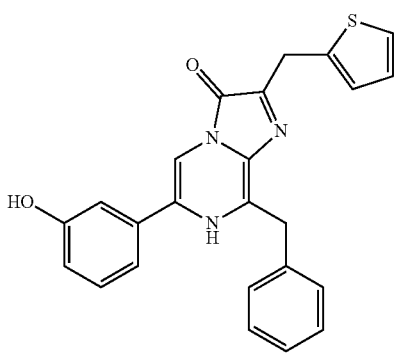 [SMILES: O=c1c(Cc2cccs2)nc2c(Cc3ccccc3)[nH]c(-c3cccc(O)c3)cn1-2]

Following general procedure G, 8-benzyl-6-(3-((tert-butyldimethylsilyl)oxy)phenyl)-2-(thiophen-2-ylmethyl)imidazo[1,2-a]pyrazin-3(7H)-one (20 mg, 0.038 mmol) was reacted with HCl (1 mL, 6M) to afford the desired product (9 mg, 60%) as a yellow solid. ESI MS m/z 414 [M+H]$^+$.

Example 6. 2,8-dibenzyl-6-(3-hydroxyphenyl)imidazo[1,2-a]pyrazin-3(7H)-one (JRW-1043)

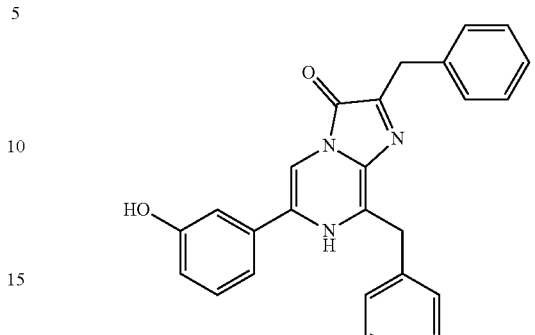

Step 1. 8-benzyl-2-benzylidene-6-(3-((tert-butyldimethylsilyl)oxy)phenyl)imidazo[1,2-a]pyrazin-3(2H)-one (JRW-1041)

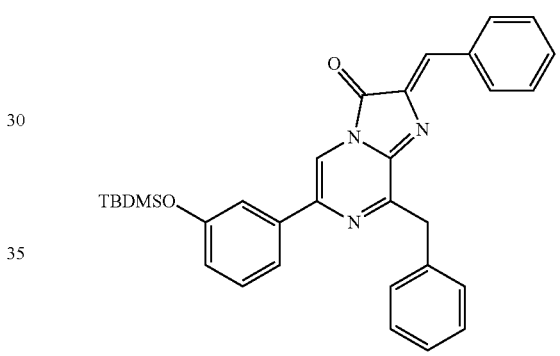

Following general procedure B, methyl 2-((3-benzyl-5-(3-((tert-butyldimethylsilyl)oxy)phenyl)pyrazin-2-yl)amino)-2-(diethoxyphosphoryl)acetate (100 mg, 0.16 mmol) was reacted with benzaldehyde (21 mg, 0.20 mmol) to afford a mixture of the product and de-silylated product as a red solid. ESI MS m/z 520, 406 [M+H]$^+$.

Step 2. 2,8-dibenzyl-6-(3-((tert-butyldimethylsilyl)oxy)phenyl)imidazo[1,2-a]pyrazin-3 (7H)-one (JRW-1042)

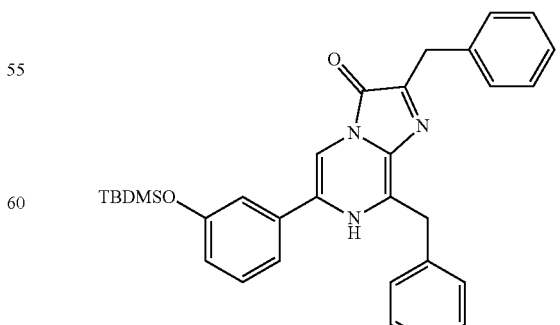

Following general procedure F, 8-benzyl-2-benzylidene-6-(3-((tert-butyldimethylsilyl)oxy)phenyl)imidazo[1,2-a]pyrazin-3(2H)-one (0.16 mmol) was reacted with sodium borohydride (31 mg, 0.83 mmol) to afford crude product as an orange foam. ESI MS m/z 522 [M+H]$^+$.

Step 3. 2,8-dibenzyl-6-(3-hydroxyphenyl)imidazo[1,2-a]pyrazin-3(7H)-one (JRW-1043)

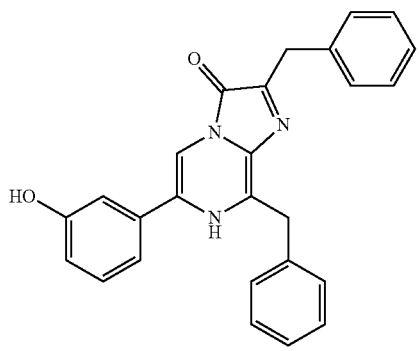 [SMILES: O=c1c(Cc2ccccc2)nc2c(Cc3ccccc3)[nH]c(-c3cccc(O)c3)cn1-2]

Following general procedure G, 2,8-dibenzyl-6-(3-((tert-butyldimethylsilyl)oxy)phenyl)imidazo[1,2-a]pyrazin-3(7H)-one (40 mg, 0.077 mmol) was reacted with HCl (1 mL, 6M) to afford the desired product (41 mg, 61% over three steps) as a yellow-orange solid. ESI MS m/z 408 [M+H]$^+$.

Example 7. 8-benzyl-6-(3-hydroxyphenyl)-2-(3-methoxybenzyl)imidazo[1,2-a]pyrazin-3(7H)-one (JRW-1047)

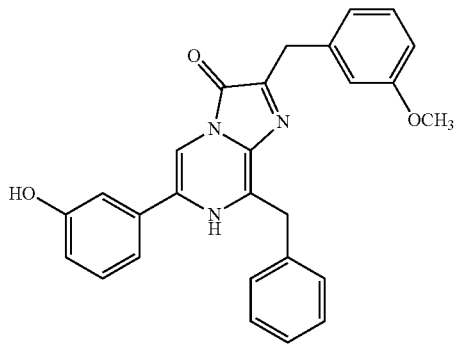 [SMILES: COc1cccc(Cc2nc3c(Cc4ccccc4)[nH]c(-c4cccc(O)c4)cn-3c2=O)c1]

Step 1. 8-benzyl-6-(3-((tert-butyldimethylsilyl)oxy)phenyl)-2-(3-methoxybenzylidene)imidazo[1,2-a]pyrazin-3(2H)-one (JRW-1045)

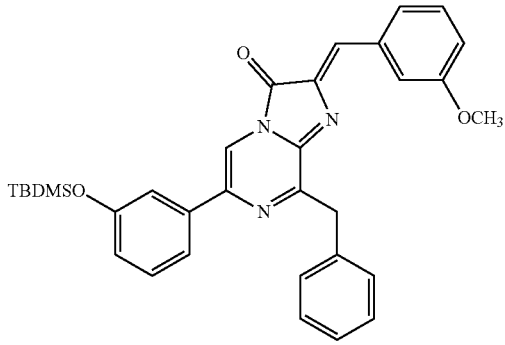 [SMILES: COc1cccc(/C=C2\N=C3C(Cc4ccccc4)=NC(c4cccc(O[Si](C)(C)C(C)(C)C)c4)=CN3C2=O)c1]

Following general procedure B, methyl 2-((3-benzyl-5-(3-((tert-butyldimethylsilyl)oxy)phenyl)pyrazin-2-yl)amino)-2-(diethoxyphosphoryl)acetate (125 mg, 0.21 mmol) was reacted with 3-methoxybenzaldehyde (34 mg, 0.25 mmol) to afford a mixture of the product and de-silylated product as a red solid. ESI MS m/z 550, 436 [M+H]$^+$.

Step 2. 8-benzyl-6-(3-((tert-butyldimethylsilyl)oxy)phenyl)-2-(3-methoxybenzyl)imidazo[1,2-a]pyrazin-3(7H)-one (JRW-1046)

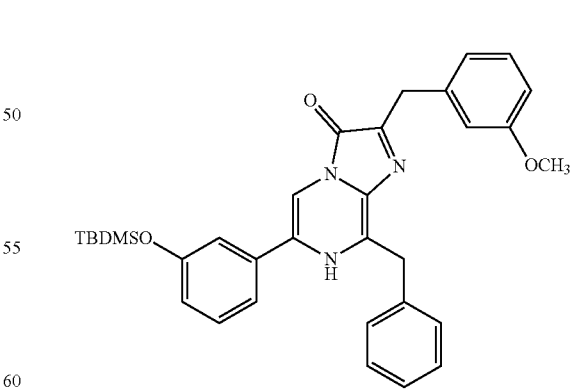

Following general procedure F, 8-benzyl-6-(3-((tert-butyldimethylsilyl)oxy)phenyl)-2-(3-methoxybenzylidene)imidazo[1,2-a]pyrazin-3(2H)-one (0.21 mmol) was reacted with sodium borohydride (38 mg, 1.0 mmol) to afford crude product as an orange foam. ESI MS m/z 552 [M+H]$^+$.

Step 3. 8-benzyl-6-(3-hydroxyphenyl)-2-(3-methoxybenzyl)imidazo[1,2-a]pyrazin-3 (7H)-one (JRW-1047)

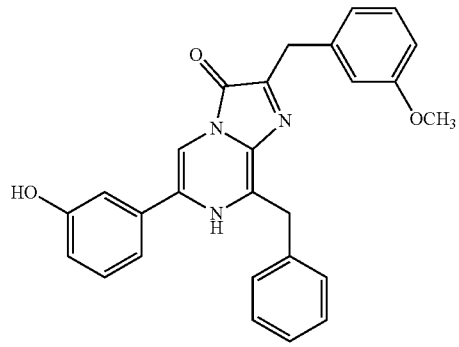 [SMILES: COc1cccc(Cc2nc3c(Cc4ccccc4)[nH]c(-c4cccc(O)c4)cn-3c2=O)c1]

Following general procedure G, 8-benzyl-6-(3-((tert-butyldimethylsilyl)oxy)phenyl)-2-(3-methoxybenzyl)imidazo[1,2-a]pyrazin-3(7H)-one (0.21 mmol) was reacted with HCl (1 mL, 6M) to afford the desired product (58 mg, 63% over three steps) as an orange solid. ESI MS m/z 438 [M+H]$^+$.

Example 8. 8-benzyl-6-(3-hydroxyphenyl)-2-(4-methoxybenzyl)imidazo[1,2-a]pyrazin-3(7H)-one (JRW-1052)

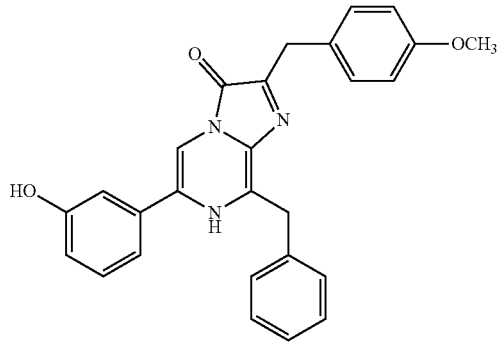 [SMILES: COc1ccc(Cc2nc3c(Cc4ccccc4)[nH]c(-c4cccc(O)c4)cn-3c2=O)cc1]

Step 1. 8-benzyl-6-(3-((tert-butyldimethylsilyl)oxy)phenyl)-2-(4-methoxybenzylidene)imidazo[1,2-a]pyrazin-3(2H)-one (JRW-1049)

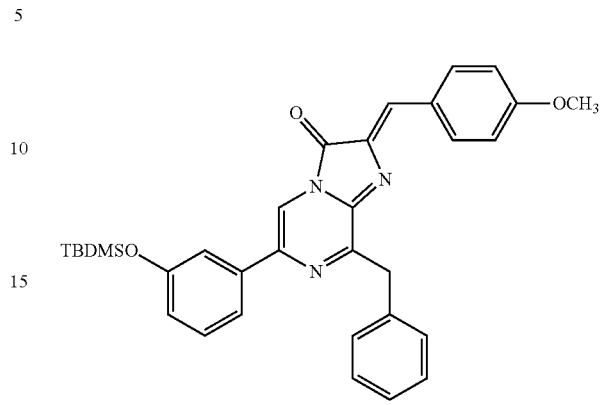

Following general procedure B, methyl 2-((3-benzyl-5-(3-((tert-butyldimethylsilyl)oxy)phenyl)pyrazin-2-yl)amino)-2-(diethoxyphosphoryl)acetate (100 mg, 0.16 mmol) was reacted with 4-methoxybenzaldehyde (27 mg, 0.20 mmol) to afford a mixture of the product and de-silylated product as a red solid. ESI MS m/z 550, 436 [M+H]$^+$.

Step 2. 8-benzyl-6-(3-((tert-butyldimethylsilyl)oxy)phenyl)-2-(4-methoxybenzyl)imidazo[1,2-a]pyrazin-3(7H)-one (JRW-1051)

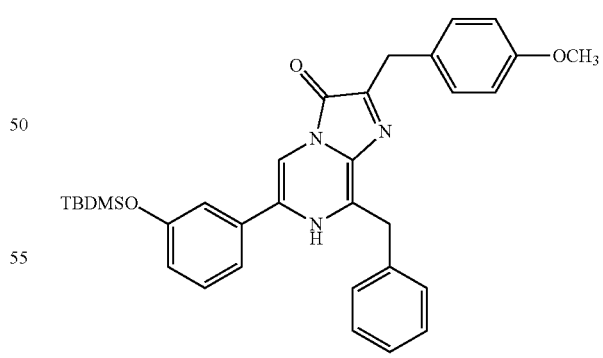

Following general procedure F, 8-benzyl-6-(3-((tert-butyldimethylsilyl)oxy)phenyl)-2-(4-methoxybenzylidene)imidazo[1,2-a]pyrazin-3(2H)-one (0.16 mmol) was reacted with sodium borohydride (31 mg, 0.83 mmol) to afford crude product as an orange solid. ESI MS m/z 552 [M+H]$^+$.

Step 3. 8-benzyl-6-(3-hydroxyphenyl)-2-(4-methoxybenzyl)imidazo[1,2-a]pyrazin-3(7H)-one (JRW-1052)

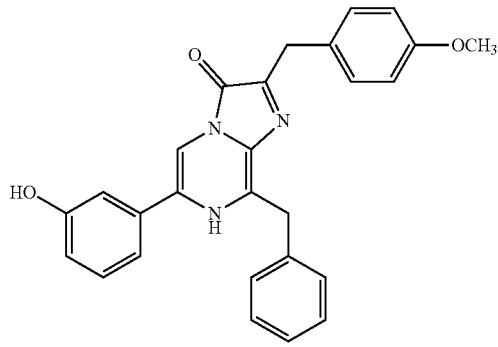 [SMILES: COc1ccc(Cc2nc3c(Cc4ccccc4)[nH]c(-c4cccc(O)c4)cn-3c2=O)cc1]

Following general procedure G, 8-benzyl-6-(3-((tert-butyldimethylsilyl)oxy)phenyl)-2-(4-methoxybenzyl)imidazo[1,2-a]pyrazin-3(7H)-one (0.16 mmol) was reacted with HCl (1 mL, 6M) to afford the desired product (41 mg, 57% over three steps) as an orange solid. ESI MS m/z 438 [M+H]$^+$.

Example 9. 8-benzyl-6-(3-hydroxyphenyl)-2-((5-methylfuran-2-yl)methyl)imidazo[1,2-a]pyrazin-3(7H)-one (JRW-1056)

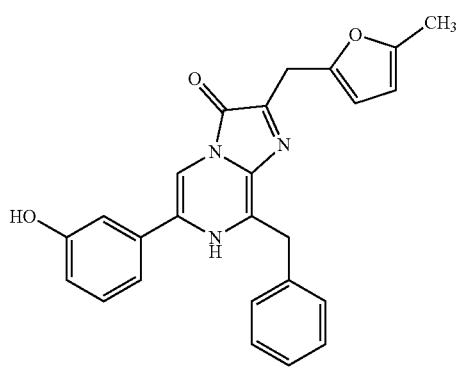 [SMILES: Cc1ccc(Cc2nc3c(Cc4ccccc4)[nH]c(-c4cccc(O)c4)cn-3c2=O)o1]

Step 1. 8-benzyl-6-(3-((tert-butyldimethylsilyl)oxy)phenyl)-2-((5-methylfuran-2-yl)methylene)imidazo[1,2-a]pyrazin-3(2H)-one (JRW-1054)

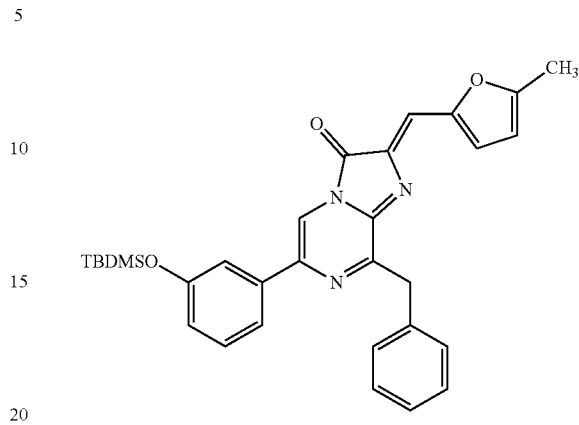

Following general procedure B, methyl 2-((3-benzyl-5-(3-((tert-butyldimethylsilyl)oxy)phenyl)pyrazin-2-yl)amino)-2-(diethoxyphosphoryl)acetate (100 mg, 0.16 mmol) was reacted with 5-methylfuran-2-carbaldehyde (22 mg, 0.20 mmol) to afford a mixture of the product and de-silylated product as a red solid. ESI MS m/z 524, 410 [M+H]$^+$.

Step 2. 8-benzyl-6-(3-((tert-butyldimethylsilyl)oxy)phenyl)-2-((5-methylfuran-2-yl)methyl)imidazo[1,2-a]pyrazin-3(7H)-one (JRW-1055)

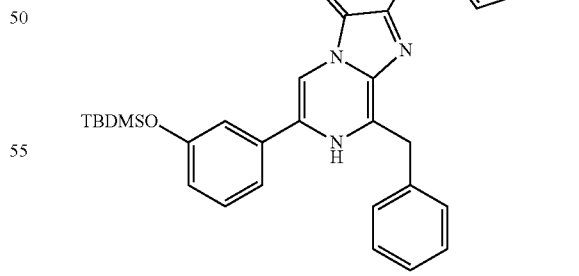

Following general procedure F, 8-benzyl-6-(3-((tert-butyldimethylsilyl)oxy)phenyl)-2-((5-methylfuran-2-yl)methylene)imidazo[1,2-a]pyrazin-3(2H)-one (0.16 mmol) was reacted with sodium borohydride (31 mg, 0.83 mmol) to afford crude product as a yellow solid. ESI MS m/z 526 [M+H]$^+$.

Step 3. 8-benzyl-6-(3-hydroxyphenyl)-2-((5-methyl-furan-2-yl)methyl)imidazo[1,2-a]pyrazin-3(7H)-one (JRW-1056)

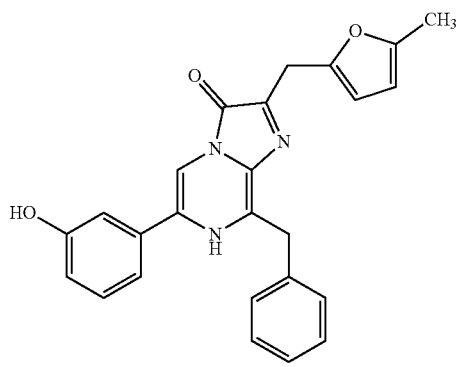 [SMILES: Cc1ccc(Cc2nc3c(Cc4ccccc4)[nH]c(-c4cccc(O)c4)cn-3c2=O)o1]

Following general procedure G, 8-benzyl-6-(3-((tert-butyldimethylsilyl)oxy)phenyl)-2-((5-methylfuran-2-yl)methyl)imidazo[1,2-a]pyrazin-3(7H)-one (0.16 mmol) was reacted with HCl (1 mL, 6M) to afford the desired product (17 mg, 25% over three steps) as an orange solid. ESI MS m/z 412 [M+H]$^+$.

Example 10. 8-benzyl-6-(3-hydroxyphenyl)-2-((5-(trifluoromethyl)furan-2-yl)methyl)imidazo[1,2-a]pyrazin-3(7H)-one (JRW-1180)

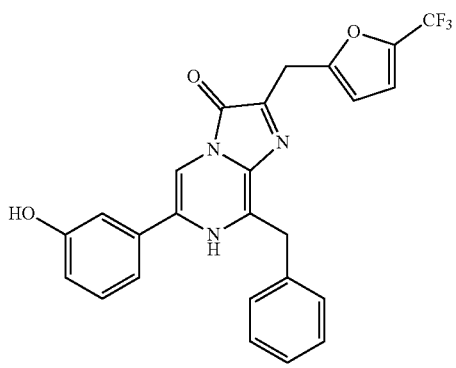 [SMILES: O=c1c(Cc2ccc(C(F)(F)F)o2)nc2c(Cc3ccccc3)[nH]c(-c3cccc(O)c3)cn1-2]

Step 1. Tert-butyl 2-((3-benzyl-5-(3-((tert-butyldimethylsilyl)oxy)phenyl)pyrazin-2-yl)amino)-2-(diethoxyphosphoryl)acetate (JRW-1165)

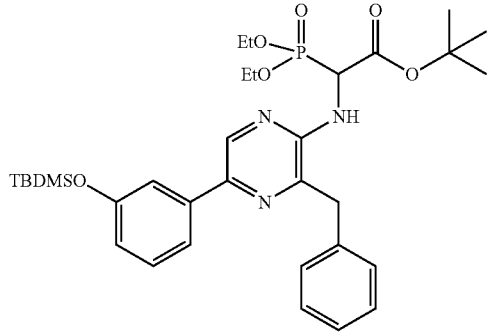 [SMILES: CCOP(=O)(OCC)C(Nc1ncc(-c2cccc(O[Si](C)(C)C(C)(C)C)c2)nc1Cc1ccccc1)C(=O)OC(C)(C)C]

Following general procedure A, 3-benzyl-5-(3-((tert-butyldimethylsilyl)oxy)phenyl)pyrazin-2-amine (410 mg, 1.05 mmol) was reacted with tert-butyl 2-diazo-2-(diethoxyphosphoryl)acetate (582 mg, 2.1 mmol) to afford the desired product (580 mg, 86%) as a brown solid. ESI MS m/z 642 [M+H]$^+$.

Step 2. Tert-butyl 2-((3-benzyl-5-(3-((tert-butyldimethylsilyl)oxy)phenyl)pyrazin-2-yl)amino)-3-(5-(trifluoromethyl)furan-2-yl)acrylate (JRW-1168)

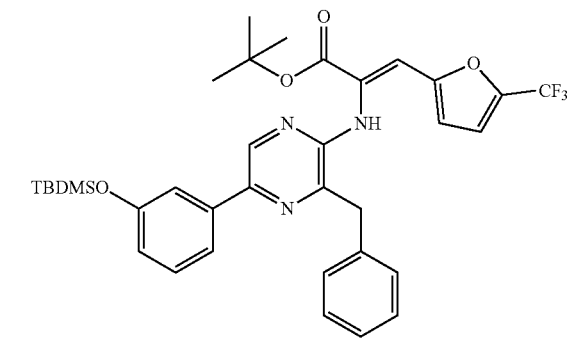 [SMILES: CC(C)(C)OC(=O)/C(=C/c1ccc(C(F)(F)F)o1)Nc1ncc(-c2cccc(O[Si](C)(C)C(C)(C)C)c2)nc1Cc1ccccc1]

Following general procedure B, tert-butyl 2-((3-benzyl-5-(3-((tert-butyldimethylsilyl)oxy)phenyl)pyrazin-2-yl)amino)-2-(diethoxyphosphoryl)acetate (250 mg, 0.39 mmol) was reacted with 5-trifluoromethylfuran-2-carbaldehyde (70 mg, 0.43 mmol) to afford the desired product (180 mg, 71%) as a purple foam. ESI MS m/z 652 [M+H]$^+$.

Step 3. Tert-butyl 2-((3-benzyl-5-(3-((tert-butyldimethylsilyl)oxy)phenyl)pyrazin-2-yl)amino)-3-(5-(trifluoromethyl)furan-2-yl)propanoate (JRW-1170)

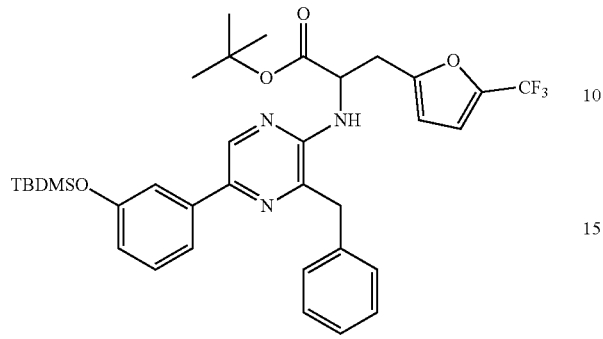

To a solution of tert-butyl 2-((3-benzyl-5-(3-((tert-butyldimethylsilyl)oxy)phenyl)pyrazin-2-yl)amino)-3-(5-(trifluoromethyl)furan-2-yl)acrylate (180 mg, 0.27 mmol) in ethanol (25 mL), Wilkinson's catalyst [chloridotris(triphenylphosphane)rhodium(I)] (25 mg, 0.027 mmol) was added. The solution was placed in a steel reaction vessel and charged with 80 psi hydrogen gas. The reaction stirred at rt for 48 h. The mixture was then filtered through celite, washed with ethanol, concentrated, and purified with silica gel chromatography to give the desired product (123 mg, 68%) as an orange oil. ESI MS m/z 654 [M+H]$^+$.

Step 4. 2-((3-benzyl-5-(3-((tert-butyldimethylsilyl)oxy)phenyl)pyrazin-2-yl)amino)-3-(5-(trifluoromethyl)furan-2-yl)propanoic acid (JRW-1176)

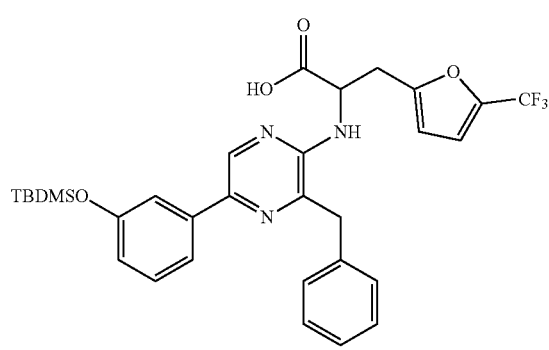 [SMILES: CC(C)(C)[Si](C)(C)Oc1cccc(-c2cnc(NC(Cc3ccc(C(F)(F)F)o3)C(=O)O)c(Cc3ccccc3)n2)c1]

Following general procedure D, tert-butyl 2-((3-benzyl-5-(3-((tert-butyldimethylsilyl)oxy)phenyl)pyrazin-2-yl)amino)-3-(5-(trifluoromethyl)furan-2-yl)propanoate (123 mg, 0.18 mmol) was reacted with TFA (1 mL) to afford crude product as an orange gel. ESI MS m/z 598 [M+H]$^+$.

Step 5. 8-benzyl-6-(3-((tert-butyldimethylsilyl)oxy)phenyl)-2-((5-(trifluoromethyl)furan-2-yl)methyl)imidazo[1,2-a]pyrazin-3(7H)-one (JRW-1178)

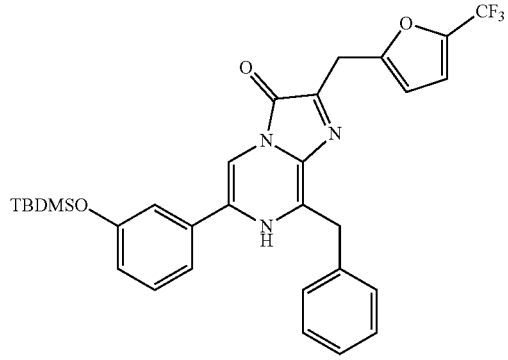 [SMILES: CC(C)(C)[Si](C)(C)Oc1cccc(-c2cn3c(=O)c(Cc4ccc(C(F)(F)F)o4)nc-3c(Cc3ccccc3)[nH]2)c1]

Following general procedure E, 2-((3-benzyl-5-(3-((tert-butyldimethylsilyl)oxy)phenyl)pyrazin-2-yl)amino)-3-(5-(trifluoromethyl)furan-2-yl)propanoic acid (0.18 mmol) was reacted with CDI (58 mg, 0.36 mmol) to afford the desired product (70 mg, 67%) as an orange foam. ESI MS m/z 579 [M+H]$^+$.

Step 6. 8-benzyl-6-(3-hydroxyphenyl)-2-((5-(trifluoromethyl)furan-2-yl)methyl)imidazo[1,2-a]pyrazin-3(7H)-one (JRW-1180)

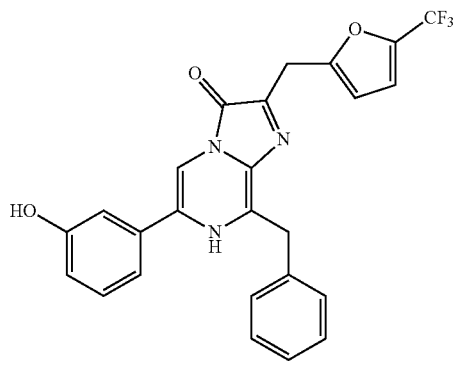 [SMILES: O=c1c(Cc2ccc(C(F)(F)F)o2)nc2c(Cc3ccccc3)[nH]c(-c3cccc(O)c3)cn1-2]

Following general procedure G, 8-benzyl-6-(3-((tert-butyldimethylsilyl)oxy)phenyl)-2-((5-(trifluoromethyl)furan-2-yl)methyl)imidazo[1,2-a]pyrazin-3(7H)-one (70 mg, 0.12 mmol) was reacted with HCl (1 mL, 6M) to afford the desired product (46 mg, 82%) as an orange solid. ESI MS m/z 465 [M+H]$^+$.

Example 11. 2-(furan-2-ylmethyl)-6-(3-hydroxyphenyl)-8-(3-methylbenzyl)imidazo[1,2-a]pyrazin-3(7H)-one (JRW-1368)

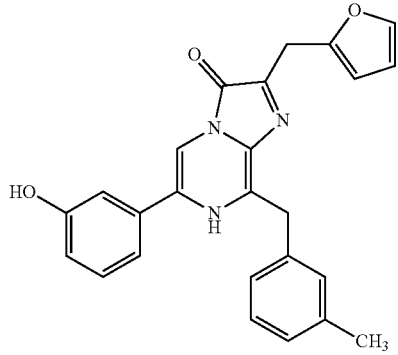

Step 1. 5-bromo-3-(3-methylbenzyl)pyrazin-2-amine (JRW-1341)

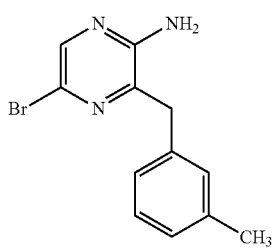 [SMILES: Cc1cccc(Cc2nc(Br)cnc2N)c1]

To a solution of 3,5-dibromopyrazin-2-amine (2.5 g, 9.9 mmol) in DMF/THF (1:1, 40 mL), bis(triphenylphosphine) palladium(II) dichloride (346 mg, 0.49 mmol) was added while purging with nitrogen. (3-Methylbenzyl)zinc(II) chloride (45 mL, 0.5 M in THF) was added and the reaction was heated to 50° C. for 1 h. The mixture was diluted with ethyl acetate and water, and the aqueous layer was extracted with ethyl acetate. The organic layers were combined, dried with sodium sulfate, filtered, concentrated, and purified with silica gel chromatography to give the desired product (2.45 g, 89%) as a yellow oil. ESI MS m/z 279 [M+H]$^+$.

Step 2. Tert-butyl 2-((5-bromo-3-(3-methylbenzyl)pyrazin-2-yl)amino)-2-(diethoxyphosphoryl)acetate (JRW-1348)

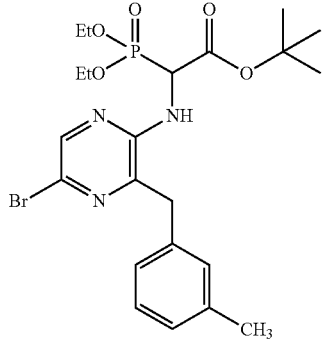 [SMILES: CCOP(=O)(OCC)C(Nc1ncc(Br)nc1Cc1cccc(C)c1)C(=O)OC(C)(C)C]

Following general procedure A, 5-bromo-3-(3-methylbenzyl)pyrazin-2-amine (2.45 g, 8.8 mmol) was reacted with tert-butyl 2-diazo-2-(diethoxyphosphoryl)acetate (3.68 g, 13.2 mmol) to afford the desired product (3.38 g, 72%) as an orange oil. ESI MS m/z 529 [M+H]$^+$.

Step 3. Tert-butyl 2-((5-bromo-3-(3-methylbenzyl)pyrazin-2-yl)amino)-3-(furan-2-yl)acrylate (JRW-1349)

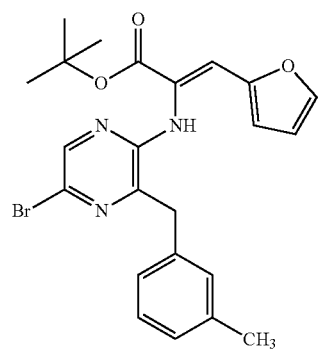 [SMILES: Cc1cccc(Cc2nc(Br)cnc2N/C(=C\c2ccco2)C(=O)OC(C)(C)C)c1]

Following general procedure B, tert-butyl 2-((5-bromo-3-(3-methylbenzyl)pyrazin-2-yl)amino)-2-(diethoxyphosphoryl)acetate (3.38 g, 6.4 mmol) was reacted with furfural (737 mg, 7.7 mmol) to afford the desired product (2.8 g, 93%) as an orange oil. ESI MS m/z 471 [M+H]$^+$.

Step 4. Tert-butyl 2-((5-(3-((tert-butyldimethyl silyl)oxy)phenyl)-3-(3-methylbenzyl)pyrazin-2-yl)amino)-3-(furan-2-yl)acrylate (JRW-1352)

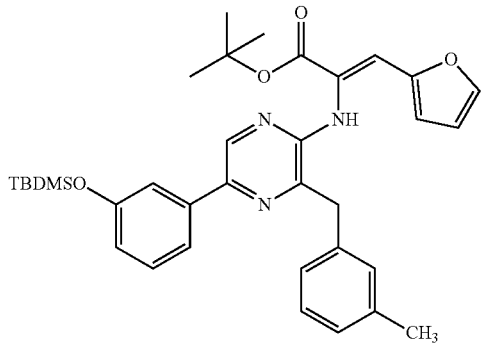 [SMILES: Cc1cccc(Cc2nc(-c3cccc(O[Si](C)(C)C(C)(C)C)c3)cnc2N/C(=C\c2ccco2)C(=O)OC(C)(C)C)c1]

To a solution of tert-butyl 2-((5-bromo-3-(3-methylbenzyl)pyrazin-2-yl)amino)-3-(furan-2-yl)acrylate (230 mg, 0.49 mmol) in dioxane (5 mL), (3-((tert-butyldimethylsilyl)oxy)phenyl)boronic acid (185 mg, 0.73 mmol) was added. While the solution was being purged with nitrogen, [1,1'-bis(diphenylphosphino)ferrocene]dichloropalladium(II) (39 mg, 0.049 mmol) and cesium carbonate (0.98 mL, 1M, 0.98 mmol) were added. The reaction stirred at 60° C. for 18 h. The mixture was diluted with ethyl acetate and water, and the aqueous layer was extracted with ethyl acetate. The organic layers were combined, dried with sodium sulfate, filtered, concentrated, and purified with silica gel chromatography to give crude product (241 mg) as a yellow oil. ESI MS m/z 598 [M+H]$^+$.

Step 5. 2-((5-(3-((tert-butyldimethylsilyl)oxy)phenyl)-3-(3-methylbenzyl)pyrazin-2-yl)amino)-3-(furan-2-yl)acrylic acid (JRW-1358)

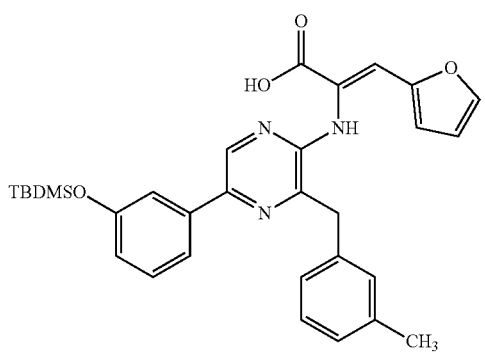 [SMILES: Cc1cccc(Cc2nc(-c3cccc(O[Si](C)(C)C(C)(C)C)c3)cnc2N/C(=C\c2ccco2)C(=O)O)c1]

Following general procedure D, tert-butyl 2-((5-(3-((tert-butyldimethylsilyl)oxy)phenyl)-3-(3-methylbenzyl)pyrazin-2-yl)amino)-3-(furan-2-yl)acrylate (240 mg, 0.40 mmol) was reacted with TFA (1 mL) to afford crude product as an orange-brown gel. ESI MS m/z 542 [M+H]$^+$.

Step 6. 6-(3-((tert-butyldimethylsilyl)oxy)phenyl)-2-(furan-2-ylmethylene)-8-(3-methylbenzyl)imidazo[1,2-a]pyrazin-3(2H)-one (JRW-1364)

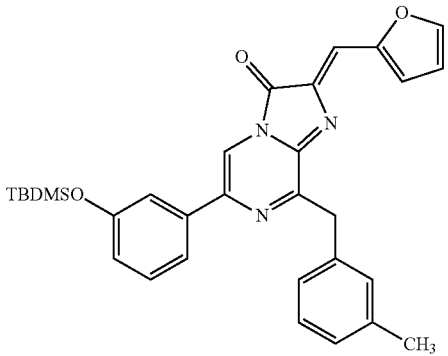 [SMILES: Cc1cccc(CC2=NC(c3cccc(O[Si](C)(C)C(C)(C)C)c3)=CN3C(=O)/C(=C/c4ccco4)N=C23)c1]

Following general procedure E, 2-((5-(3-((tert-butyldimethylsilyl)oxy)phenyl)-3-(3-methylbenzyl)pyrazin-2-yl)amino)-3-(furan-2-yl)acrylic acid (0.40 mmol) was reacted with CDI (130 mg, 0.80 mmol) to afford crude product as a red black solid. ESI MS m/z 524 [M+H]$^+$.

Step 7. 6-(3-((tert-butyldimethylsilyl)oxy)phenyl)-2-(furan-2-ylmethyl)-8-(3-methylbenzyl)imidazo[1,2-a]pyrazin-3(7H)-one (JRW-1366)

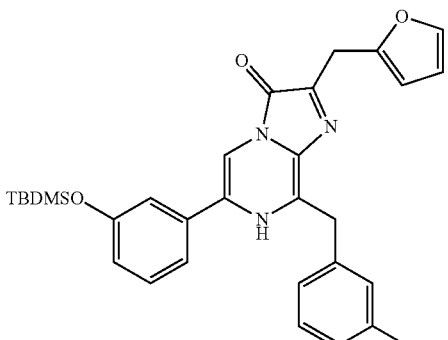

Following general procedure F, 6-(3-((tert-butyldimethylsilyl)oxy)phenyl)-2-(furan-2-ylmethylene)-8-(3-methylbenzyl)imidazo[1,2-a]pyrazin-3(2H)-one (0.40 mmol) was reacted with sodium borohydride (45 mg, 1.2 mmol) to afford the desired product (160 mg, 75% over two steps) as an orange solid. ESI MS m/z 526 [M+H]$^+$.

Step 8. 2-(furan-2-ylmethyl)-6-(3-hydroxyphenyl)-
8-(3-methylbenzyl)imidazo[1,2-a]pyrazin-3(7H)-one
(JRW-1368)

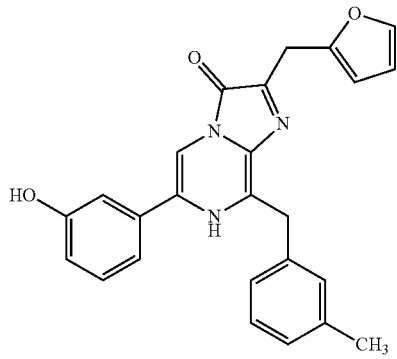

Following general procedure G, 6-(3-((tert-butyldimethylsilyl)oxy)phenyl)-2-(furan-2-ylmethyl)-8-(3-methylbenzyl)imidazo[1,2-a]pyrazin-3(7H)-one (160 mg, 0.30 mmol) was reacted with HCl (1 mL, 6M) to afford the desired product (83 mg, 66%) as an orange solid. ESI MS m/z 412 [M+H]⁺.

Example 12. 6-(2-fluoro-3-hydroxyphenyl)-2-(furan-2-ylmethyl)-8-(3-methylbenzyl)imidazo[1,2-a]pyrazin-3(7H)-one (JRW-1370)

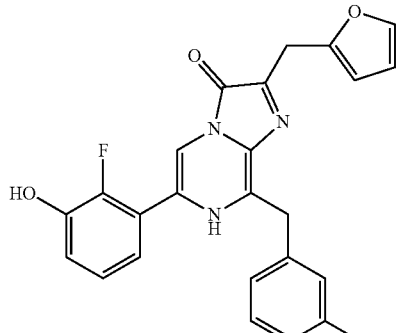

Step 1. Tert-butyl 2-((5-(3-((tert-butyldimethylsilyl)oxy)-2-fluorophenyl)-3-(3-methylbenzyl)pyrazin-2-yl)amino)-3-(furan-2-yl)acrylate (JRW-1353)

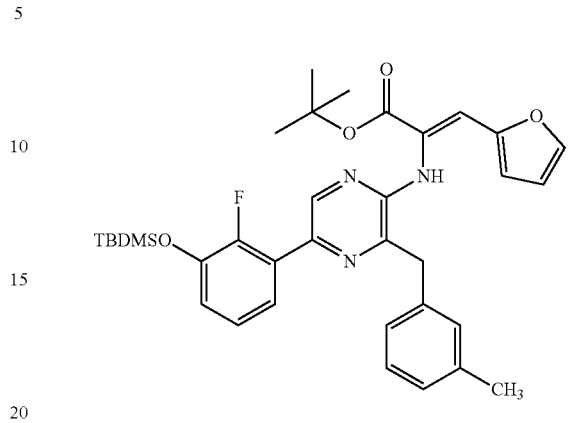

To a solution of tert-butyl 2-((5-bromo-3-(3-methylbenzyl)pyrazin-2-yl)amino)-3-(furan-2-yl)acrylate (200 mg, 0.43 mmol) in dioxane (5 mL), (3-((tert-butyldimethylsilyl)oxy)-2-fluorophenyl)boronic acid (172 mg, 0.64 mmol) was added. While the solution was being purged with nitrogen, [1,1'-bis(diphenylphosphino)ferrocene]dichloropalladium (II) (34 mg, 0.043 mmol) and cesium carbonate (0.85 mL, 1M, 0.85 mmol) were added. The reaction stirred at 60° C. for 18 h. The mixture was diluted with ethyl acetate and water, and the aqueous layer was extracted with ethyl acetate. The organic layers were combined, dried with sodium sulfate, filtered, concentrated, and purified with silica gel chromatography to give crude product (210 mg, 80%) as a yellow foam. ESI MS m/z 616 [M+H]⁺.

Step 2. 2-((5-(3-((tert-butyldimethylsilyl)oxy)-2-fluorophenyl)-3-(3-methylbenzyl)pyrazin-2-yl)amino)-3-(furan-2-yl)acrylic acid (JRW-1359)

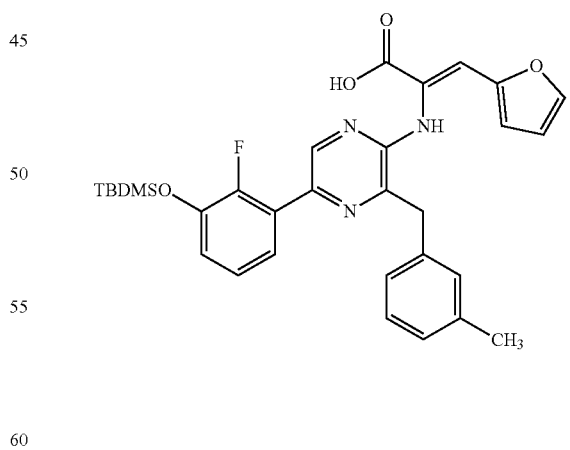

Following general procedure D, tert-butyl 2-((5-(3-((tert-butyldimethylsilyl)oxy)-2-fluorophenyl)-3-(3-methylbenzyl)pyrazin-2-yl)amino)-3-(furan-2-yl)acrylate (210 mg, 0.34 mmol) was reacted with TFA (1 mL) to afford crude product as a brown oil. ESI MS m/z 560 [M+H]⁺.

Step 3. 6-(3-((tert-butyldimethylsilyl)oxy)-2-fluorophenyl)-2-(furan-2-ylmethylene)-8-(3-methylbenzyl)imidazo[1,2-a]pyrazin-3(2H)-one (JRW-1367)

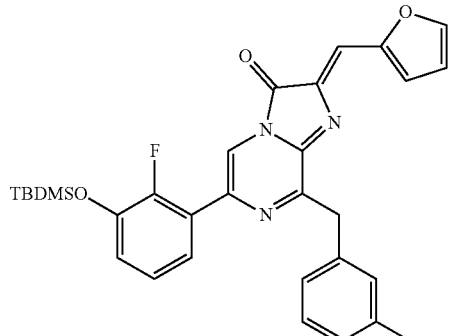

Following general procedure E, 2-((5-(3-((tert-butyldimethylsilyl)oxy)-2-fluorophenyl)-3-(3-methylbenzyl)pyrazin-2-yl)amino)-3-(furan-2-yl)acrylic acid (0.34 mmol) was reacted with CDI (110 mg, 0.68 mmol) to afford crude product as a red black solid. ESI MS m/z 542 [M+H]$^+$.

Step 4. 6-(3-((tert-butyldimethylsilyl)oxy)-2-fluorophenyl)-2-(furan-2-ylmethyl)-8-(3-methylbenzyl)imidazo[1,2-a]pyrazin-3(7H)-one (JRW-1369)

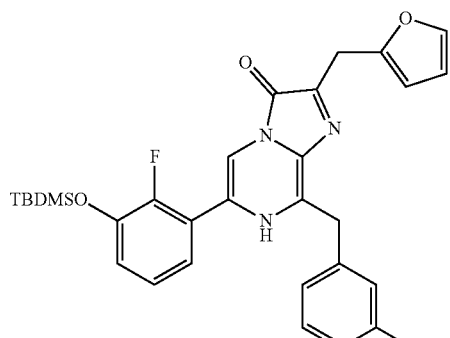

Following general procedure F, 6-(3-((tert-butyldimethylsilyl)oxy)-2-fluorophenyl)-2-(furan-2-ylmethylene)-8-(3-methylbenzyl)imidazo[1,2-a]pyrazin-3(2H)-one (0.34 mmol) was reacted with sodium borohydride (38 mg, 1.0 mmol) to afford crude product as an orange solid. ESI MS m/z 544 [M+H]$^+$.

Step 5. 6-(2-fluoro-3-hydroxyphenyl)-2-(furan-2-ylmethyl)-8-(3-methylbenzyl)imidazo[1,2-a]pyrazin-3(7H)-one (JRW-1370)

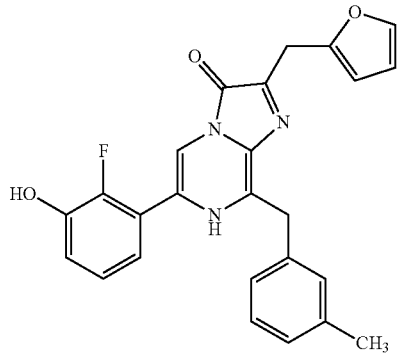 [SMILES: Cc1cccc(Cc2[nH]c(-c3cccc(O)c3F)cn3c(=O)c(Cc4ccco4)nc2-3)c1]

Following general procedure G, 6-(3-((tert-butyldimethylsilyl)oxy)-2-fluorophenyl)-2-(furan-2-ylmethyl)-8-(3-methylbenzyl)imidazo[1,2-a]pyrazin-3(7H)-one (0.34 mmol) was reacted with HCl (1 mL, 6M) to afford the desired product (88 mg, 60% over four steps) as an orange solid. ESI MS m/z 430 [M+H]$^+$.

Example 13. 8-benzyl-6-(2-fluoro-3-hydroxyphenyl)-2-(furan-2-ylmethyl)imidazo[1,2-a]pyrazin-3(7H)-one (JRW-1404)

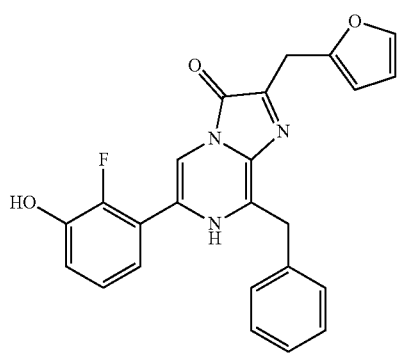

Step 1. Tert-butyl 2-((3-benzyl-5-bromopyrazin-2-yl)amino)-2-(diethoxyphosphoryl)acetate (JRW-1350)

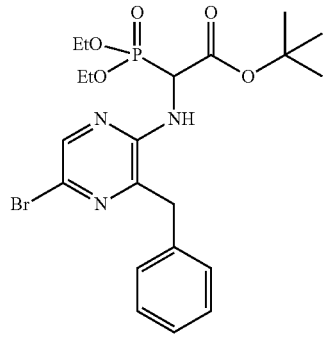 [SMILES: CCOP(=O)(OCC)C(Nc1ncc(Br)nc1Cc1ccccc1)C(=O)OC(C)(C)C]

Following general procedure A, 5-bromo-3-(3-methylbenzyl)pyrazin-2-amine (1.0 g, 3.8 mmol) was reacted with tert-butyl 2-diazo-2-(diethoxyphosphoryl)acetate (1.26 g, 4.5 mmol) to afford the desired product (1.7 g, 87%) as a brown oil. ESI MS m/z 514 [M+H]$^+$.

Step 2. Tert-butyl (Z)-2-((3-benzyl-5-bromopyrazin-2-yl)amino)-3-(furan-2-yl)acrylate (JRW-1372)

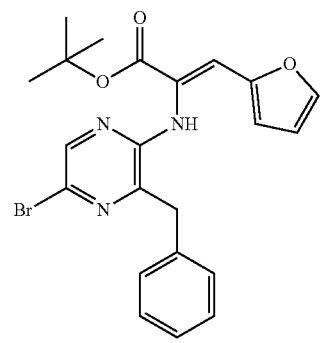 [SMILES: CC(C)(C)OC(=O)/C(=C/c1ccco1)Nc1ncc(Br)nc1Cc1ccccc1]

Following general procedure B, tert-butyl 2-((3-benzyl-5-bromopyrazin-2-yl)amino)-2-(diethoxyphosphoryl)acetate (1.1 g, 3.3 mmol) was reacted with furfural (0.47 g, 5.0 mmol) to afford the desired product (1.3 g, 74%) as an orange oil. ESI MS m/z 456 [M+H]$^+$.

Step 3. Tert-butyl (Z)-2-((3-benzyl-5-(3-((tert-butyldimethylsilyl)oxy)-2-fluorophenyl)pyrazin-2-yl)amino)-3-(furan-2-yl)acrylate (JRW-1394)

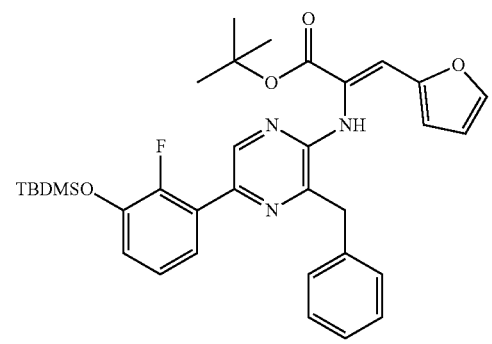

Following general procedure C, tert-butyl (Z)-2-((3-benzyl-5-bromopyrazin-2-yl)amino)-3-(furan-2-yl)acrylate (0.20 g, 0.44 mmol) was reacted with (3-((tert-butyldimethylsilyl)oxy)-2-fluorophenyl)boronic acid (0.18 g, 0.66 mmol) to afford the desired product (0.16 g, 59%) as a yellow foam. ESI MS m/z 602 [M+H]$^+$.

Step 4. (Z)-2-((3-benzyl-5-(3-((tert-butyldimethylsilyl)oxy)-2-fluorophenyl)pyrazin-2-yl)amino)-3-(furan-2-yl)acrylic acid (JRW-1398)

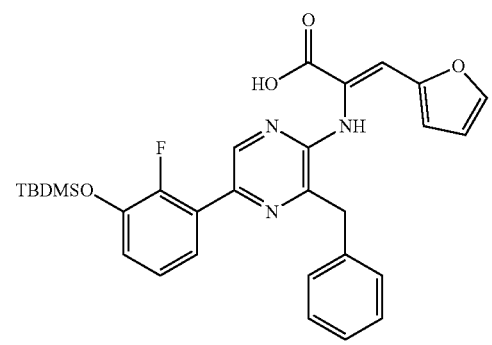

Following general procedure D, tert-butyl (Z)-2-((3-benzyl-5-(3-((tert-butyldimethylsilyl)oxy)-2-fluorophenyl)pyrazin-2-yl)amino)-3-(furan-2-yl)acrylate (0.16 g, 0.26 mmol) was reacted with trifluoroacetic acid (1 mL) to afford the crude product as a brown oil. ESI MS m/z 546 [M+H]$^+$.

Step 5. (Z)-8-benzyl-6-(3-((tert-butyldimethylsilyl)oxy)-2-fluorophenyl)-2-(furan-2-ylmethylene)imidazo[1,2-a]pyrazin-3(2H)-one (JRW-1400)

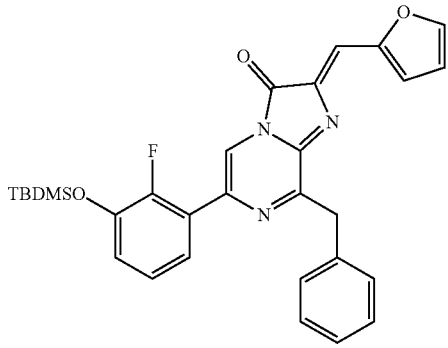 [SMILES: CC(C)(C)[Si](C)(C)Oc1cccc(C2=CN3C(=O)/C(=C/c4ccco4)N=C3C(Cc3ccccc3)=N2)c1F]

Following general procedure E, (Z)-2-((3-benzyl-5-(3-((tert-butyldimethylsilyl)oxy)-2-fluorophenyl)pyrazin-2-yl)amino)-3-(furan-2-yl)acrylic acid (0.26 mmol) was reacted with di(1H-imidazol-1-yl)methanone (0.084 g, 0.52 mmol) to afford the crude product as a red brown solid. ESI MS m/z 528 [M+H]$^+$.

Step 6. 8-benzyl-6-(3-((tert-butyldimethylsilyl)oxy)-2-fluorophenyl)-2-(furan-2-ylmethyl)imidazo[1,2-a]pyrazin-3(7H)-one (JRW-1402)

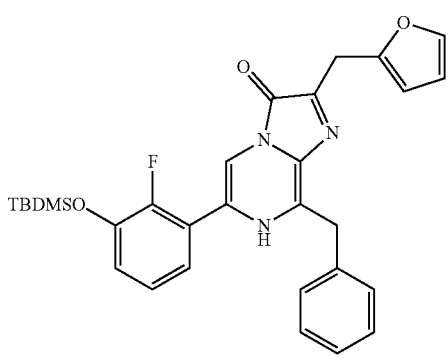 [SMILES: CC(C)(C)[Si](C)(C)Oc1cccc(-c2cn3c(=O)c(Cc4ccco4)nc-3c(Cc3ccccc3)[nH]2)c1F]

Following general procedure F, (Z)-8-benzyl-6-(3-((tert-butyldimethylsilyl)oxy)-2-fluorophenyl)-2-(furan-2-ylmethylene)imidazo[1,2-a]pyrazin-3(2H)-one (0.26 mmol) was reacted with sodium borohydride (0.049 g, 1.3 mmol) to afford the crude product as a brown foam. ESI MS m/z 530 [M+H]$^+$.

Step 7. 8-benzyl-6-(2-fluoro-3-hydroxyphenyl)-2-(furan-2-ylmethyl)imidazo[1,2-a]pyrazin-3(7H)-one (JRW-1404)

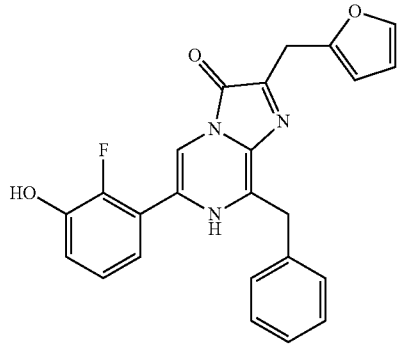

Following general procedure G, 8-benzyl-6-(3-((tert-butyldimethylsilyl)oxy)-2-fluorophenyl)-2-(furan-2-ylmethyl)imidazo[1,2-a]pyrazin-3(7H)-one (0.26 mmol) was reacted with HCl (1 mL, 6M) to afford the desired product (0.071 g, 65% over 4 steps) as an orange brown foam. $^1$H NMR (400 MHz, Methanol-d4) δ 7.72 (s, 1H), 7.47-7.38 (m, 3H), 7.36-7.29 (m, 2H), 7.29-7.22 (m, 1H), 7.16-7.01 (m, 3H), 6.34 (dd, J=3.2, 1.9 Hz, 1H), 6.13 (dd, J=3.2, 1.0 Hz, 1H), 4.42 (s, 2H), 4.22 (s, 2H); ESI MS m/z 416 [M+H]$^+$.

Example 14. 8-benzyl-6-(2-fluoro-5-hydroxyphenyl)-2-(furan-2-ylmethyl)imidazo[1,2-a]pyrazin-3(7H)-one (JRW-1405)

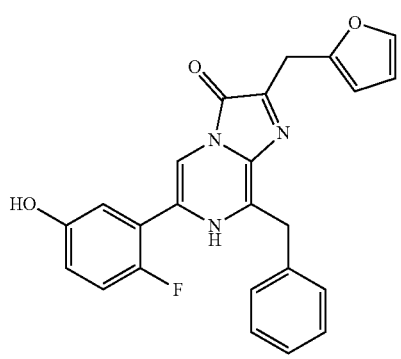 [SMILES: O=c1c(Cc2ccco2)nc2c(Cc3ccccc3)[nH]c(-c3cc(O)ccc3F)cn1-2]

Step 1. Tert-butyl (Z)-2-((3-benzyl-5-(5-((tert-butyldimethylsilyl)oxy)-2-fluorophenyl)pyrazin-2-yl)amino)-3-(furan-2-yl)acrylate (JRW-1395)

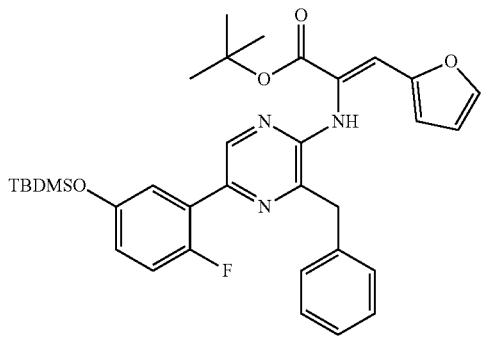 [SMILES: CC(C)(C)OC(=O)/C(=C/c1ccco1)Nc1ncc(-c2cc(O[Si](C)(C)C(C)(C)C)ccc2F)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with (5-((tert-butyldimethylsilyl)oxy)-2-fluorophenyl)boronic acid (0.18 g, 0.66 mmol) to afford the desired product (0.18 g, 67%) as a yellow foam. ESI MS m/z 602 [M+H]$^+$.

Step 2. (Z)-2-((3-benzyl-5-(5-((tert-butyldimethylsilyl)oxy)-2-fluorophenyl)pyrazin-2-yl)amino)-3-(furan-2-yl)acrylic acid (JRW-1399)

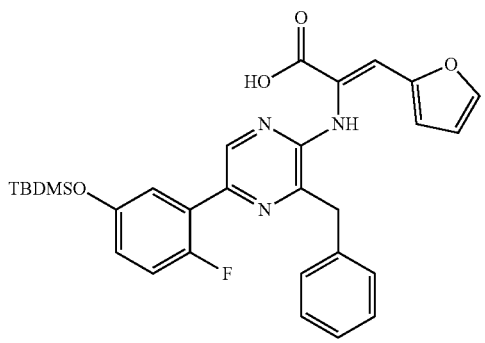 [SMILES: CC(C)(C)[Si](C)(C)Oc1ccc(F)c(-c2cnc(N/C(=C\c3ccco3)C(=O)O)c(Cc3ccccc3)n2)c1]

Following general procedure D, tert-butyl (Z)-2-((3-benzyl-5-(5-((tert-butyldimethylsilyl)oxy)-2-fluorophenyl)pyrazin-2-yl)amino)-3-(furan-2-yl)acrylate (0.18 g, 0.29 mmol) was reacted with trifluoroacetic acid (1 mL) to afford the crude product as a brown oil. ESI MS m/z 546 [M+H]$^+$.

Step 3. (Z)-8-benzyl-6-(5-((tert-butyldimethylsilyl)oxy)-2-fluorophenyl)-2-(furan-2-ylmethylene)imidazo[1,2-a]pyrazin-3(2H)-one (JRW-1401)

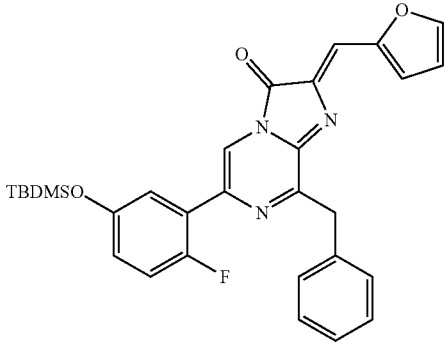 [SMILES: CC(C)(C)[Si](C)(C)Oc1ccc(F)c(C2=CN3C(=O)/C(=C/c4ccco4)N=C3C(Cc3ccccc3)=N2)c1]

Following general procedure E, (Z)-2-((3-benzyl-5-((tert-butyldimethylsilyl)oxy)-2-fluorophenyl)pyrazin-2-yl)amino)-3-(furan-2-yl)acrylic acid (0.29 mmol) was reacted with di(1H-imidazol-1-yl)methanone (0.094 g, 0.58 mmol) to afford the crude product as a black purple solid. ESI MS m/z 528 [M+H]$^+$.

Step 4. 8-benzyl-6-(5-((tert-butyldimethylsilyl)oxy)-2-fluorophenyl)-2-(furan-2-ylmethyl)imidazo[1,2-a]pyrazin-3(7H)-one (JRW-1403)

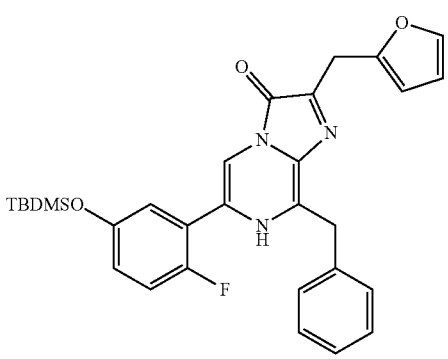 [SMILES: CC(C)(C)[Si](C)(C)Oc1ccc(F)c(-c2cn3c(=O)c(Cc4ccco4)nc-3c(Cc3ccccc3)[nH]2)c1]

Following general procedure F, (Z)-8-benzyl-6-(5-((tert-butyldimethylsilyl)oxy)-2-fluorophenyl)-2-(furan-2-ylmethylene)imidazo[1,2-a]pyrazin-3(2H)-one (0.29 mmol) was reacted with sodium borohydride (0.054 g, 1.4 mmol) to afford the crude product as an orange brown foam. ESI MS m/z 530 [M+H]$^+$.

Step 5. 8-benzyl-6-(2-fluoro-5-hydroxyphenyl)-2-(furan-2-ylmethyl)imidazo[1,2-a]pyrazin-3(7H)-one (JRW-1405)

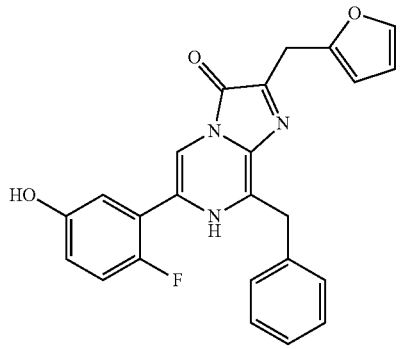 [SMILES: O=c1c(Cc2ccco2)nc2c(Cc3ccccc3)[nH]c(-c3cc(O)ccc3F)cn1-2]

Following general procedure G, 8-benzyl-6-(5-((tert-butyldimethylsilyl)oxy)-2-fluorophenyl)-2-(furan-2-ylmethyl)imidazo[1,2-a]pyrazin-3(7H)-one (0.29 mmol) was reacted with HCl (1 mL, 6M) to afford the desired product (0.083 g, 69% over 4 steps) as a brown orange foam. $^1$H NMR (400 MHz, Methanol-d4) δ 7.49-7.37 (m, 3H), 7.37-7.21 (m, 3H), 7.16-6.99 (m, 2H), 6.94-6.85 (m, 1H), 6.34 (dd, J=3.2, 1.9 Hz, 1H), 6.19-6.06 (m, 1H), 4.42 (s, 2H), 4.21 (s, 2H); ESI MS m/z 416 [M+H]$^+$.

Example 15. 6-(5-amino-2-fluorophenyl)-8-benzyl-2-(furan-2-ylmethyl)imidazo[1,2-a]pyrazin-3(7H)-one (JRW-1411)

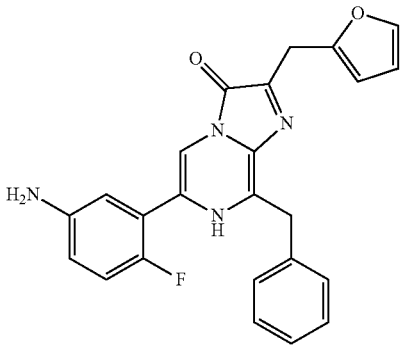 [SMILES: Nc1ccc(F)c(-c2cn3c(=O)c(Cc4ccco4)nc-3c(Cc3ccccc3)[nH]2)c1]

Step 1. Tert-butyl (Z)-2-((3-benzyl-5-(5-(((tert-butoxycarbonyl)amino)-2-fluorophenyl)pyrazin-2-yl)amino)-3-(furan-2-yl)acrylate (JRW-1406)

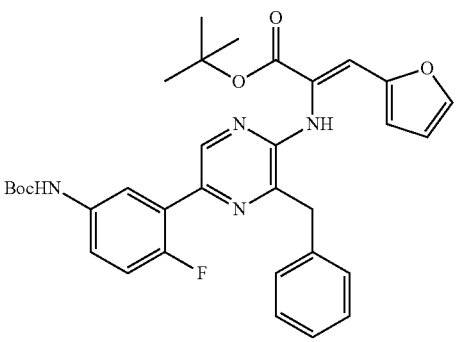 [SMILES: CC(C)(C)OC(=O)Nc1ccc(F)c(-c2cnc(N/C(=C\c3ccco3)C(=O)OC(C)(C)C)c(Cc3ccccc3)n2)c1]

Following general procedure C, tert-butyl (Z)-2-((3-benzyl-5-bromopyrazin-2-yl)amino)-3-(furan-2-yl)acrylate (0.25 g, 0.55 mmol) was reacted with (5-((tert-butoxycarbonyl)amino)-2-fluorophenyl)boronic acid (0.21 g, 0.82 mmol) to afford the desired product (0.30 g, 94%) as a light yellow foam. ESI MS m/z 587 [M+H]$^+$.

Step 2. (Z)-2-((5-(5-amino-2-fluorophenyl)-3-benzylpyrazin-2-yl)amino)-3-(furan-2-yl)acrylic acid (JRW-1408)

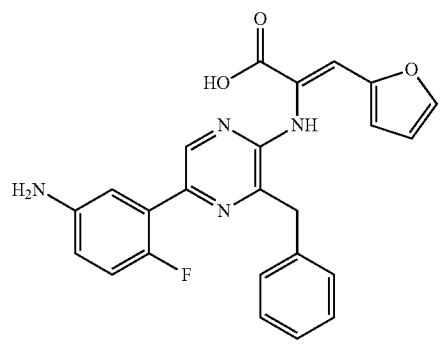 [SMILES: Nc1ccc(F)c(-c2cnc(N/C(=C\c3ccco3)C(=O)O)c(Cc3ccccc3)n2)c1]

Following general procedure D, tert-butyl (Z)-2-((3-benzyl-5-(5-((tert-butoxycarbonyl)amino)-2-fluorophenyl)pyrazin-2-yl)amino)-3-(furan-2-yl)acrylate (0.30 g, 0.51 mmol) was reacted with trifluoroacetic acid (1 mL) to afford the crude product as a black green solid. ESI MS m/z 431 [M+H]$^+$.

Step 3. (Z)-6-(5-amino-2-fluorophenyl)-8-benzyl-2-(furan-2-ylmethylene)imidazo[1,2-a]pyrazin-3(2H)-one (JRW-1410)

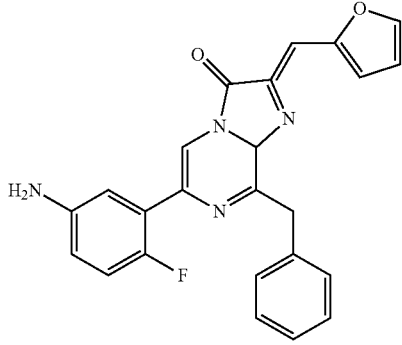

Following general procedure E, (Z)-2-((5-(5-amino-2-fluorophenyl)-3-benzylpyrazin-2-yl)amino)-3-(furan-2-yl)acrylic acid (0.51 mmol) was reacted with di(1H-imidazol-1-yl)methanone (0.25 g, 1.5 mmol) to afford the crude product as a red black solid. ESI MS m/z 413 [M+H]⁺.

Step 4. 6-(5-amino-2-fluorophenyl)-8-benzyl-2-(furan-2-ylmethyl)imidazo[1,2-a]pyrazin-3(7H)-one (JRW-1411)

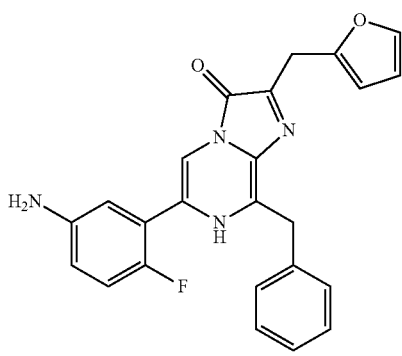 [SMILES: Nc1ccc(F)c(-c2cn3c(=O)c(Cc4ccco4)nc-3c(Cc3ccccc3)[nH]2)c1]

Following general procedure F, (Z)-6-(5-amino-2-fluorophenyl)-8-benzyl-2-(furan-2-ylmethylene)imidazo[1,2-a]pyrazin-3(2H)-one (0.51 mmol) was reacted with sodium borohydride (0.058 g, 1.5 mmol) to afford the desired product (0.006 g, 2% over three steps) as an orange solid. ¹H NMR (400 MHz, Methanol-d4) δ 7.70 (s, 1H), 7.47-7.36 (m, 3H), 7.36-7.19 (m, 4H), 7.07-6.87 (m, 2H), 6.84-6.77 (m, 1H), 6.34 (dd, J=3.2, 1.9 Hz, 1H), 6.12 (dd, J=3.2, 1.0 Hz, 1H), 4.41 (s, 2H), 4.21 (s, 2H); ESI MS m/z 415 [M+H]⁺.

Example 16. 8-benzyl-2-(furan-2-ylmethyl)-6-(3-nitrophenyl)imidazo[1,2-a]pyrazin-3(7H)-one (JRW-1424)

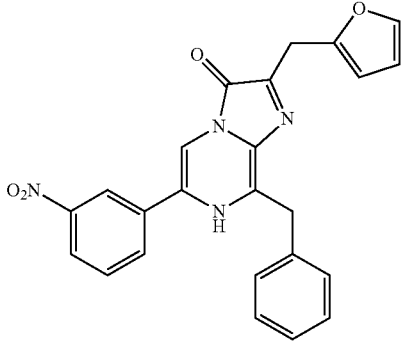

Step 1. Tert-butyl (Z)-2-((3-benzyl-5-(3-nitrophenyl)pyrazin-2-yl)amino)-3-(furan-2-yl)acrylate (JRW-1417)

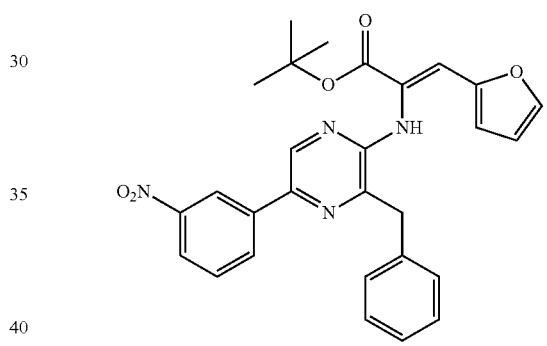

Following general procedure C, tert-butyl (Z)-2-((3-benzyl-5-bromopyrazin-2-yl)amino)-3-(furan-2-yl)acrylate (0.34 g, 0.74 mmol) was reacted with (3-nitrophenyl)boronic acid (0.19 g, 1.1 mmol) to afford the desired product (0.37 g, 99%) as an orange solid. ESI MS m/z 499 [M+H]⁺.

Step 2. (Z)-2-((3-benzyl-5-(3-nitrophenyl)pyrazin-2-yl)amino)-3-(furan-2-yl)acrylic acid (JRW-1421)

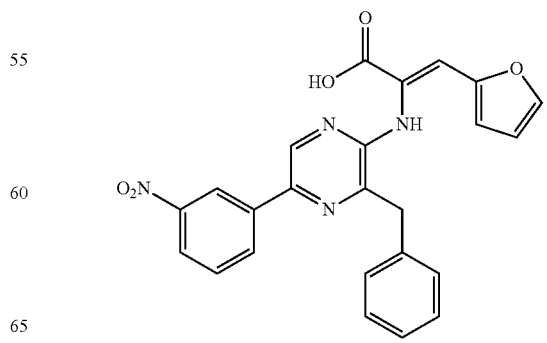

Following general procedure D, tert-butyl (Z)-2-((3-benzyl-5-(3-nitrophenyl)pyrazin-2-yl)amino)-3-(furan-2-yl)acrylate (0.26 g, 0.52 mmol) was reacted with trifluoroacetic acid (1 mL) to afford the crude product as a brown solid. ESI MS m/z 443 [M+H]+.

Step 3. (Z)-8-benzyl-2-(furan-2-ylmethylene)-6-(3-nitrophenyl)imidazo[1,2-a]pyrazin-3(2H)-one (JRW-1423)

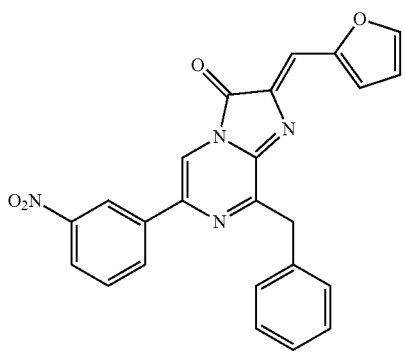 [SMILES: O=C1/C(=C/c2ccco2)N=C2C(Cc3ccccc3)=NC(c3cccc([N+](=O)[O-])c3)=CN12]

Following general procedure E, (Z)-2-((3-benzyl-5-(3-nitrophenyl)pyrazin-2-yl)amino)-3-(furan-2-yl)acrylic acid (0.52 mmol) was reacted with di(1H-imidazol-1-yl)methanone (0.17 g, 1.0 mmol) to afford the crude product as a red black solid. ESI MS m/z 425 [M+H]+.

Step 4. 8-benzyl-2-(furan-2-ylmethyl)-6-(3-nitrophenyl)imidazo[1,2-a]pyrazin-3(7H)-one (JRW-1424)

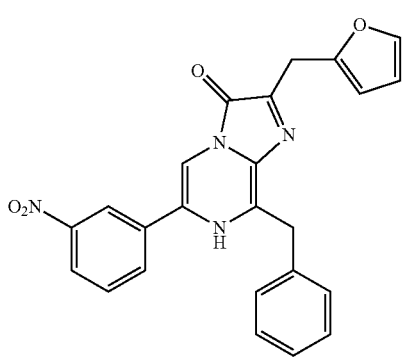 [SMILES: O=c1c(Cc2ccco2)nc2c(Cc3ccccc3)[nH]c(-c3cccc([N+](=O)[O-])c3)cn1-2]

Following general procedure F, (Z)-8-benzyl-2-(furan-2-ylmethylene)-6-(3-nitrophenyl)imidazo[1,2-a]pyrazin-3(2H)-one (0.52 mmol) was reacted with sodium borohydride (0.098 g, 2.6 mmol) to afford the desired product (0.13 g, 60% over three steps) as a dark orange solid. ¹H NMR (400 MHz, Methanol-d4) δ 8.75 (s, 1H), 8.35-8.12 (m, 3H), 7.74 (t, J=8.0 Hz, 1H), 7.49-7.38 (m, 3H), 7.37-7.29 (m, 2H), 7.29-7.20 (m, 1H), 6.34 (dd, J=3.2, 1.9 Hz, 1H), 6.12 (dd, 1=3.2, 1.0 Hz, 1H), 4.49 (s, 2H), 4.22 (s, 2H); ESI MS m/z 427 [M+H]+.

Example 17. 8-benzyl-6-(3-chloro-5-hydroxyphenyl)-2-(furan-2-ylmethyl)imidazo[1,2-a]pyrazin-3(7H)-one (JRW-1479)

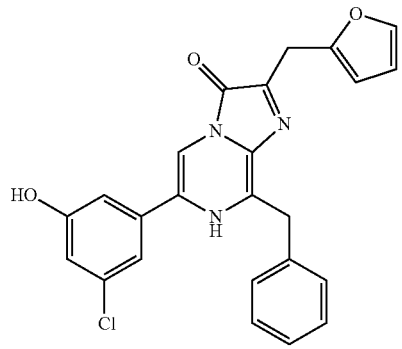 [SMILES: O=c1c(Cc2ccco2)nc2c(Cc3ccccc3)[nH]c(-c3cc(O)cc(Cl)c3)cn1-2]

Step 1. Tert-butyl (Z)-2-((3-benzyl-5-(3-((tert-butyldimethylsilyl)oxy)-5-chlorophenyl)pyrazin-2-yl)amino)-3-(furan-2-yl)acrylate (JRW-1470)

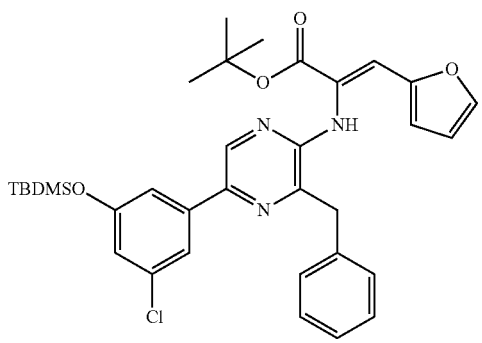 [SMILES: CC(C)(C)OC(=O)/C(=C/c1ccco1)Nc1ncc(-c2cc(Cl)cc(O[Si](C)(C)C(C)(C)C)c2)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with (3-((tert-butyldimethylsilyl)oxy)-5-chlorophenyl)boronic acid (0.25 g, 0.87 mmol) to afford the desired product (0.24 g, 88%) as a light brown foam. ESI MS m/z 618 [M+H]+.

Step 2. (Z)-2-((3-benzyl-5-(3-((tert-butyldimethylsilyl)oxy)-5-chlorophenyl)pyrazin-2-yl)amino)-3-(furan-2-yl)acrylic acid (JRW-1474)

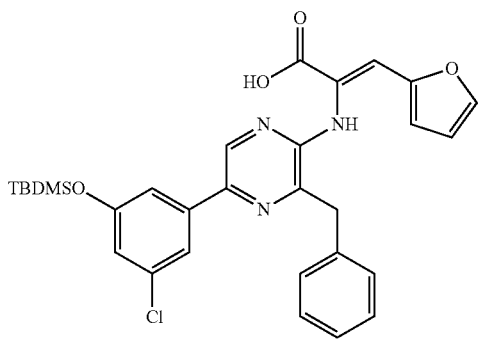 [SMILES: CC(C)(C)[Si](C)(C)Oc1cc(Cl)cc(-c2cnc(N/C(=C\c3ccco3)C(=O)O)c(Cc3ccccc3)n2)c1]

Following general procedure D, tert-butyl (Z)-2-((3-benzyl-5-(3-((tert-butyldimethylsilyl)oxy)-5-chlorophenyl)pyrazin-2-yl)amino)-3-(furan-2-yl)acrylate (0.24 g, 0.39 mmol) was reacted with trifluoroacetic acid (1 mL) to afford the crude product as a brown oil. ESI MS m/z 562 [M+H]$^+$.

Step 3. (Z)-8-benzyl-6-(3-((tert-butyldimethylsilyl)oxy)-5-chlorophenyl)-2-(furan-2-ylmethylene)imidazo[1,2-a]pyrazin-3(2H)-one (JRW-1476)

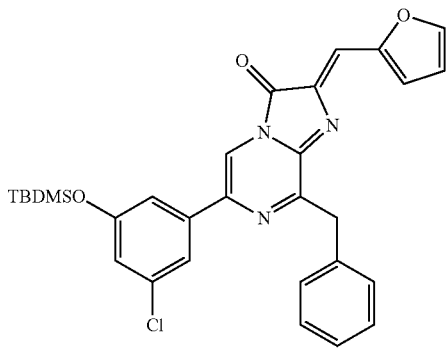 [SMILES: CC(C)(C)[Si](C)(C)Oc1cc(Cl)cc(C2=CN3C(=O)/C(=C/c4ccco4)N=C3C(Cc3ccccc3)=N2)c1]

Following general procedure E, (Z)-2-((3-benzyl-5-(3-((tert-butyldimethylsilyl)oxy)-5-chlorophenyl)pyrazin-2-yl)amino)-3-(furan-2-yl)acrylic acid (0.39 mmol) was reacted with di(1H-imidazol-1-yl)methanone (0.13 g, 0.78 mmol) to afford the crude product as a red solid. ESI MS m/z 544 [M+H]$^+$.

Step 4. 8-benzyl-6-(3-((tert-butyldimethylsilyl)oxy)-5-chlorophenyl)-2-(furan-2-ylmethyl)imidazo[1,2-a]pyrazin-3(7H)-one (JRW-1477)

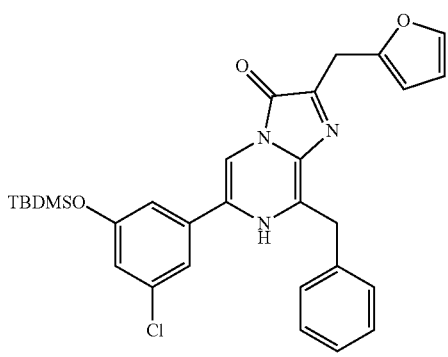 [SMILES: CC(C)(C)[Si](C)(C)Oc1cc(Cl)cc(-c2cn3c(=O)c(Cc4ccco4)nc-3c(Cc3ccccc3)[nH]2)c1]

Following general procedure F, (Z)-8-benzyl-6-(3-((tert-butyldimethylsilyl)oxy)-5-chlorophenyl)-2-(furan-2-ylmethylene)imidazo[1,2-a]pyrazin-3(2H)-one (0.39 mmol) was reacted with sodium borohydride (0.044 g, 1.2 mmol) to afford the crude product. ESI MS m/z 546 [M+H]$^+$.

Step 5. 8-benzyl-6-(3-chloro-5-hydroxyphenyl)-2-(furan-2-ylmethyl)imidazo[1,2-a]pyrazin-3(7H)-one (JRW-1479)

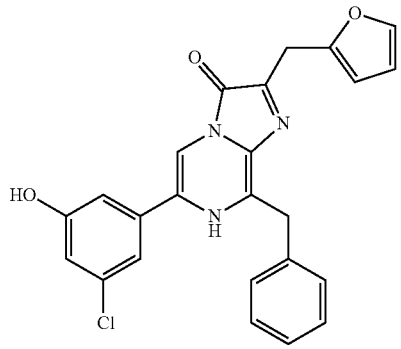

Following general procedure G, 8-benzyl-6-(3-((tert-butyldimethylsilyl)oxy)-5-chlorophenyl)-2-(furan-2-ylmethyl)imidazo[1,2-a]pyrazin-3(7H)-one (0.39 mmol) was reacted with HCl (1 mL, 6M) to afford the desired product (0.12 g, 71% over 4 steps) as an orange foam. $^1$H NMR (400 MHz, Methanol-d4) δ 7.85 (s, 1H), 7.47-7.36 (m, 3H), 7.36-7.29 (m, 2H), 7.29-7.17 (m, 2H), 7.08 (s, 1H), 6.90 (t, J=2.1 Hz, 1H), 6.34 (dd, J=3.2, 1.9 Hz, 1H), 6.12 (dd, J=3.2, 1.0 Hz, 1H), 4.44 (s, 2H), 4.21 (s, 2H); ESI MS m/z 432 [M+H]$^+$.

Example 18. 6-(3-amino-2-fluorophenyl)-8-benzyl-2-(furan-2-ylmethyl)imidazo[1,2-a]pyrazin-3(7H)-one (JRW-1482)

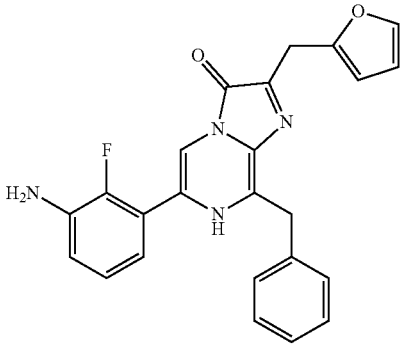

Step 1. Tert-butyl (Z)-2-((3-benzyl-5-(2-fluoro-3-nitrophenyl)pyrazin-2-yl)amino)-3-(furan-2-yl)acrylate (JRW-1469)

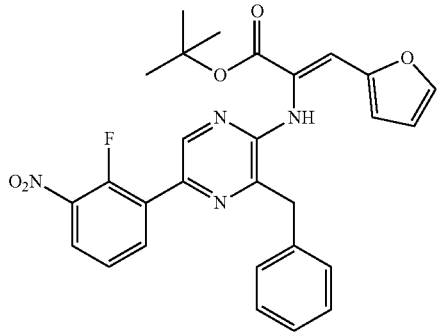 [SMILES: CC(C)(C)OC(=O)/C(=C/c1ccco1)Nc1ncc(-c2cccc([N+](=O)[O-])c2F)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with (2-fluoro-3-nitrophenyl)boronic acid (0.12 g, 0.66 mmol) to afford the desired product (0.22 g, 97%) as a yellow solid. ESI MS m/z 517 [M+H]$^+$.

Step 2. (Z)-2-((3-benzyl-5-(2-fluoro-3-nitrophenyl)pyrazin-2-yl)amino)-3-(furan-2-yl)acrylic acid (JRW-1471)

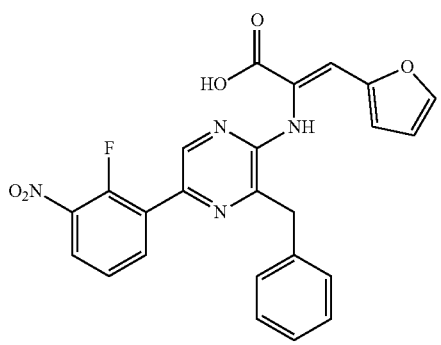 [SMILES: O=C(O)/C(=C/c1ccco1)Nc1ncc(-c2cccc([N+](=O)[O-])c2F)nc1Cc1ccccc1]

Following general procedure D, tert-butyl (Z)-2-((3-benzyl-5-(2-fluoro-3-nitrophenyl)pyrazin-2-yl)amino)-3-(furan-2-yl)acrylate (0.22 g, 0.42 mmol) was reacted with trifluoroacetic acid (1 mL) to afford the crude product as an orange solid. ESI MS m/z 461 [M+H]$^+$.

Step 3. (Z)-8-benzyl-6-(2-fluoro-3-nitrophenyl)-2-(furan-2-ylmethylene)imidazo[1,2-a]pyrazin-3(2H)-one (JRW-1473)

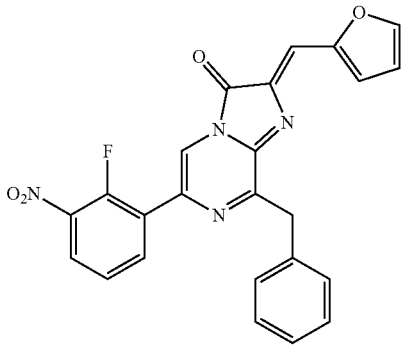 [SMILES: O=C1/C(=C/c2ccco2)N=C2C(Cc3ccccc3)=NC(c3cccc([N+](=O)[O-])c3F)=CN12]

Following general procedure E, Z)-2-((3-benzyl-5-(2-fluoro-3-nitrophenyl)pyrazin-2-yl)amino)-3-(furan-2-yl)acrylic acid (0.43 mmol) was reacted with di(1H-imidazol-1-yl)methanone (0.14 g, 0.85 mmol) to afford the crude product as a red solid. ESI MS m/z 443 [M+H]$^+$.

Step 4. 8-benzyl-6-(2-fluoro-3-nitrophenyl)-2-(furan-2-ylmethyl)imidazo[1,2-a]pyrazin-3(7H)-one (JRW-1475)

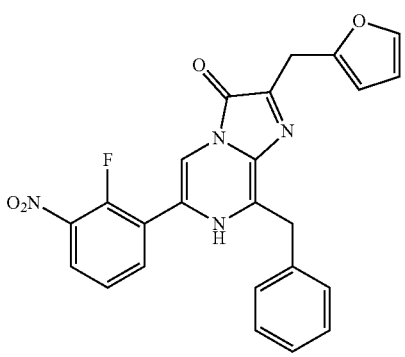 [SMILES: O=c1c(Cc2ccco2)nc2c(Cc3ccccc3)[nH]c(-c3cccc([N+](=O)[O-])c3F)cn1-2]

Following general procedure F, (Z)-8-benzyl-6-(2-fluoro-3-nitrophenyl)-2-(furan-2-ylmethylene)imidazo[1,2-a]pyrazin-3(2H)-one (0.42 mmol) was reacted with sodium borohydride (0.048 g, 1.3 mmol) to afford the desired product (0.17 g, 90% over three steps). ESI MS m/z 445 [M+H]$^+$.

Step 5. 6-(3-amino-2-fluorophenyl)-8-benzyl-2-(furan-2-ylmethyl)imidazo[1,2-a]pyrazin-3(7H)-one (JRW-1482)

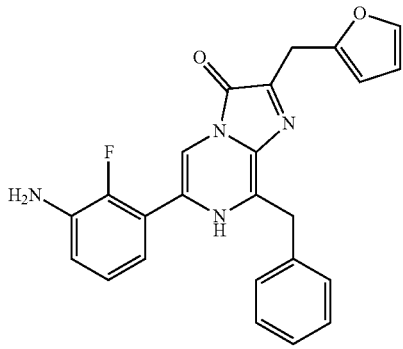

Following general procedure H, 8-benzyl-6-(2-fluoro-3-nitrophenyl)-2-(furan-2-ylmethyl)imidazo[1,2-a]pyrazin-3(7H)-one (0.17 g, 0.38 mmol) was reacted with hydrogen (1 atm) to obtain the desired product (0.058 g, 37%) as an orange solid. $^1$H NMR (400 MHz, Methanol-d4) δ 7.67 (s, 1H), 7.47-7.38 (m, 3H), 7.37-7.29 (m, 2H), 7.29-7.19 (m, 1H), 7.07-6.99 (m, 1H), 6.96 (td, J=8.2, 1.8 Hz, 1H), 6.83 (s, 1H), 6.34 (dd, J=3.2, 1.9 Hz, 1H), 6.13 (dd, 1=3.2, 1.0 Hz, 1H), 4.41 (s, 2H), 4.22 (s, 2H); ESI MS m/z 415 [M+H]$^+$.

Example 19. 8-benzyl-6-(4-chloro-3-hydroxyphenyl)-2-(furan-2-ylmethyl)imidazo[1,2-a]pyrazin-3(7H)-one (JRW-1483)

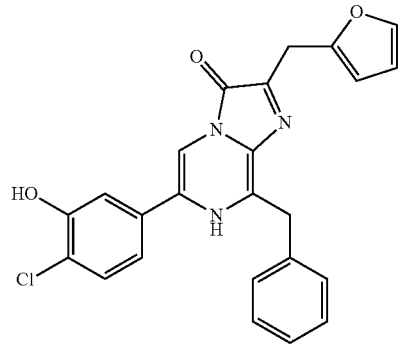 [SMILES: O=c1c(Cc2ccco2)nc2c(Cc3ccccc3)[nH]c(-c3ccc(Cl)c(O)c3)cn1-2]

Step 1. Tert-butyl (Z)-2-((3-benzyl-5-(3-((tert-butyldimethylsilyl)oxy)-4-chlorophenyl)pyrazin-2-yl)amino)-3-(furan-2-yl)acrylate (JRW-1472)

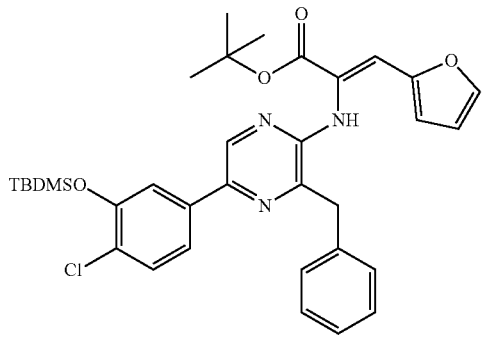 [SMILES: CC(C)(C)OC(=O)/C(=C/c1ccco1)Nc1ncc(-c2ccc(Cl)c(O[Si](C)(C)C(C)(C)C)c2)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with (3-((tert-butyldimethylsilyl)oxy)-4-chlorophenyl)boronic acid (0.25 g, 0.88 mmol) to afford the desired product (0.23 g, 84%) as an orange solid. ESI MS m/z 618 [M+H]$^+$.

Step 2. (Z)-2-((3-benzyl-5-(3-((tert-butyldimethylsilyl)oxy)-4-chlorophenyl)pyrazin-2-yl)amino)-3-(furan-2-yl)acrylic acid (JRW-1478)

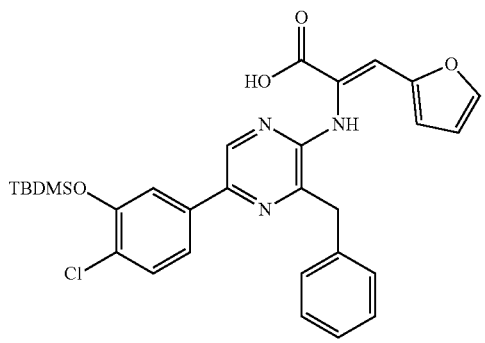 [SMILES: CC(C)(C)[Si](C)(C)Oc1cc(-c2cnc(N/C(=C\c3ccco3)C(=O)O)c(Cc3ccccc3)n2)ccc1Cl]

Following general procedure D, tert-butyl (Z)-2-((3-benzyl-5-(3-((tert-butyldimethylsilyl)oxy)-4-chlorophenyl)pyrazin-2-yl)amino)-3-(furan-2-yl)acrylate (0.23 g, 0.37 mmol) was reacted with trifluoroacetic acid (1 mL) to afford the crude product. ESI MS m/z 562 [M+H]$^+$.

Step 3. (Z)-8-benzyl-6-(3-((tert-butyldimethylsilyl)oxy)-4-chlorophenyl)-2-(furan-2-ylmethylene)imidazo[1,2-a]pyrazin-3(2H)-one (JRW-1480)

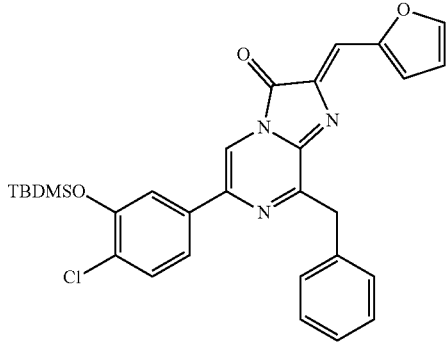 [SMILES: CC(C)(C)[Si](C)(C)Oc1cc(C2=CN3C(=O)/C(=C/c4ccco4)N=C3C(Cc3ccccc3)=N2)ccc1Cl]

Following general procedure E, (Z)-2-((3-benzyl-5-(3-((tert-butyldimethylsilyl)oxy)-4-chlorophenyl)pyrazin-2-yl)amino)-3-(furan-2-yl)acrylic acid (0.37 mmol) was reacted with di(1H-imidazol-1-yl)methanone (0.12 g, 0.74 mmol) to afford the crude product as a black solid. ESI MS m/z 544 [M+H]⁺.

Step 4. 8-benzyl-6-(3-((tert-butyldimethylsilyl)oxy)-4-chlorophenyl)-2-(furan-2-ylmethyl)imidazo[1,2-a]pyrazin-3(7H)-one (JRW-1481)

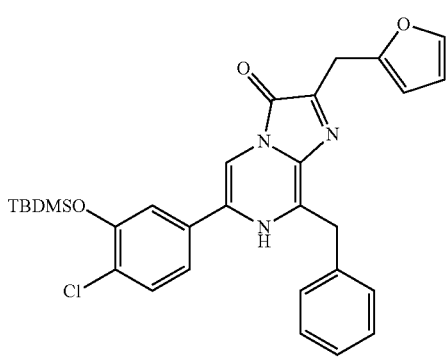 [SMILES: CC(C)(C)[Si](C)(C)Oc1cc(-c2cn3c(=O)c(Cc4ccco4)nc-3c(Cc3ccccc3)[nH]2)ccc1Cl]

Following general procedure F, (Z)-8-benzyl-6-(3-((tert-butyldimethylsilyl)oxy)-4-chlorophenyl)-2-(furan-2-ylmethylene)imidazo[1,2-a]pyrazin-3(2H)-one (0.37 mmol) was reacted with sodium borohydride (0.070 g, 1.8 mmol) to afford the crude product. ESI MS m/z 546 [M+H]⁺.

Step 5. 8-benzyl-6-(4-chloro-3-hydroxyphenyl)-2-(furan-2-ylmethyl)imidazo[1,2-a]pyrazin-3(7H)-one (JRW-1483)

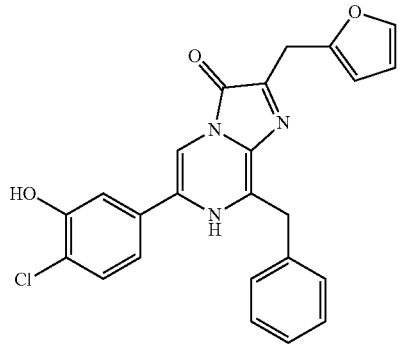 [SMILES: O=c1c(Cc2ccco2)nc2c(Cc3ccccc3)[nH]c(-c3ccc(Cl)c(O)c3)cn1-2]

Following general procedure G, 8-benzyl-6-(3-((tert-butyldimethylsilyl)oxy)-4-chlorophenyl)-2-(furan-2-ylmethyl)imidazo[1,2-a]pyrazin-3(7H)-one (0.37 mmol) was reacted with HCl (1 mL, 6M) to afford the desired product (0.11 g, 66% over 4 steps) as a dark orange solid. ¹H NMR (400 MHz, Methanol-d4) δ 7.49-7.36 (m, 5H), 7.36-7.21 (m, 4H), 7.18 (s, 1H), 6.34 (dd, J=3.2, 1.9 Hz, 1H), 6.16-6.09 (m, 1H), 4.44 (s, 2H), 4.21 (s, 2H); ESI MS m/z 432 [M+H]⁺.

Example 20. 8-benzyl-6-(2-chloro-3-hydroxyphenyl)-2-(furan-2-ylmethyl)imidazo[1,2-a]pyrazin-3(7H)-one (JRW-1488)

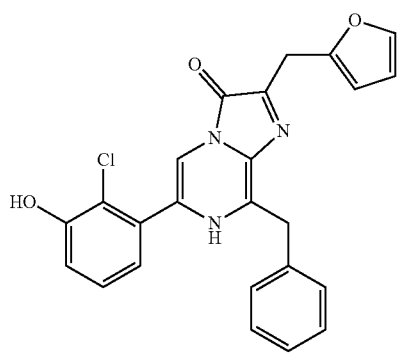

Step 1. Tert-butyl (Z)-2-((3-benzyl-5-(3-((tert-butyldimethylsilyl)oxy)-2-chlorophenyl)pyrazin-2-yl)amino)-3-(furan-2-yl)acrylate (JRW-1484)

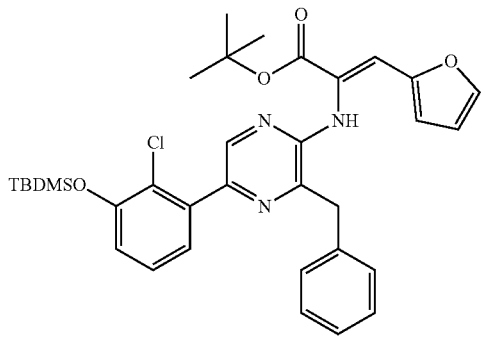 [SMILES: CC(C)(C)OC(=O)/C(=C/c1ccco1)Nc1ncc(-c2cccc(O[Si](C)(C)C(C)(C)C)c2Cl)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with tert-butyl(2-chloro-3-(4,4,5,5-tetramethyl-1,3,2-dioxaborolan-2-yl)phenoxy)dimethylsilane (0.24 g, 0.66 mmol) to afford the desired product (0.19 g, 69%) as a yellow solid. ESI MS m/z 618 [M+H]$^+$.

Step 2. (Z)-2-((3-benzyl-5-(2-chloro-3-hydroxyphenyl)pyrazin-2-yl)amino)-3-(furan-2-yl)acrylic acid (JRW-1485)

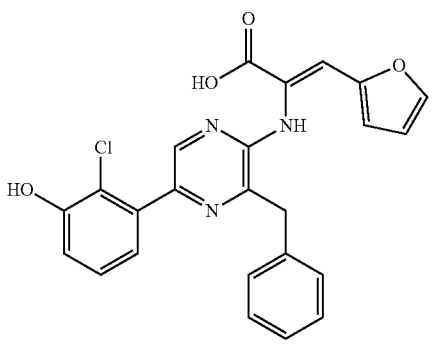 [SMILES: O=C(O)/C(=C/c1ccco1)Nc1ncc(-c2cccc(O)c2Cl)nc1Cc1ccccc1]

Following general procedure D, tert-butyl (Z)-2-((3-benzyl-5-(3-((tert-butyldimethylsilyl)oxy)-2-chlorophenyl)pyrazin-2-yl)amino)-3-(furan-2-yl)acrylate (0.18 g, 0.29 mmol) was reacted with trifluoroacetic acid (1 mL) to afford the crude product. ESI MS m/z 448 [M+H]$^+$.

Step 3. (Z)-8-benzyl-6-(2-chloro-3-hydroxyphenyl)-2-(furan-2-ylmethylene)imidazo[1,2-a]pyrazin-3(2H)-one (JRW-1487)

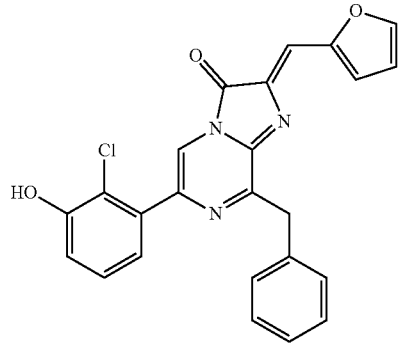

Following general procedure E, (Z)-2-((3-benzyl-5-(2-chloro-3-hydroxyphenyl)pyrazin-2-yl)amino)-3-(furan-2-yl)acrylic acid (0.29 mmol) was reacted with di(1H-imidazol-1-yl)methanone (0.094 g, 0.58 mmol) to afford the crude product as a red solid. ESI MS m/z 430 [M+H]$^+$.

Step 4. 8-benzyl-6-(2-chloro-3-hydroxyphenyl)-2-(furan-2-ylmethyl)imidazo[1,2-a]pyrazin-3(7H)-one (JRW-1488)

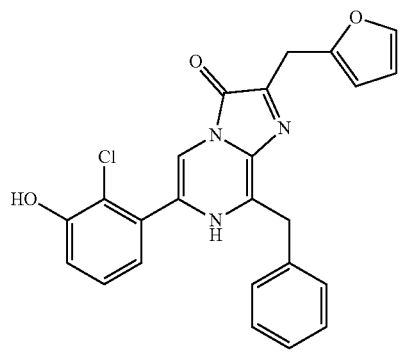

Following general procedure F, (Z)-8-benzyl-6-(2-chloro-3-hydroxyphenyl)-2-(furan-2-ylmethylene)imidazo[1,2-a]pyrazin-3(2H)-one (0.29 mmol) was reacted with sodium borohydride (0.055 g, 1.4 mmol) to afford the desired product (0.076 g, 60% over 3 steps) as an orange solid. $^1$H NMR (400 MHz, Methanol-d4) δ 7.50 (s, 1H), 7.45-7.38 (m, 3H), 7.36-7.22 (m, 4H), 7.09 (dd, J=8.3, 1.5 Hz, 1H), 7.03 (dd, J=7.5, 1.5 Hz, 1H), 6.34 (dd, J=3.2, 1.9 Hz, 1H), 6.14 (dd, J=3.2, 1.0 Hz, 1H), 4.39 (s, 2H), 4.23 (s, 2H); ESI MS m/z 432 [M+H]$^+$.

Example 21. 8-(4-fluorobenzyl)-2-(furan-2-ylm-ethyl)-6-(3-hydroxyphenyl)imidazo[1,2-a]pyrazin-3(7H)-one (JRW-1498)

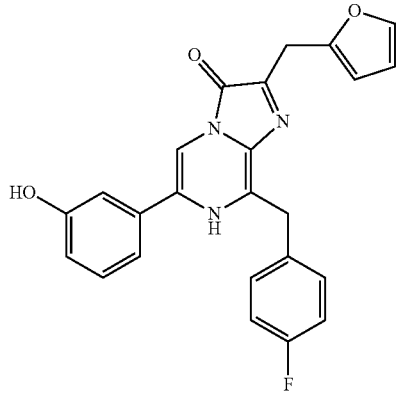 [SMILES: O=c1c(Cc2ccco2)nc2c(Cc3ccc(F)cc3)[nH]c(-c3cccc(O)c3)cn1-2]

Step 1. 5-(3-((tert-butyldimethylsilyl)oxy)phenyl)pyrazin-2-amine (JRW-1407)

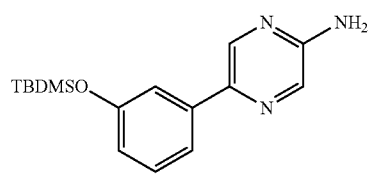 [SMILES: CC(C)(C)[Si](C)(C)Oc1cccc(-c2cnc(N)cn2)c1]

Following general procedure $C_{1-5}$-bromopyrazin-2-amine (1.0 g, 5.7 mmol) was reacted with (3-((tert-butyldimethylsilyl)oxy)phenyl)boronic acid (1.7 g, 6.9 mmol) to afford the desired product (1.56 g, 90%) as a white solid. ESI MS m/z 302 [M+H]⁺.

Step 2. 3-bromo-5-(3-((tert-butyldimethylsilyl)oxy)phenyl)pyrazin-2-amine (JRW-1409)

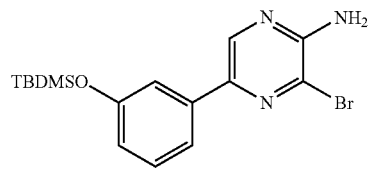 [SMILES: CC(C)(C)[Si](C)(C)Oc1cccc(-c2cnc(N)c(Br)n2)c1]

A solution of 5-(3-((tert-butyldimethylsilyl)oxy)phenyl)pyrazin-2-amine (1.56 g, 5.2 mmol) in DMF (20 mL) was prepared and chilled with an ice bath, N-bromosuccinamide (1.0 g, 5.7 mmol) was added, and the reaction was stirred for 30 min. The mixture was diluted with ethyl acetate and water, and the aqueous layer was extracted with ethyl acetate. The organic layers were combined, dried with sodium sulfate, filtered, concentrated, and purified with silica gel chromatography to yield the desired product (1.5 g, 76%) as a brown solid. ESI MS m/z 380 [M+H]⁺.

Step 3. 5-(3-((tert-butyldimethylsilyl)oxy)phenyl)-3-(4-fluorobenzyl)pyrazin-2-amine (JRW-1412)

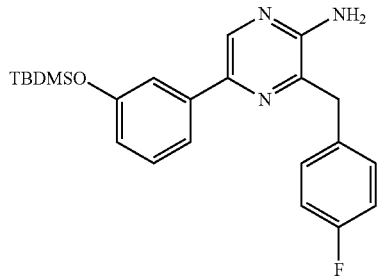 [SMILES: CC(C)(C)[Si](C)(C)Oc1cccc(-c2cnc(N)c(Cc3ccc(F)cc3)n2)c1]

Following general procedure $C_{1-3}$-bromo-5-(3-((tert-butyldimethylsilyl)oxy)phenyl)pyrazin-2-amine (0.50 g, 1.3 mmol) was reacted with 2-(4-fluorobenzyl)-4,4,5,5-tetramethyl-1,3,2-dioxaborolane (0.47 g, 2.0 mmol) to afford the desired product (0.28 g, 52%) as an orange solid. ESI MS m/z 410 [M+H]⁺.

Step 4. Tert-butyl 2-((5-(3-((tert-butyldimethylsilyl)oxy)phenyl)-3-(4-fluorobenzyl)pyrazin-2-yl)amino)-2-(diethoxyphosphoryl)acetate (JRW-1489)

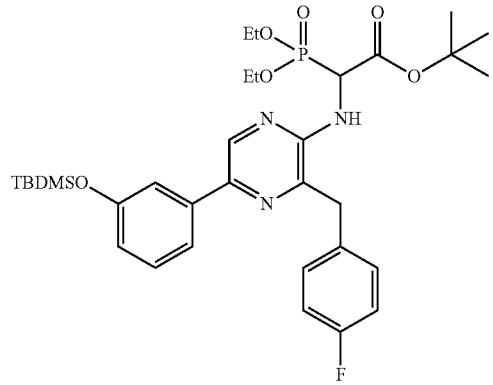 [SMILES: CCOP(=O)(OCC)C(Nc1ncc(-c2cccc(O[Si](C)(C)C(C)(C)C)c2)nc1Cc1ccc(F)cc1)C(=O)OC(C)(C)C]

Following general procedure A, 5-(3-((tert-butyldimethylsilyl)oxy)phenyl)-3-(4-fluorobenzyl)pyrazin-2-amine (0.28 g, 0.68 mmol) was reacted with tert-butyl 2-diazo-2-(diethoxyphosphoryl)acetate (0.28 g, 1.0 mmol) to afford the desired product (0.28 g, 62%) as a brown oil. ESI MS m/z 660 [M+H]⁺.

Step 5. Tert-butyl (Z)-2-((5-(3-((tert-butyldimethyl-silyl)oxy)phenyl)-3-(4-fluorobenzyl)pyrazin-2-yl)amino)-3-(furan-2-yl)acrylate (JRW-1490)

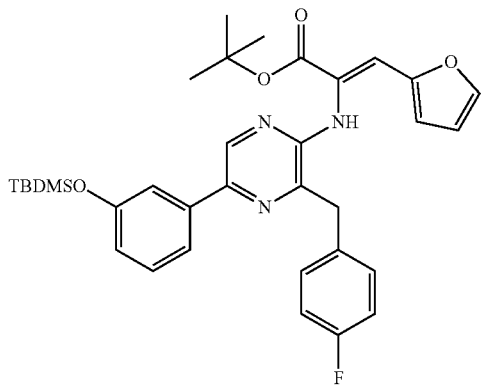 [SMILES: CC(C)(C)OC(=O)/C(=C/c1ccco1)Nc1ncc(-c2cccc(O[Si](C)(C)C(C)(C)C)c2)nc1Cc1ccc(F)cc1]

Following general procedure B, tert-butyl 2-((5-(3-((tert-butyldimethylsilyl)oxy)phenyl)-3-(4-fluorobenzyl)pyrazin-2-yl)amino)-2-(diethoxyphosphoryl)acetate (0.28 g, 0.42 mmol) was reacted with furfural (0.081 g, 0.84 mmol) to afford the desired product (0.15 g, 59%). ESI MS m/z 602 [M+H]$^+$.

Step 6. (Z)-2-((5-(3-((tert-butyldimethylsilyl)oxy)phenyl)-3-(4-fluorobenzyl)pyrazin-2-yl)amino)-3-(furan-2-yl)acrylic acid (JRW-1493)

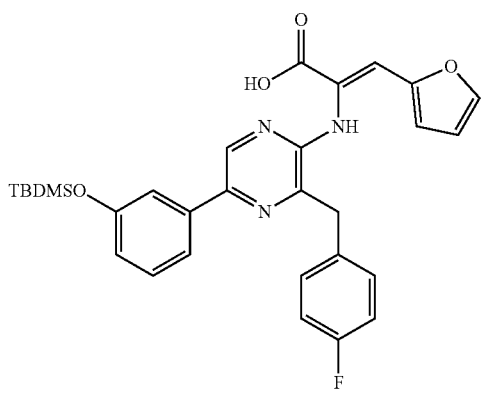 [SMILES: CC(C)(C)[Si](C)(C)Oc1cccc(-c2cnc(N/C(=C\c3ccco3)C(=O)O)c(Cc3ccc(F)cc3)n2)c1]

Following general procedure D, tert-butyl (Z)-2-((5-(3-((tert-butyldimethylsilyl)oxy)phenyl)-3-(4-fluorobenzyl)pyrazin-2-yl)amino)-3-(furan-2-yl)acrylate (0.15 g, 0.25 mmol) was reacted with trifluoroacetic acid (1 mL) to afford the crude product. ESI MS m/z 546 [M+H]$^+$.

Step 7. (Z)-6-(3-((tert-butyldimethylsilyl)oxy)phenyl)-8-(4-fluorobenzyl)-2-(furan-2-ylmethylene)imidazo[1,2-a]pyrazin-3(2H)-one (JRW-1495)

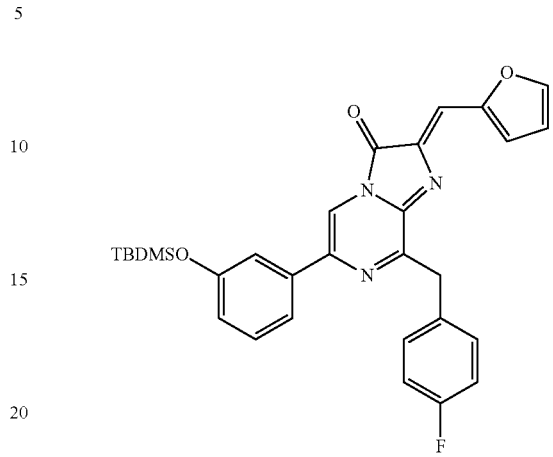

Following general procedure E, (Z)-2-((5-(3-((tert-butyldimethylsilyl)oxy)phenyl)-3-(4-fluorobenzyl)pyrazin-2-yl)amino)-3-(furan-2-yl)acrylic acid (0.25 mmol) was reacted with di(1H-imidazol-1-yl)methanone (0.081 g, 0.50 mmol) to afford the crude product as a red solid. ESI MS m/z 528 [M+H]$^+$.

Step 8. 6-(3-((tert-butyldimethylsilyl)oxy)phenyl)-8-(4-fluorobenzyl)-2-(furan-2-ylmethyl)imidazo[1,2-a]pyrazin-3(7H)-one (JRW-1497)

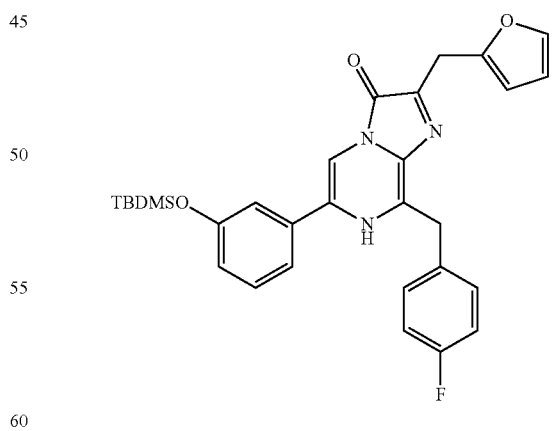

Following general procedure F, (Z)-6-(3-((tert-butyldimethylsilyl)oxy)phenyl)-8-(4-fluorobenzyl)-2-(furan-2-ylmethylene)imidazo[1,2-a]pyrazin-3(2H)-one (0.25 mmol) was reacted with sodium borohydride (0.047 g, 1.2 mmol) to afford the crude product as a red orange solid. ESI MS m/z 530 [M+H]$^+$.

Step 9. 8-(4-fluorobenzyl)-2-(furan-2-ylmethyl)-6-(3-hydroxyphenyl)imidazo[1,2-a]pyrazin-3(7H)-one (JRW-1498)

Step 1. Tert-butyl (Z)-2-((3-benzyl-5-(2-chloro-5-hydroxyphenyl)pyrazin-2-yl)amino)-3-(furan-2-yl)acrylate (JRW-1515)

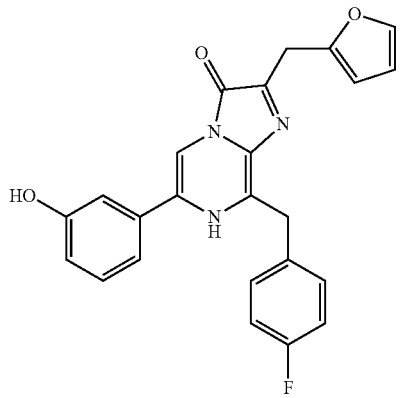 [SMILES: O=c1c(Cc2ccco2)nc2c(Cc3ccc(F)cc3)[nH]c(-c3cccc(O)c3)cn1-2]

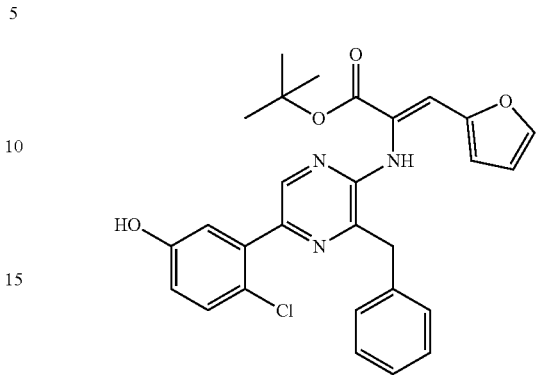

Following general procedure G, 6-(3-((tert-butyldimethylsilyl)oxy)phenyl)-8-(4-fluorobenzyl)-2-(furan-2-ylmethyl)imidazo[1,2-a]pyrazin-3(7H)-one (0.25 mmol) was reacted with HCl (1 mL, 6M) to afford the desired product (0.083 g, 77% over 4 steps) as an orange brown foam. $^1$H NMR (400 MHz, Methanol-d4) δ 7.74 (s, 1H), 7.50-7.37 (m, 3H), 7.32 (t, J=7.9 Hz, 1H), 7.20-7.00 (m, 4H), 6.93-6.88 (m, 1H), 6.34 (dd, J=3.2, 1.9 Hz, 1H), 6.13 (dd, J=3.2, 1.0 Hz, 1H), 4.42 (s, 2H), 4.21 (s, 2H); ESI MS m/z 416 [M+H]$^+$.

Following general procedure C, tert-butyl (Z)-2-((3-benzyl-5-bromopyrazin-2-yl)amino)-3-(furan-2-yl)acrylate (0.20 g, 0.44 mmol) was reacted with (2-chloro-5-hydroxyphenyl)boronic acid (0.15 g, 0.088 mmol) to afford the desired product (0.22 g, 99%) as a yellow foam. ESI MS m/z 504 [M+H]$^+$.

Example 22. 8-benzyl-6-(2-chloro-5-hydroxyphenyl)-2-(furan-2-ylmethyl)imidazo[1,2-a]pyrazin-3(7H)-one (JRW-1525)

Step 2. (Z)-2-((3-benzyl-5-(2-chloro-5-hydroxyphenyl)pyrazin-2-yl)amino)-3-(furan-2-yl)acrylic acid (JRW-1519)

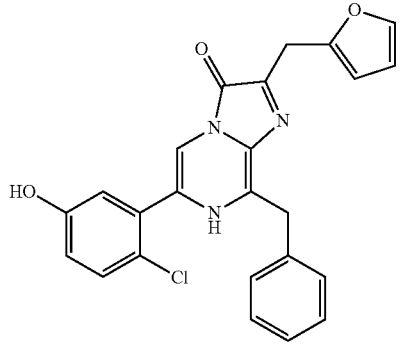 [SMILES: O=c1c(Cc2ccco2)nc2c(Cc3ccccc3)[nH]c(-c3cc(O)ccc3Cl)cn1-2]

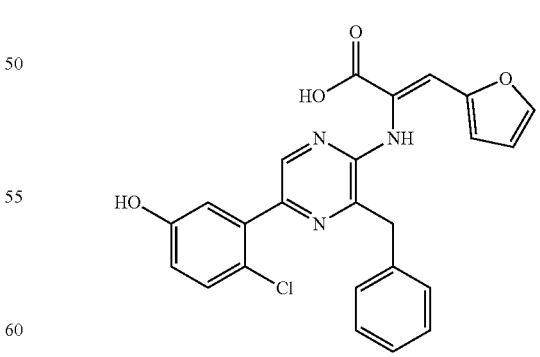

Following general procedure D, tert-butyl (Z)-2-((3-benzyl-5-(2-chloro-5-hydroxyphenyl)pyrazin-2-yl)amino)-3-(furan-2-yl)acrylate (0.22 g, 0.44 mmol) was reacted with trifluoroacetic acid (1 mL) to afford the crude product. ESI MS m/z 448 [M+H]$^+$.

Step 3. (Z)-8-benzyl-6-(2-chloro-5-hydroxyphenyl)-2-(furan-2-ylmethylene)imidazo[1,2-a]pyrazin-3(2H)-one (JRW-1523)

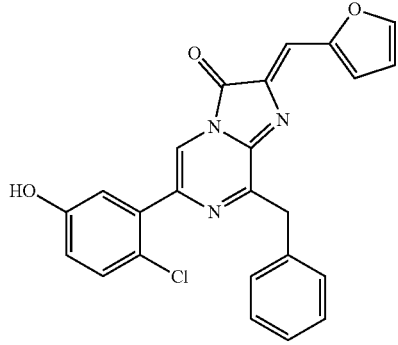 [SMILES: O=C1/C(=C/c2ccco2)N=C2C(Cc3ccccc3)=NC(c3cc(O)ccc3Cl)=CN12]

Following general procedure E, (Z)-2-((3-benzyl-5-(2-chloro-5-hydroxyphenyl)pyrazin-2-yl)amino)-3-(furan-2-yl)acrylic acid (0.44 mmol) was reacted with di(1H-imidazol-1-yl)methanone (0.14 g, 0.089 mmol) to afford the crude product as a red black solid. ESI MS m/z 430 [M+H]$^+$.

Step 4. 8-benzyl-6-(2-chloro-5-hydroxyphenyl)-2-(furan-2-ylmethyl)imidazo[1,2-a]pyrazin-3(7H)-one (JRW-1525)

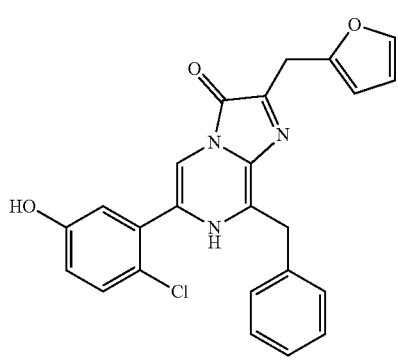

Following general procedure F, (Z)-8-benzyl-6-(2-chloro-5-hydroxyphenyl)-2-(furan-2-ylmethylene)imidazo[1,2-a]pyrazin-3(2H)-one (0.44 mmol) was reacted with sodium borohydride (0.051 g, 1.3 mmol) to afford the desired product (0.12 g, 64% over three steps) as an orange solid. $^1$H NMR (400 MHz, Methanol-d4) δ 7.84 (s, 1H), 7.47-7.37 (m, 3H), 7.36-7.29 (m, 2H), 7.29-7.21 (m, 1H), 7.03-6.88 (m, 2H), 6.62 (dt, J=10.5, 1.9 Hz, 1H), 6.33 (dd, 1=3.2, 1.9 Hz, 1H), 6.12 (dd, 1=3.2, 0.9 Hz, 1H), 4.44 (s, 2H), 4.21 (s, 2H); ESI MS m/z 432 [M+H]$^+$.

Example 23. 8-benzyl-6-(3-fluoro-5-hydroxyphenyl)-2-(furan-2-ylmethyl)imidazo[1,2-a]pyrazin-3(7H)-one (JRW-1526)

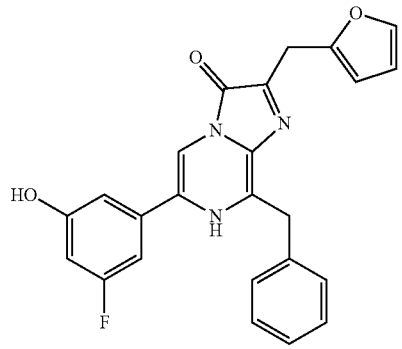

Step 1. Tert-butyl (Z)-2-((3-benzyl-5-(3-fluoro-5-hydroxyphenyl)pyrazin-2-yl)amino)-3-(furan-2-yl)acrylate (JRW-1516)

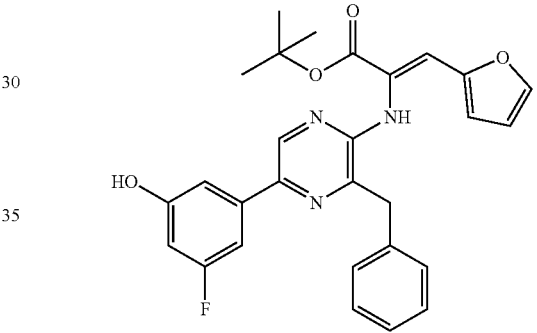

Following general procedure C, tert-butyl (Z)-2-((3-benzyl-5-bromopyrazin-2-yl)amino)-3-(furan-2-yl)acrylate (0.20 g, 0.44 mmol) was reacted with (3-fluoro-5-hydroxyphenyl)boronic acid (0.14 g, 0.088 mmol) to afford the desired product (0.20 g, 94%) as a yellow foam. ESI MS m/z 488 [M+H]$^+$.

Step 2. (Z)-2-((3-benzyl-5-(3-fluoro-5-hydroxyphenyl)pyrazin-2-yl)amino)-3-(furan-2-yl)acrylic acid (JRW-1520)

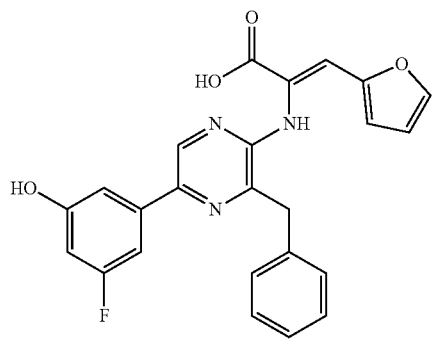 [SMILES: O=C(O)/C(=C/c1ccco1)Nc1ncc(-c2cc(O)cc(F)c2)nc1Cc1ccccc1]

Following general procedure D, tert-butyl (Z)-2-((3-benzyl-5-(3-fluoro-5-hydroxyphenyl)pyrazin-2-yl)amino)-3-(furan-2-yl)acrylate (0.20 g, 0.41 mmol) was reacted with trifluoroacetic acid (1 mL) to afford the crude product. ESI MS m/z 432 [M+H]+.

Step 3. (Z)-8-benzyl-6-(3-fluoro-5-hydroxyphenyl)-2-(furan-2-ylmethylene)imidazo[1,2-a]pyrazin-3(2H)-one (JRW-1524)

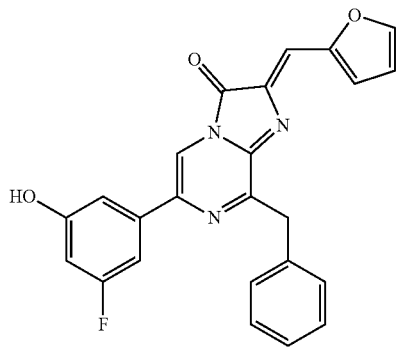 [SMILES: O=C1/C(=C/c2ccco2)N=C2C(Cc3ccccc3)=NC(c3cc(O)cc(F)c3)=CN12]

Following general procedure E, (Z)-2-((3-benzyl-5-(3-fluoro-5-hydroxyphenyl)pyrazin-2-yl)amino)-3-(furan-2-yl) acrylic acid (0.41 mmol) was reacted with di(1H-imidazol-1-yl)methanone (0.13 g, 0.082 mmol) to afford the crude product as a purple black solid. ESI MS m/z 414 [M+H]+.

Step 4. 8-benzyl-6-(3-fluoro-5-hydroxyphenyl)-2-(furan-2-ylmethyl)imidazo[1,2-a]pyrazin-3(7H)-one (JRW-1526)

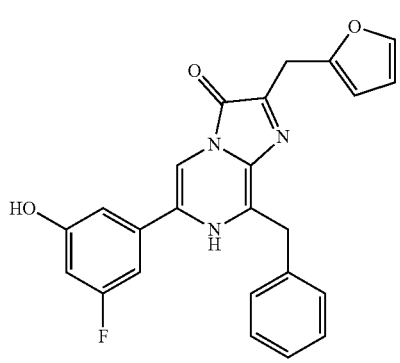

Following general procedure F, (Z)-8-benzyl-6-(3-fluoro-5-hydroxyphenyl)-2-(furan-2-ylmethylene)imidazo[1,2-a]pyrazin-3(2H)-one (0.41 mmol) was reacted with sodium borohydride (0.047 g, 1.2 mmol) to afford the desired product (0.13 g, 76% over three steps) as a brown orange foam. 1H NMR (400 MHz, Methanol-d4) δ 7.50 (s, 1H), 7.45-7.37 (m, 3H), 7.37-7.18 (m, 4H), 6.97 (d, J=2.9 Hz, 1H), 6.92 (dd, J=8.7, 2.9 Hz, 1H), 6.34 (dd, J=3.2, 1.9 Hz, 1H), 6.14 (dt, J=3.2, 1.0 Hz, 1H), 4.39 (s, 2H), 4.22 (s, 2H); ESI MS m/z 416 [M+H]+.

Example 24. 6-(3-amino-5-fluorophenyl)-8-benzyl-2-(furan-2-ylmethyl)imidazo[1,2-a]pyrazin-3(7H)-one (JRW-1535)

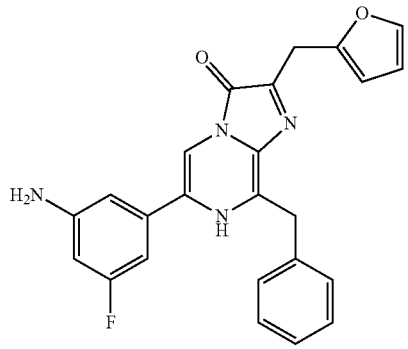

Step 1. Tert-butyl (Z)-2-((3-benzyl-5-(3-fluoro-5-nitrophenyl)pyrazin-2-yl)amino)-3-(furan-2-yl)acrylate (JRW-1527)

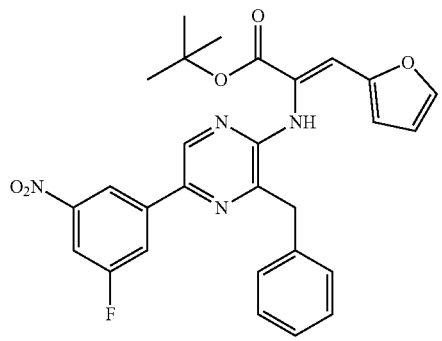 [SMILES: CC(C)(C)OC(=O)/C(=C/c1ccco1)Nc1ncc(-c2cc(F)cc([N+](=O)[O-])c2)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with 2-(3-fluoro-5-nitrophenyl)-4,4,5,5-tetramethyl-1,3,2-dioxaborolane (0.23 g, 0.088 mmol) to afford the desired product (0.21 g, 92%) as a yellow orange foam. ESI MS m/z 517 [M+H]+.

Step 2. (Z)-2-((3-benzyl-5-(3-fluoro-5-nitrophenyl)pyrazin-2-yl)amino)-3-(furan-2-yl)acrylic acid (JRW-1529)

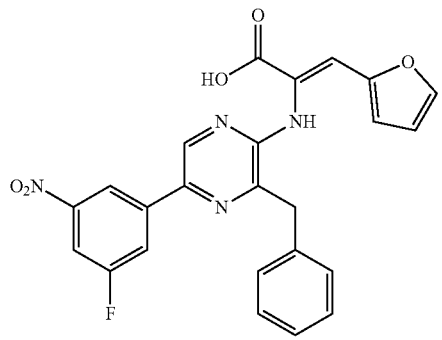 [SMILES: O=C(O)/C(=C/c1ccco1)Nc1ncc(-c2cc(F)cc([N+](=O)[O-])c2)nc1Cc1ccccc1]

Following general procedure D, tert-butyl (Z)-2-((3-benzyl-5-(3-fluoro-5-nitrophenyl)pyrazin-2-yl)amino)-3-(furan-2-yl)acrylate (0.21 g, 0.41 mmol) was reacted with trifluoroacetic acid (1 mL) to afford the crude product. ESI MS m/z 461 [M+H]+.

Step 3. (Z)-8-benzyl-6-(3-fluoro-5-nitrophenyl)-2-(furan-2-ylmethylene)imidazo[1,2-a]pyrazin-3(2H)-one (JRW-1531)

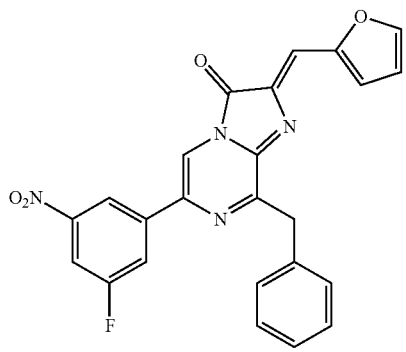 [SMILES: O=C1/C(=C/c2ccco2)N=C2C(Cc3ccccc3)=NC(c3cc(F)cc([N+](=O)[O-])c3)=CN12]

Following general procedure E, (Z)-2-((3-benzyl-5-(3-fluoro-5-nitrophenyl)pyrazin-2-yl)amino)-3-(furan-2-yl) acrylic acid (0.41 mmol) was reacted with di(1H-imidazol-1-yl)methanone (0.13 g, 0.081 mmol) to afford the crude product as a red solid. ESI MS m/z 443 [M+H]+.

Step 4. 8-benzyl-6-(3-fluoro-5-nitrophenyl)-2-(furan-2-ylmethyl)imidazo[1,2-a]pyrazin-3(7H)-one (JRW-1533)

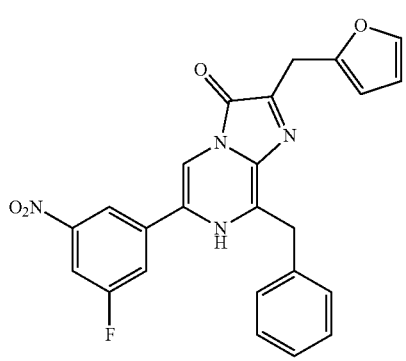 [SMILES: O=c1c(Cc2ccco2)nc2c(Cc3ccccc3)[nH]c(-c3cc(F)cc([N+](=O)[O-])c3)cn1-2]

Following general procedure F, (Z)-8-benzyl-6-(3-fluoro-5-nitrophenyl)-2-(furan-2-ylmethylene)imidazo[1,2-a]pyrazin-3(2H)-one (0.41 mmol) was reacted with sodium borohydride (0.076 g, 2.0 mmol) to afford the crude product. ESI MS m/z 445 [M+H]+.

Step 5. 6-(3-amino-5-fluorophenyl)-8-benzyl-2-(furan-2-ylmethyl)imidazo[1,2-a]pyrazin-3(7H)-one (JRW-1535)

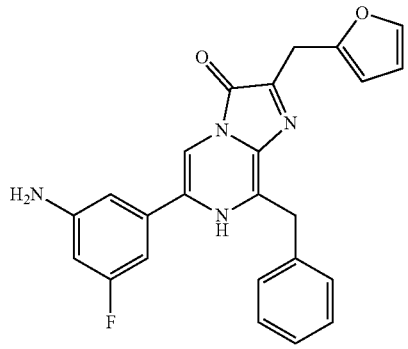

Following general procedure H, 8-benzyl-6-(3-fluoro-5-nitrophenyl)-2-(furan-2-ylmethyl)imidazo[1,2-a]pyrazin-3(7H)-one (0.41 mmol) was reacted with hydrogen (1 atm) to obtain the desired product (0.037 g, 22% over 4 steps) as an orange brown foam. $^1$H NMR (400 MHz, Methanol-d4) δ 7.74 (s, 1H), 7.47-7.36 (m, 3H), 7.36-7.28 (m, 2H), 7.28-7.18 (m, 1H), 6.85-6.70 (m, 1H), 6.70-6.57 (m, 1H), 6.48 (dt, J=11.0, 2.2 Hz, 1H), 6.33 (dd, 1=3.2, 1.9 Hz, 1H), 6.12 (dd, 1=3.2, 1.0 Hz, 1H), 4.43 (s, 2H), 4.21 (s, 2H); ESI MS m/z 415 [M+H]+.

Example 25. 6-(3-amino-4-fluorophenyl)-8-benzyl-2-(furan-2-ylmethyl)imidazo[1,2-a]pyrazin-3(7H)-one (JRW-1536)

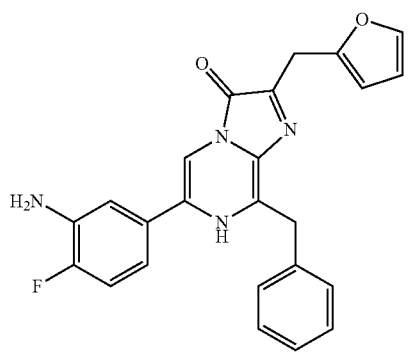

Step 1. Tert-butyl (Z)-2-((3-benzyl-5-(4-fluoro-3-nitrophenyl)pyrazin-2-yl)amino)-3-(furan-2-yl)acrylate (JRW-1528)

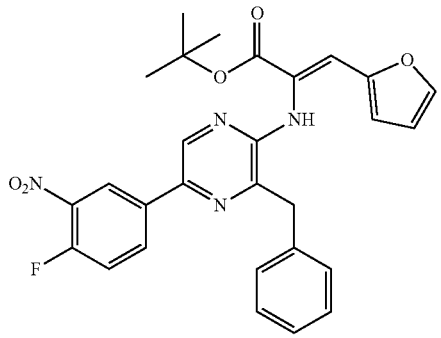 [SMILES: CC(C)(C)OC(=O)/C(=C/c1ccco1)Nc1ncc(-c2ccc(F)c([N+](=O)[O-])c2)nc1Cc1ccccc1]

Following general procedure C, tert-butyl (Z)-2-((3-benzyl-5-bromopyrazin-2-yl)amino)-3-(furan-2-yl)acrylate (0.20 g, 0.44 mmol) was reacted with (4-fluoro-3-nitrophenyl)boronic acid (0.16 g, 0.088 mmol) to afford the desired product (0.20 g, 88%) as a yellow foam. ESI MS m/z 517 [M+H]$^+$.

Step 2. (Z)-2-((3-benzyl-5-(4-fluoro-3-nitrophenyl)pyrazin-2-yl)amino)-3-(furan-2-yl)acrylic acid (JRW-1530)

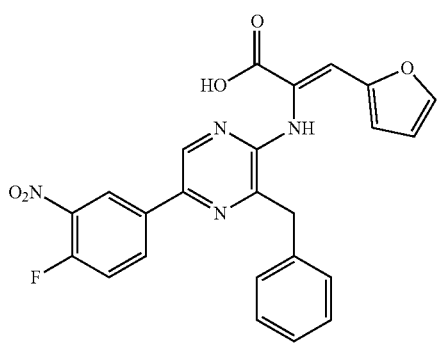 [SMILES: O=C(O)/C(=C/c1ccco1)Nc1ncc(-c2ccc(F)c([N+](=O)[O-])c2)nc1Cc1ccccc1]

Following general procedure D, tert-butyl (Z)-2-((3-benzyl-5-(4-fluoro-3-nitrophenyl)pyrazin-2-yl)amino)-3-(furan-2-yl)acrylate (0.20 g, 0.39 mmol) was reacted with trifluoroacetic acid (1 mL) to afford the crude product. ESI MS m/z 461 [M+H]$^+$.

Step 3. (Z)-8-benzyl-6-(4-fluoro-3-nitrophenyl)-2-(furan-2-ylmethylene)imidazo[1,2-a]pyrazin-3(2H)-one (JRW-1532)

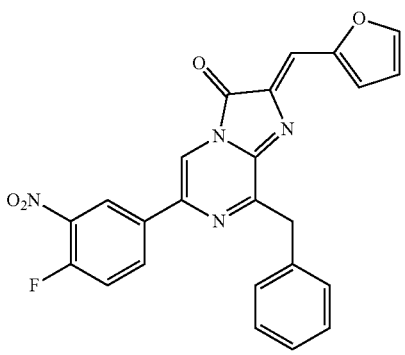 [SMILES: O=C1/C(=C/c2ccco2)N=C2C(Cc3ccccc3)=NC(c3ccc(F)c([N+](=O)[O-])c3)=CN12]

Following general procedure E, (Z)-2-((3-benzyl-5-(4-fluoro-3-nitrophenyl)pyrazin-2-yl)amino)-3-(furan-2-yl)acrylic acid (0.39 mmol) was reacted with di(1H-imidazol-1-yl)methanone (0.12 g, 0.077 mmol) to afford the crude product as a red black solid. ESI MS m/z 443 [M+H]$^+$.

Step 4. 8-benzyl-6-(4-fluoro-3-nitrophenyl)-2-(furan-2-ylmethyl)imidazo[1,2-a]pyrazin-3(7H)-one (JRW-1534)

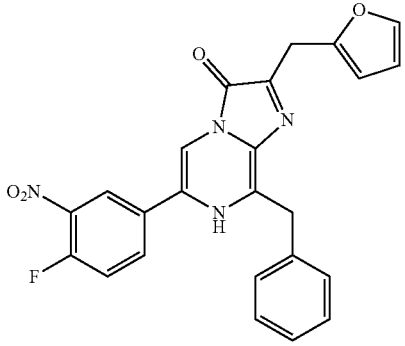 [SMILES: O=c1c(Cc2ccco2)nc2c(Cc3ccccc3)[nH]c(-c3ccc(F)c([N+](=O)[O-])c3)cn1-2]

Following general procedure F, (Z)-8-benzyl-6-(4-fluoro-3-nitrophenyl)-2-(furan-2-ylmethylene)imidazo[1,2-a]pyrazin-3(2H)-one (0.39 mmol) was reacted with sodium borohydride (0.073 g, 1.9 mmol) to afford the crude product. ESI MS m/z 445 [M+H]$^+$.

Step 5. 6-(3-amino-4-fluorophenyl)-8-benzyl-2-(furan-2-ylmethyl)imidazo[1,2-a]pyrazin-3(7H)-one (JRW-1536)

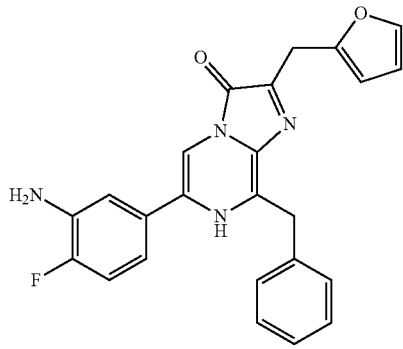

Following general procedure H, 8-benzyl-6-(4-fluoro-3-nitrophenyl)-2-(furan-2-ylmethyl)imidazo[1,2-a]pyrazin-3(7H)-one (0.41 mmol) was reacted with hydrogen (1 atm) to obtain the desired product (0.028 g, 17% over 4 steps) as an orange brown foam. $^1$H NMR (400 MHz, Methanol-d4) δ 7.65 (s, 1H), 7.47-7.38 (m, 3H), 7.36-7.28 (m, 2H), 7.28-7.20 (m, 1H), 7.17-7.01 (m, 2H), 6.95-6.82 (m, 1H), 6.33 (dd, J=3.2, 1.9 Hz, 1H), 6.13 (dd, J=3.2, 1.0 Hz, 1H), 4.43 (s, 2H), 4.21 (s, 2H); ESI MS m/z 415 [M+H]$^+$.

Example 26. 6-(3-amino-2-fluorophenyl)-8-benzyl-2-(3-(methoxymethyl)benzyl)imidazo[1,2-a]pyrazin-3(7H)-one (JRW-1609)

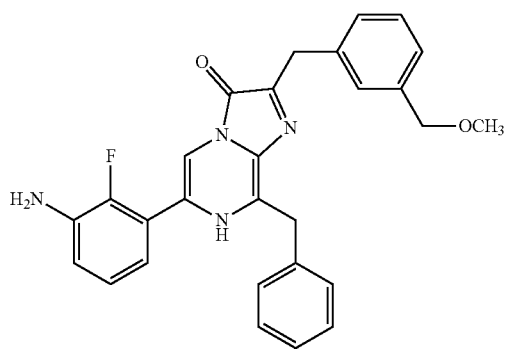

Step 1. Tert-butyl (Z)-2-((3-benzyl-5-bromopyrazin-2-yl)amino)-3-(3-(methoxymethyl)phenyl)acrylate (JRW-1598)

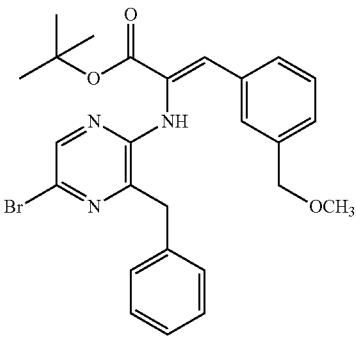 [SMILES: COCc1cccc(/C=C(\Nc2ncc(Br)nc2Cc2ccccc2)C(=O)OC(C)(C)C)c1]

Following general procedure B, tert-butyl 2-((3-benzyl-5-bromopyrazin-2-yl)amino)-2-(diethoxyphosphoryl)acetate (0.33 g, 0.64 mmol) was reacted with 3-(methoxymethyl)benzaldehyde (0.12 g, 0.77 mmol) to afford the desired product (0.094 g, 28%). ESI MS m/z 511 [M+H]$^+$.

Step 2. Tert-butyl (Z)-2-((3-benzyl-5-(2-fluoro-3-nitrophenyl)pyrazin-2-yl)amino)-3-(3-(methoxymethyl)phenyl)acrylate (JRW-1600)

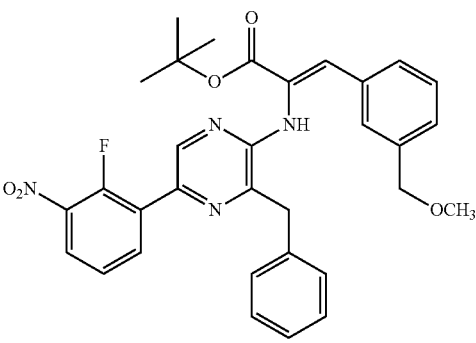 [SMILES: COCc1cccc(/C=C(\Nc2ncc(-c3cccc([N+](=O)[O-])c3F)nc2Cc2ccccc2)C(=O)OC(C)(C)C)c1]

Following general procedure C, tert-butyl (Z)-2-((3-benzyl-5-bromopyrazin-2-yl)amino)-3-(3-(methoxymethyl)phenyl)acrylate (0.09 g, 0.18 mmol) was reacted with 2-(2-fluoro-3-nitrophenyl)-4,4,5,5-tetramethyl-1,3,2-dioxaborolane (0.070 g, 0.26 mmol) to afford the desired product (0.077 g, 77%) as a yellow solid. ESI MS m/z 571 [M+H]$^+$.

Step 3. (Z)-2-((3-benzyl-5-(2-fluoro-3-nitrophenyl)pyrazin-2-yl)amino)-3-(3-(methoxymethyl)phenyl)acrylic acid (JRW-1601)

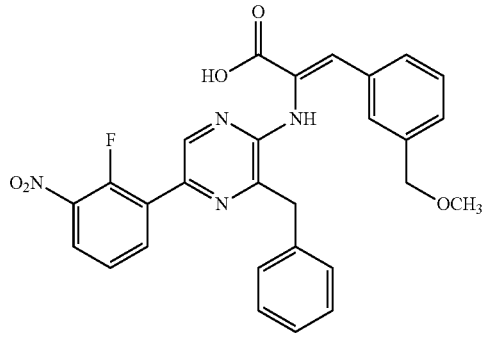 [SMILES: COCc1cccc(/C=C(\Nc2ncc(-c3cccc([N+](=O)[O-])c3F)nc2Cc2ccccc2)C(=O)O)c1]

Following general procedure D, tert-butyl (Z)-2-((3-benzyl-5-(2-fluoro-3-nitrophenyl)pyrazin-2-yl)amino)-3-(3-(methoxymethyl)phenyl)acrylate (0.077 g, 0.13 mmol) was reacted with trifluoroacetic acid (1 mL) to afford the crude product as a light red oil. ESI MS m/z 515 [M+H]+.

Step 4. (Z)-8-benzyl-6-(2-fluoro-3-nitrophenyl)-2-(3-(methoxymethyl)benzylidene)imidazo[1,2-a]pyrazin-3(2H)-one (JRW-1603)

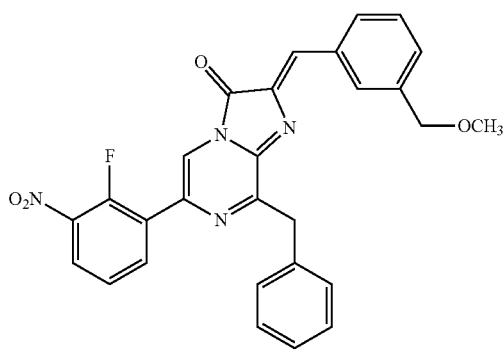 [SMILES: COCc1cccc(/C=C2\N=C3C(Cc4ccccc4)=NC(c4cccc([N+](=O)[O-])c4F)=CN3C2=O)c1]

Following general procedure E, (Z)-2-((3-benzyl-5-(2-fluoro-3-nitrophenyl)pyrazin-2-yl)amino)-3-(3-(methoxymethyl)phenyl)acrylic acid (0.14 mmol) was reacted with di(1H-imidazol-1-yl)methanone (0.044 g, 0.27 mmol) to afford the crude product as a red solid. ESI MS m/z 497 [M+H]+.

Step 5. 8-benzyl-6-(2-fluoro-3-nitrophenyl)-2-(3-(methoxymethyl)benzyl)imidazo[1,2-a]pyrazin-3(7H)-one (JRW-1604)

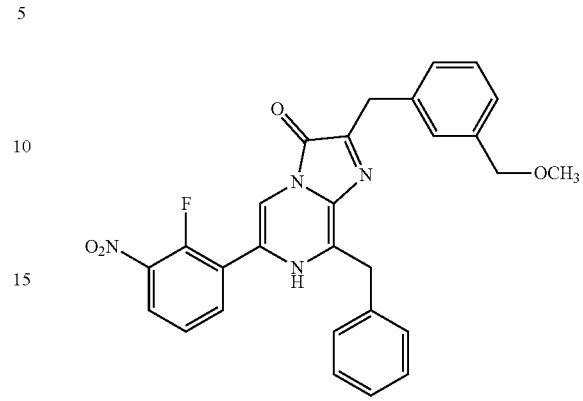

Following general procedure F, (Z)-8-benzyl-6-(2-fluoro-3-nitrophenyl)-2-(3-(methoxymethyl)benzylidene)imidazo[1,2-a]pyrazin-3(2H)-one (0.14 mmol) was reacted with sodium borohydride (0.025 g, 0.67 mmol) to afford the desired product (0.040 g, 59% over three steps) as an orange solid. ESI MS m/z 499 [M+H]+.

Step 6. 6-(3-amino-2-fluorophenyl)-8-benzyl-2-(3-(methoxymethyl)benzyl)imidazo[1,2-a]pyrazin-3(7H)-one (JRW-1609)

Following general procedure H, 8-benzyl-6-(2-fluoro-3-nitrophenyl)-2-(3-(methoxymethyl)benzyl)imidazo[1,2-a]pyrazin-3(7H)-one (0.040 g, 0.080 mmol) was reacted with hydrogen (1 atm) to obtain the desired product (0.018 g, 48%) as an orange solid. $^1$H NMR (400 MHz, Methanol-d4) δ 7.73-7.58 (m, 1H), 7.45-7.38 (m, 2H), 7.37-7.14 (m, 8H), 7.06-6.99 (m, 1H), 6.95 (td, J=8.2, 1.8 Hz, 1H), 6.88-6.76 (m, 1H), 4.43 (s, 2H), 4.40 (s, 2H), 4.21 (s, 2H), 3.36 (s, 3H); ESI MS m/z 467 [M+H]+.

Example 27. 6-(3-amino-2-fluorophenyl)-8-benzyl-2-((5-(trifluoromethyl)furan-2-yl)methyl)imidazo[1,2-a]pyrazin-3(7H)-one (JRW-1610)

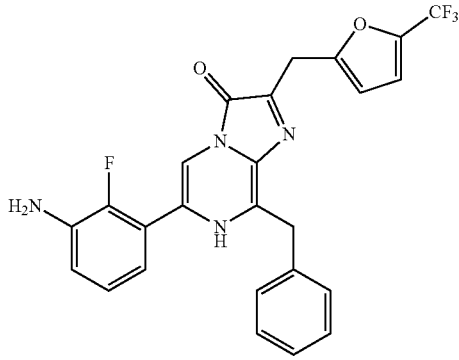 [SMILES: Nc1cccc(-c2cn3c(=O)c(Cc4ccc(C(F)(F)F)o4)nc-3c(Cc3ccccc3)[nH]2)c1F]

Step 1. Tert-butyl (Z)-2-((3-benzyl-5-bromopyrazin-2-yl)amino)-3-(5-(trifluoromethyl)furan-2-yl)acrylate (JRW-1602)

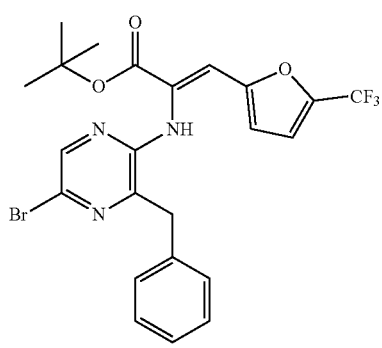 [SMILES: CC(C)(C)OC(=O)/C(=C/c1ccc(C(F)(F)F)o1)Nc1ncc(Br)nc1Cc1ccccc1]

Following general procedure B, tert-butyl 2-((3-benzyl-5-bromopyrazin-2-yl)amino)-2-(diethoxyphosphoryl)acetate (0.38 g, 0.74 mmol) was reacted with 5-(trifluoromethyl)furan-2-carbaldehyde (0.15 g, 0.89 mmol) to afford the desired product (0.21 g, 54%) as a red foam. ESI MS m/z 525 [M+H]$^+$.

Step 2. Tert-butyl (Z)-2-((3-benzyl-5-(2-fluoro-3-nitrophenyl)pyrazin-2-yl)amino)-3-(5-(trifluoromethyl)furan-2-yl)acrylate (JRW-1605)

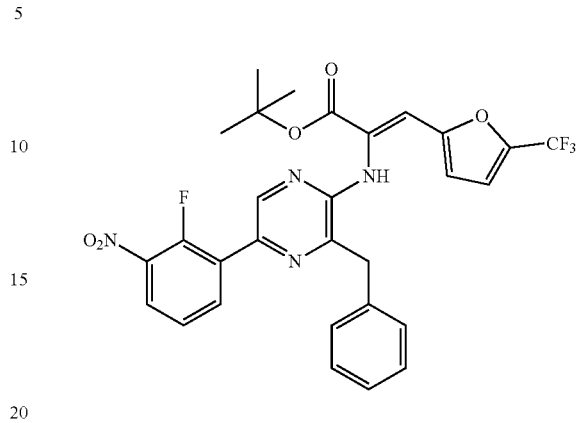

Following general procedure C, tert-butyl (Z)-2-((3-benzyl-5-bromopyrazin-2-yl)amino)-3-(5-(trifluoromethyl)furan-2-yl)acrylate (0.080 g, 0.15 mmol) was reacted with 2-(2-fluoro-3-nitrophenyl)-4,4,5,5-tetramethyl-1,3,2-dioxaborolane (0.061 g, 0.23 mmol) to afford the desired product (0.080 g, 89%) as a light brown solid. ESI MS m/z 585 [M+H]+.

Step 3. (Z)-2-((3-benzyl-5-(2-fluoro-3-nitrophenyl)pyrazin-2-yl)amino)-3-(5-(trifluoromethyl)furan-2-yl)acrylic acid (JRW-1606)

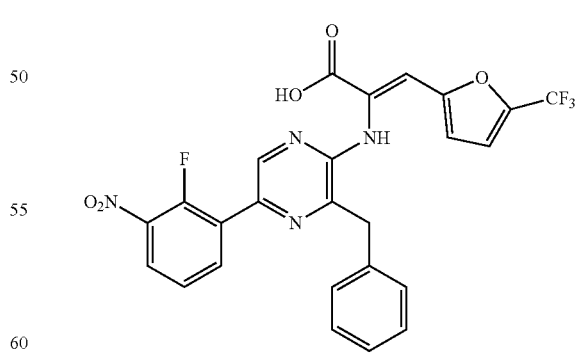

Following general procedure D, tert-butyl (Z)-2-((3-benzyl-5-(2-fluoro-3-nitrophenyl)pyrazin-2-yl)amino)-3-(5-(trifluoromethyl)furan-2-yl)acrylate (0.10 g, 0.17 mmol) was reacted with trifluoroacetic acid (1 mL) to afford the crude product as a purple solid. ESI MS m/z 529 [M+H]$^+$.

Step 4. (Z)-8-benzyl-6-(2-fluoro-3-nitrophenyl)-2-((5-(trifluoromethyl)furan-2-yl)methylene)imidazo[1,2-a]pyrazin-3(2H)-one (JRW-1607)

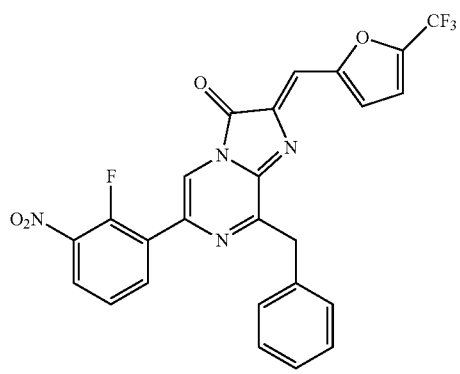 [SMILES: O=C1/C(=C/c2ccc(C(F)(F)F)o2)N=C2C(Cc3ccccc3)=NC(c3cccc([N+](=O)[O-])c3F)=CN12]

Following general procedure E, (Z)-2-((3-benzyl-5-(2-fluoro-3-nitrophenyl)pyrazin-2-yl)amino)-3-(5-(trifluoromethyl)furan-2-yl)acrylic acid (0.17 mmol) was reacted with di(1H-imidazol-1-yl)methanone (0.055 g, 0.34 mmol) to afford the crude product as a red solid. ESI MS m/z 511 [M+H]$^+$.

Step 5. 8-benzyl-6-(2-fluoro-3-nitrophenyl)-2-((5-(trifluoromethyl)furan-2-yl)methyl)imidazo[1,2-a]pyrazin-3(7H)-one (JRW-1608)

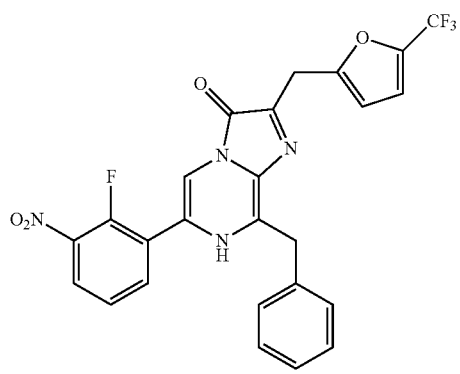 [SMILES: Nc1cccc(-c2cn3c(=O)c(Cc4ccc(C(F)(F)F)o4)nc-3c(Cc3ccccc3)[nH]2)c1F]

Following general procedure F, (Z)-8-benzyl-6-(2-fluoro-3-nitrophenyl)-2-((5-(trifluoromethyl)furan-2-yl)methylene)imidazo[1,2-a]pyrazin-3(2H)-one (0.17 mmol) was reacted with sodium borohydride (0.032 g, 0.85 mmol) to afford the desired product (0.071 g, 81% over three steps) as an orange solid. ESI MS m/z 513 [M+H]$^+$.

Step 6. 6-(3-amino-2-fluorophenyl)-8-benzyl-2-((5-(trifluoromethyl)furan-2-yl)methyl)imidazo[1,2-a]pyrazin-3(7H)-one (JRW-1610)

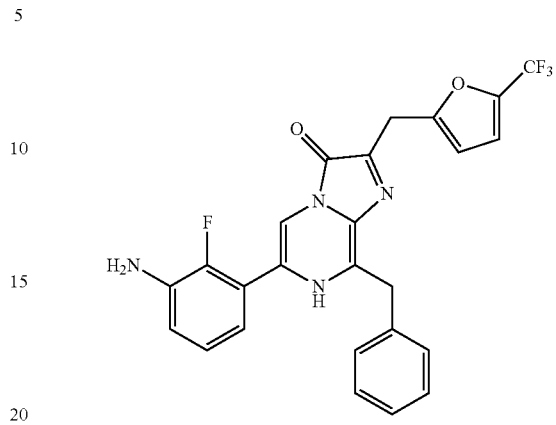

Following general procedure H, 8-benzyl-6-(2-fluoro-3-nitrophenyl)-2-((5-(trifluoromethyl)furan-2-yl)methyl)imidazo[1,2-a]pyrazin-3(7H)-one (0.071 g, 0.14 mmol) was reacted with hydrogen (1 atm) to obtain the desired product (0.012 g, 18%) as an orange brown solid. $^1$H NMR (400 MHz, Methanol-d4) δ 7.68 (s, 1H), 7.49-7.37 (m, 2H), 7.35-7.22 (m, 3H), 7.08-7.00 (m, 1H), 6.96 (td, J=8.2, 1.8 Hz, 1H), 6.93-6.77 (m, 2H), 6.33 (d, J=3.4 Hz, 1H), 4.42 (s, 2H), 4.29 (s, 2H); ESI MS m/z 483 [M+H]$^+$.

Example 28. 8-benzyl-6-(2-fluoro-3-hydroxyphenyl)-2-((5-(trifluoromethyl)furan-2-yl)methyl)imidazo[1,2-a]pyrazin-3(7H)-one (JRW-1619)

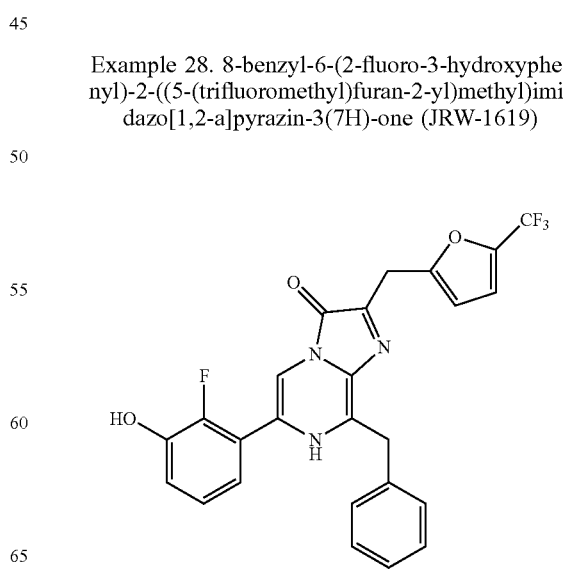

Step 1. Tert-butyl (Z)-2-((3-benzyl-5-(3-((tert-butyldimethylsilyl)oxy)-2-fluorophenyl)pyrazin-2-yl)amino)-3-(5-(trifluoromethyl)furan-2-yl)acrylate (JRW-1611)

Step 3. (Z)-8-benzyl-6-(3-((tert-butyldimethylsilyl)oxy)-2-fluorophenyl)-2-((5-(trifluoromethyl)furan-2-yl)methylene)imidazo[1,2-a]pyrazin-3(2H)-one (JRW-1615)

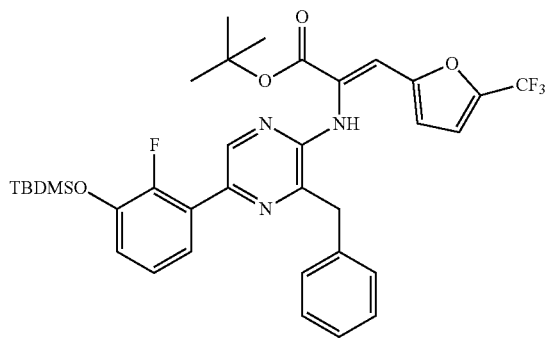 [SMILES: CC(C)(C)OC(=O)/C(=C/c1ccc(C(F)(F)F)o1)Nc1ncc(-c2cccc(O[Si](C)(C)C(C)(C)C)c2F)nc1Cc1ccccc1]

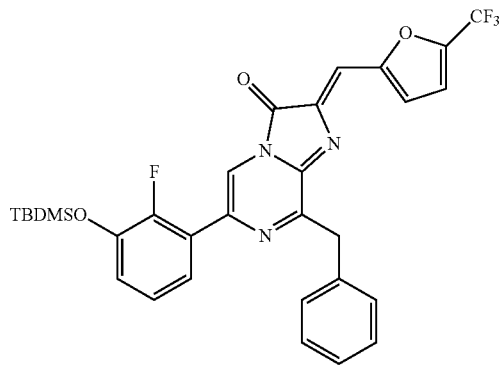

Following general procedure C, tert-butyl (Z)-2-((3-benzyl-5-bromopyrazin-2-yl)amino)-3-(5-(trifluoromethyl)furan-2-yl)acrylate (0.130 g, 0.25 mmol) was reacted with tert-butyl(2-fluoro-3-(4,4,5,5-tetramethyl-1,3,2-dioxaborolan-2-yl)phenoxy)dimethylsilane (0.13 g, 0.37 mmol) to afford the desired product (0.12 g, 75%) as a light brown foam. ESI MS m/z 700 [M+H]+.

Following general procedure E, (Z)-2-((3-benzyl-5-(3-((tert-butyldimethylsilyl)oxy)-2-fluorophenyl)pyrazin-2-yl)amino)-3-(5-(trifluoromethyl)furan-2-yl)acrylic acid (0.19 mmol) was reacted with di(1H-imidazol-1-yl)methanone (0.060 g, 0.37 mmol) to afford the crude product as a purple solid. ESI MS m/z 596 [M+H]+.

Step 2. (Z)-2-((3-benzyl-5-(3-((tert-butyldimethylsilyl)oxy)-2-fluorophenyl)pyrazin-2-yl)amino)-3-(5-(trifluoromethyl)furan-2-yl)acrylic acid (JRW-1612)

Step 4. 8-benzyl-6-(3-((tert-butyldimethylsilyl)oxy)-2-fluorophenyl)-2-((5-(trifluoromethyl)furan-2-yl)methyl)imidazo[1,2-a]pyrazin-3(7H)-one (JRW-1618)

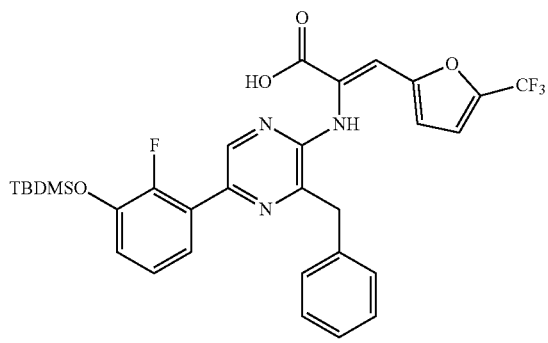 [SMILES: CC(C)(C)[Si](C)(C)Oc1cccc(-c2cnc(N/C(=C\c3ccc(C(F)(F)F)o3)C(=O)O)c(Cc3ccccc3)n2)c1F]

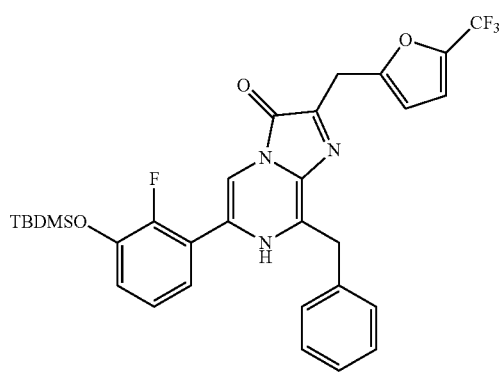 [SMILES: CC(C)(C)[Si](C)(C)Oc1cccc(-c2cn3c(=O)c(Cc4ccc(C(F)(F)F)o4)nc-3c(Cc3ccccc3)[nH]2)c1F]

Following general procedure D, tert-butyl (Z)-2-((3-benzyl-5-(3-((tert-butyldimethylsilyl)oxy)-2-fluorophenyl)pyrazin-2-yl)amino)-3-(5-(trifluoromethyl)furan-2-yl)acrylate (0.12 g, 0.19 mmol) was reacted with trifluoroacetic acid (1 mL) to afford the crude product as a red oil. ESI MS m/z 614 [M+H]+.

Following general procedure F, (Z)-8-benzyl-6-(3-((tert-butyldimethylsilyl)oxy)-2-fluorophenyl)-2-((5-(trifluoromethyl)furan-2-yl)methylene)imidazo[1,2-a]pyrazin-3(2H)-one (0.19 mmol) was reacted with sodium borohydride (0.035 g, 0.93 mmol) to afford the crude product as a yellow solid. ESI MS m/z 598 [M+H]+.

Step 5. 8-benzyl-6-(2-fluoro-3-hydroxyphenyl)-2-((5-(trifluoromethyl)furan-2-yl)methyl)imidazo[1,2-a]pyrazin-3(7H)-one (JRW-1619)

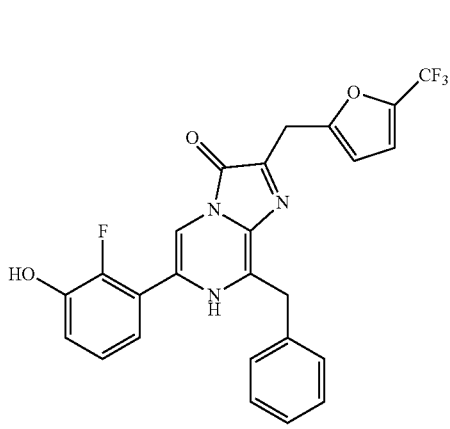 [SMILES: O=c1c(Cc2ccc(C(F)(F)F)o2)nc2c(Cc3ccccc3)[nH]c(-c3cccc(O)c3F)cn1-2]

Following general procedure G, 8-benzyl-6-(3-((tert-butyldimethylsilyl)oxy)-2-fluorophenyl)-2-((5-(trifluoromethyl)furan-2-yl)methyl)imidazo[1,2-a]pyrazin-3(7H)-one (0.19 mmol) was reacted with HCl (1 mL, 6M) to afford the desired product (0.059 g, 66% over 4 steps). $^1$H NMR (400 MHz, Methanol-d4) δ 7.71 (s, 1H), 7.48-7.39 (m, 2H), 7.36-7.21 (m, 3H), 7.16-6.98 (m, 3H), 6.92-6.88 (m, 1H), 6.38-6.28 (m, 1H), 4.42 (s, 2H), 4.29 (s, 2H); ESI MS m/z 484 [M+H]$^+$.

Example 29. 8-benzyl-6-(2-fluoro-3-hydroxyphenyl)-2-(thiophen-2-ylmethyl)imidazo[1,2-a]pyrazin-3(7H)-one (JRW-1624)

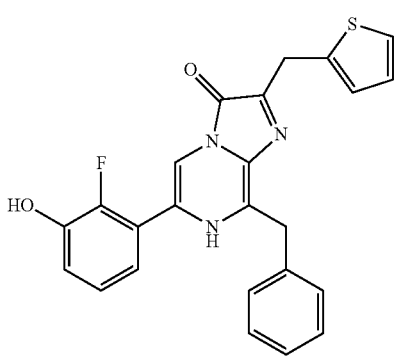 [SMILES: O=c1c(Cc2cccs2)nc2c(Cc3ccccc3)[nH]c(-c3cccc(O)c3F)cn1-2]

Step 1. Tert-butyl (Z)-2-((3-benzyl-5-bromopyrazin-2-yl)amino)-3-(thiophen-2-yl)acrylate (JRW-1595)

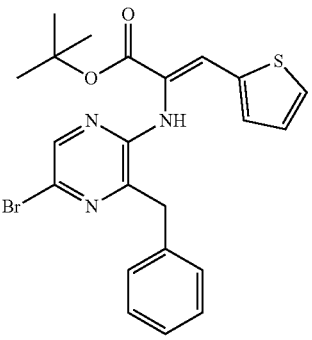

Following general procedure B, tert-butyl 2-((3-benzyl-5-bromopyrazin-2-yl)amino)-2-(diethoxyphosphoryl)acetate (0.32 g, 0.62 mmol) was reacted with thiophene-2-carbaldehyde (0.084 g, 0.75 mmol) to afford the desired product (0.24 g, 83%) as a pink solid. ESI MS m/z 473 [M+H]$^+$.

Step 2. Tert-butyl (Z)-2-((3-benzyl-5-(3-((tert-butyldimethylsilyl)oxy)-2-fluorophenyl)pyrazin-2-yl)amino)-3-(thiophen-2-yl)acrylate (JRW-1613)

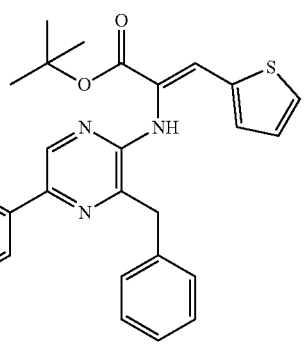

Following general procedure C, tert-butyl (Z)-2-((3-benzyl-5-bromopyrazin-2-yl)amino)-3-(thiophen-2-yl)acrylate (0.10 g, 0.21 mmol) was reacted with tert-butyl(2-fluoro-3-(4,4,5,5-tetramethyl-1,3,2-dioxaborolan-2-yl)phenoxy)dimethylsilane (0.11 g, 0.32 mmol) to afford the desired product (0.10 g, 77%) as a yellow oil. ESI MS m/z 618 [M+H]$^+$.

Step 3. (Z)-2-((3-benzyl-5-(3-((tert-butyldimethylsilyl)oxy)-2-fluorophenyl)pyrazin-2-yl)amino)-3-(thiophen-2-yl)acrylic acid (JRW-1616)

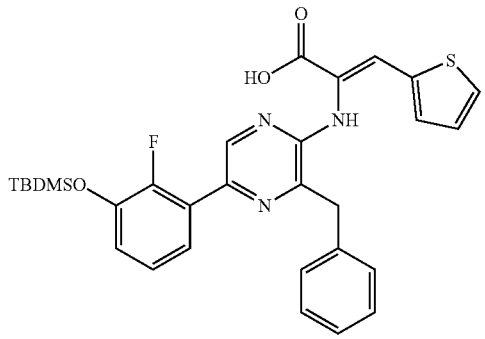

Following general procedure D, tert-butyl (Z)-2-((3-benzyl-5-(3-((tert-butyldimethylsilyl)oxy)-2-fluorophenyl)pyrazin-2-yl)amino)-3-(thiophen-2-yl)acrylate (0.10 g, 0.16 mmol) was reacted with trifluoroacetic acid (1 mL) to afford the crude product as an orange glass. ESI MS m/z 562 [M+H]$^+$.

Step 4. (Z)-8-benzyl-6-(3-((tert-butyldimethylsilyl)oxy)-2-fluorophenyl)-2-(thiophen-2-ylmethylene)imidazo[1,2-a]pyrazin-3(2H)-one (JRW-1620)

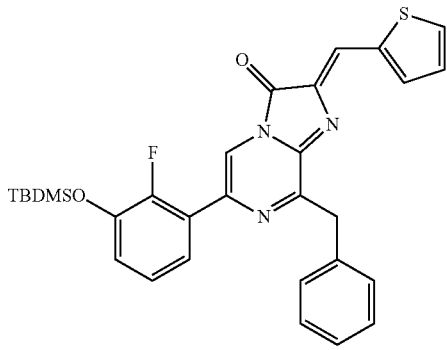

Following general procedure E, (Z)-2-((3-benzyl-5-(3-((tert-butyldimethylsilyl)oxy)-2-fluorophenyl)pyrazin-2-yl)amino)-3-(thiophen-2-yl)acrylic acid (0.16 mmol) was reacted with di(1H-imidazol-1-yl)methanone (0.052 g, 0.32 mmol) to afford the crude product as a red solid. ESI MS m/z 544 [M+H]$^+$.

Step 5. 8-benzyl-6-(3-((tert-butyldimethylsilyl)oxy)-2-fluorophenyl)-2-(thiophen-2-ylmethyl)imidazo[1,2-a]pyrazin-3(7H)-one (JRW-1622)

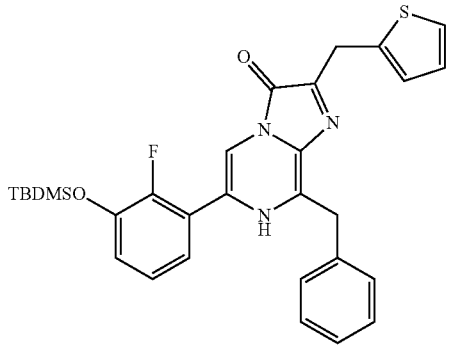

Following general procedure F, (Z)-8-benzyl-6-(3-((tert-butyldimethylsilyl)oxy)-2-fluorophenyl)-2-(thiophen-2-ylmethylene)imidazo[1,2-a]pyrazin-3(2H)-one (0.16 mmol) was reacted with sodium borohydride (0.030 g, 0.80 mmol) to afford the crude product. ESI MS m/z 546 [M+H]$^+$.

Step 6. 8-benzyl-6-(2-fluoro-3-hydroxyphenyl)-2-(thiophen-2-ylmethyl)imidazo[1,2-a]pyrazin-3(7H)-one (JRW-1624)

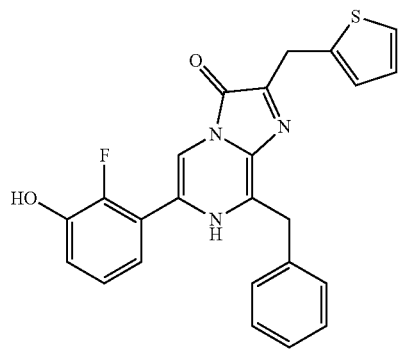 [SMILES: O=c1c(Cc2cccs2)nc2c(Cc3ccccc3)[nH]c(-c3cccc(O)c3F)cn1-2]

Following general procedure G, 8-benzyl-6-(3-((tert-butyldimethylsilyl)oxy)-2-fluorophenyl)-2-(thiophen-2-ylmethyl)imidazo[1,2-a]pyrazin-3(7H)-one (0.16 mmol) was reacted with HCl (1 mL, 6M) to afford the desired product (0.042 g, 61% over 4 steps). $^1$H NMR (400 MHz, Methanol-d4) δ 7.69 (s, 1H), 7.48-7.39 (m, 2H), 7.36-7.20 (m, 4H), 7.15-7.00 (m, 3H), 7.00-6.90 (m, 2H), 4.41 (s, 2H), 4.39 (s, 2H); ESI MS m/z 432 [M+H]$^+$.

Example 30. 8-benzyl-6-(2-fluoro-3-hydroxyphenyl)-2-(4-fluorobenzyl)imidazo[1,2-a]pyrazin-3(7H)-one (JRW-1634)

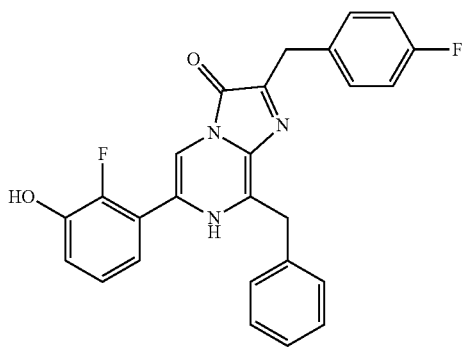 [SMILES: O=c1c(Cc2ccc(F)cc2)nc2c(Cc3ccccc3)[nH]c(-c3cccc(O)c3F)cn1-2]

Step 1. Tert-butyl (Z)-2-((3-benzyl-5-bromopyrazin-2-yl)amino)-3-(4-fluorophenyl)acrylate (JRW-1596)

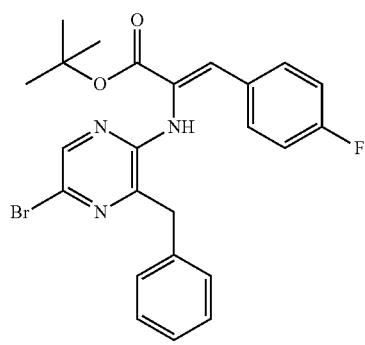 [SMILES: CC(C)(C)OC(=O)/C(=C/c1ccc(F)cc1)Nc1ncc(Br)nc1Cc1ccccc1]

Following general procedure B, tert-butyl 2-((3-benzyl-5-bromopyrazin-2-yl)amino)-2-(diethoxyphosphoryl)acetate (0.32 g, 0.62 mmol) was reacted with 4-fluorobenzaldehyde (0.093 g, 0.75 mmol) to afford the desired product (0.22 g, 73%) as a light red solid. ESI MS m/z 485 [M+H]$^+$.

Step 2. Tert-butyl (Z)-2-((3-benzyl-5-(3-((tert-butyldimethylsilyl)oxy)-2-fluorophenyl)pyrazin-2-yl)amino)-3-(4-fluorophenyl)acrylate (JRW-1626)

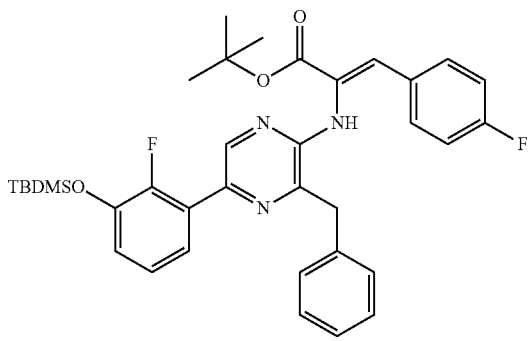 [SMILES: CC(C)(C)OC(=O)/C(=C/c1ccc(F)cc1)Nc1ncc(-c2cccc(O[Si](C)(C)C(C)(C)C)c2F)nc1Cc1ccccc1]

Following general procedure C, tert-butyl (Z)-2-((3-benzyl-5-bromopyrazin-2-yl)amino)-3-(4-fluorophenyl)acrylate (0.10 g, 0.21 mmol) was reacted with tert-butyl(2-fluoro-3-(4,4,5,5-tetramethyl-1,3,2-dioxaborolan-2-yl)phenoxy)dimethylsilane (0.11 g, 0.31 mmol) to afford the desired product (0.080 g, 61%) as a white foam. ESI MS m/z 630 [M+H]$^+$.

Step 3. (Z)-2-((3-benzyl-5-(3-((tert-butyldimethylsilyl)oxy)-2-fluorophenyl)pyrazin-2-yl)amino)-3-(4-fluorophenyl)acrylic acid (JRW-1628)

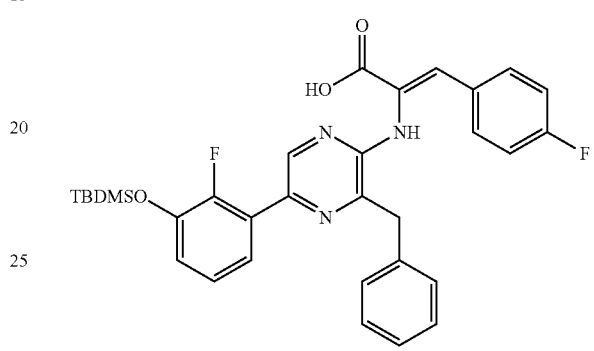

Following general procedure D, tert-butyl (Z)-2-((3-benzyl-5-(3-((tert-butyldimethylsilyl)oxy)-2-fluorophenyl)pyrazin-2-yl)amino)-3-(4-fluorophenyl)acrylate (0.080 g, 0.13 mmol) was reacted with trifluoroacetic acid (1 mL) to afford the crude product as an orange gel. ESI MS m/z 574 [M+H]$^+$.

Step 4. (Z)-8-benzyl-6-(3-((tert-butyldimethylsilyl)oxy)-2-fluorophenyl)-2-(4-fluorobenzylidene)imidazo[1,2-a]pyrazin-3(2H)-one (JRW-1630)

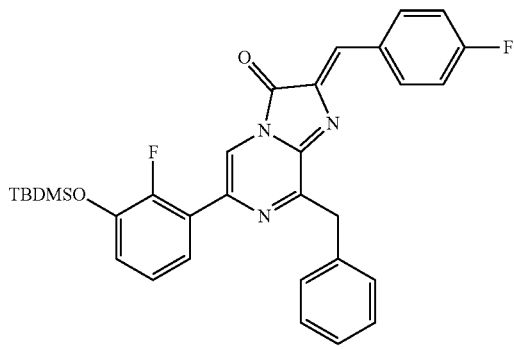 [SMILES: CC(C)(C)[Si](C)(C)Oc1cccc(C2=CN3C(=O)/C(=C/c4ccc(F)cc4)N=C3C(Cc3ccccc3)=N2)c1F]

Following general procedure E, (Z)-2-((3-benzyl-5-(3-((tert-butyldimethylsilyl)oxy)-2-fluorophenyl)pyrazin-2-yl)amino)-3-(4-fluorophenyl)acrylic acid (0.13 mmol) was reacted with di(1H-imidazol-1-yl)methanone (0.041 g, 0.25 mmol) to afford the crude product as a red solid. ESI MS m/z 556 [M+H]$^+$.

Step 5. 8-benzyl-6-(3-((tert-butyldimethylsilyl)oxy)-2-fluorophenyl)-2-(4-fluorobenzyl)imidazo[1,2-a]pyrazin-3(7H)-one (JRW-1632)

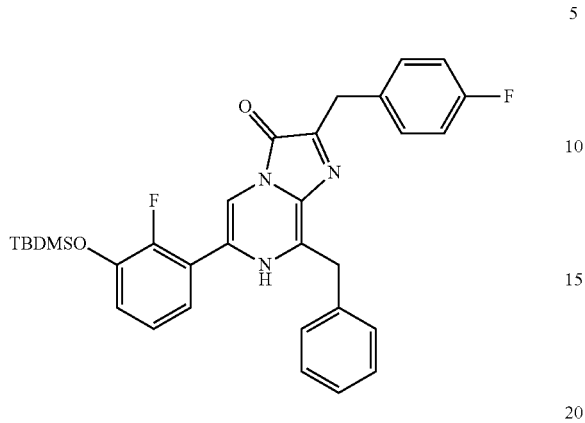

Following general procedure F, (Z)-8-benzyl-6-(3-((tert-butyldimethylsilyl)oxy)-2-fluorophenyl)-2-(4-fluorobenzylidene)imidazo[1,2-a]pyrazin-3(2H)-one (0.13 mmol) was reacted with sodium borohydride (0.024 g, 0.63 mmol) to afford the crude product as an orange oil. ESI MS m/z 558 [M+H]$^+$.

Step 6. 8-benzyl-6-(2-fluoro-3-hydroxyphenyl)-2-(4-fluorobenzyl)imidazo[1,2-a]pyrazin-3(7H)-one (JRW-1634)

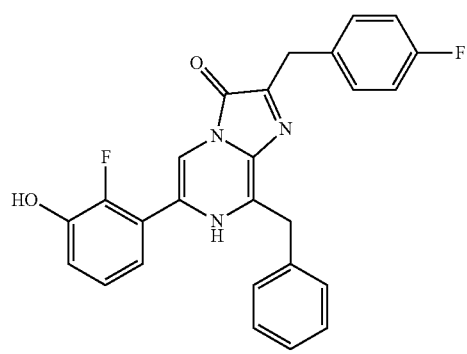 [SMILES: O=c1c(Cc2ccc(F)cc2)nc2c(Cc3ccccc3)[nH]c(-c3cccc(O)c3F)cn1-2]

Following general procedure G, 8-benzyl-6-(3-((tert-butyldimethylsilyl)oxy)-2-fluorophenyl)-2-(4-fluorobenzyl)imidazo[1,2-a]pyrazin-3(7H)-one (0.13 mmol) was reacted with HCl (1 mL, 6M) to afford the desired product (0.040 g, 71% over 4 steps). $^1$H NMR (400 MHz, Methanol-d4) δ 7.68 (s, 1H), 7.44-7.20 (m, 7H), 7.16-6.95 (m, 5H), 4.40 (s, 2H), 4.18 (s, 2H); ESI MS m/z 432 [M+H]$^+$.

Example 31. 6-(3-amino-2-fluorophenyl)-8-benzyl-2-(4-fluorobenzyl)imidazo[1,2-a]pyrazin-3(7H)-one (JRW-1635)

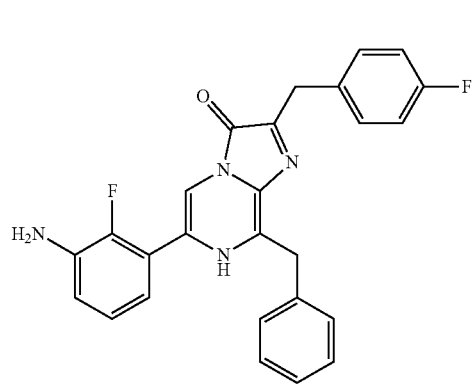

Step 1. Tert-butyl (Z)-2-((3-benzyl-5-(2-fluoro-3-nitrophenyl)pyrazin-2-yl)amino)-3-(4-fluorophenyl)acrylate (JRW-1627)

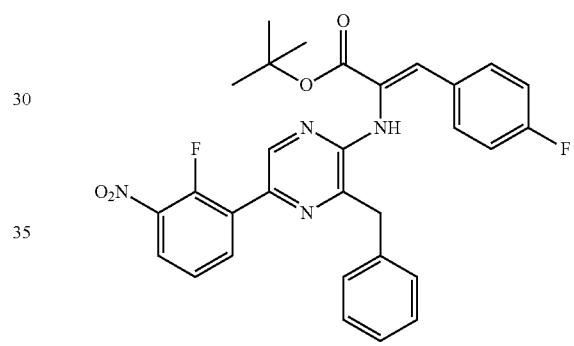

Following general procedure C, tert-butyl (Z)-2-((3-benzyl-5-bromopyrazin-2-yl)amino)-3-(4-fluorophenyl)acrylate (0.11 g, 0.23 mmol) was reacted with 2-(2-fluoro-3-nitrophenyl)-4,4,5,5-tetramethyl-1,3,2-dioxaborolane (0.091 g, 0.34 mmol) to afford the desired product (0.10 g, 81%) as a light brown solid. ESI MS m/z 545 [M+H]$^+$.

Step 2. (Z)-2-((3-benzyl-5-(2-fluoro-3-nitrophenyl)pyrazin-2-yl)amino)-3-(4-fluorophenyl)acrylic acid (JRW-1629)

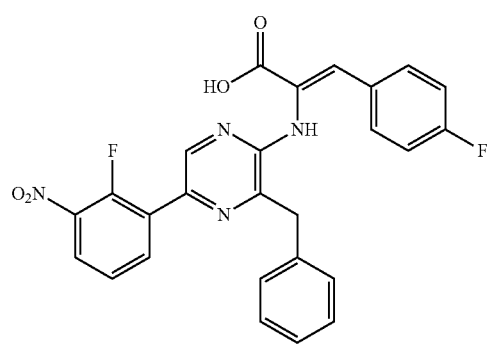 [SMILES: O=C(O)/C(=C/c1ccc(F)cc1)Nc1ncc(-c2cccc([N+](=O)[O-])c2F)nc1Cc1ccccc1]

Following general procedure D, tert-butyl (Z)-2-((3-benzyl-5-(2-fluoro-3-nitrophenyl)pyrazin-2-yl)amino)-3-(4-fluorophenyl)acrylate (0.10 g, 0.18 mmol) was reacted with trifluoroacetic acid (1 mL) to afford the crude product as an orange oil. ESI MS m/z 489 [M+H]+.

Step 3. (Z)-8-benzyl-6-(2-fluoro-3-nitrophenyl)-2-(4-fluorobenzylidene)imidazo[1,2-a]pyrazin-3(2H)-one (JRW-1631)

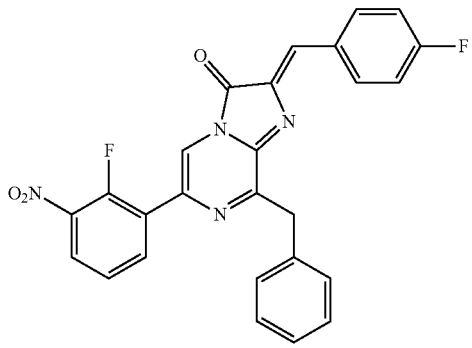 [SMILES: O=C1/C(=C/c2ccc(F)cc2)N=C2C(Cc3ccccc3)=NC(c3cccc([N+](=O)[O-])c3F)=CN12]

Following general procedure E, (Z)-2-((3-benzyl-5-(2-fluoro-3-nitrophenyl)pyrazin-2-yl)amino)-3-(4-fluorophenyl)acrylic acid (0.19 mmol) was reacted with di(1H-imidazol-1-yl)methanone (0.060 g, 0.37 mmol) to afford the crude product as a red solid. ESI MS m/z 471 [M+H]+.

Step 4. 8-benzyl-6-(2-fluoro-3-nitrophenyl)-2-(4-fluorobenzyl)imidazo[1,2-a]pyrazin-3(7H)-one (JRW-1633)

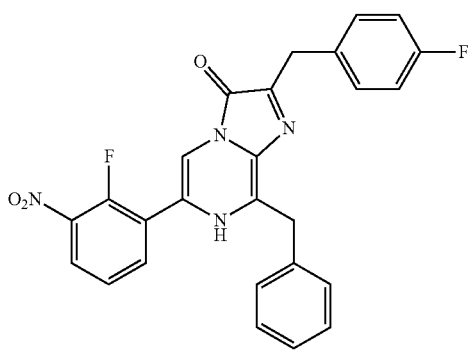 [SMILES: O=c1c(Cc2ccc(F)cc2)nc2c(Cc3ccccc3)[nH]c(-c3cccc([N+](=O)[O-])c3F)cn1-2]

Following general procedure F, (Z)-8-benzyl-6-(2-fluoro-3-nitrophenyl)-2-(4-fluorobenzylidene)imidazo[1,2-a]pyrazin-3(2H)-one (0.19 mmol) was reacted with sodium borohydride (0.035 g, 0.93 mmol) to afford the crude product. ESI MS m/z 473 [M+H]+.

Step 5. 6-(3-amino-2-fluorophenyl)-8-benzyl-2-(4-fluorobenzyl)imidazo[1,2-a]pyrazin-3(7H)-one (JRW-1635)

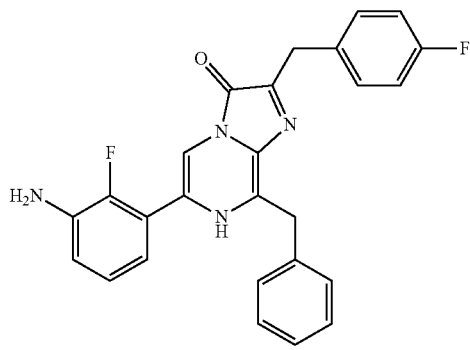

Following general procedure H, 8-benzyl-6-(2-fluoro-3-nitrophenyl)-2-(4-fluorobenzyl)imidazo[1,2-a]pyrazin-3(7H)-one (0.19 mmol) was reacted with hydrogen (1 atm) to obtain the desired product (0.029 g, 35% over 4 steps) as an orange solid. $^1$H NMR (400 MHz, Methanol-d4) δ 7.64 (s, 1H), 7.45-7.34 (m, 4H), 7.34-7.20 (m, 3H), 7.07-6.91 (m, 4H), 6.88-6.77 (m, 1H), 4.40 (s, 2H), 4.18 (s, 2H); ESI MS m/z 443 [M+H]+.

Example 32. 6-(3-amino-2-methylphenyl)-8-benzyl-2-(furan-2-ylmethyl)imidazo[1,2-a]pyrazin-3(7H)-one (JRW-1642)

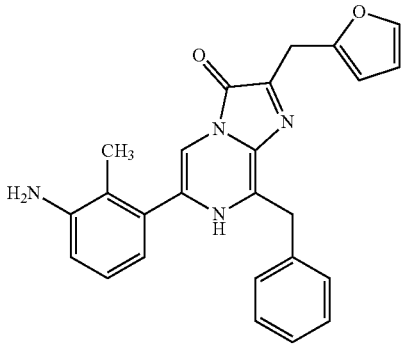

Step 1. Tert-butyl (Z)-2-((3-benzyl-5-(2-methyl-3-nitrophenyl)pyrazin-2-yl)amino)-3-(furan-2-yl)acrylate (JRW-1637)

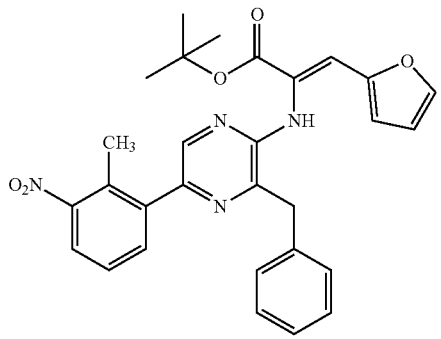 [SMILES: Cc1c(-c2cnc(N/C(=C\c3ccco3)C(=O)OC(C)(C)C)c(Cc3ccccc3)n2)cccc1[N+](=O)[O-]]

Following general procedure C, tert-butyl (Z)-2-((3-benzyl-5-bromopyrazin-2-yl)amino)-3-(furan-2-yl)acrylate (0.13 g, 0.28 mmol) was reacted with 4,4,5,5-tetramethyl-2-(2-methyl-3-nitrophenyl)-1,3,2-dioxaborolane (0.11 g, 0.42 mmol) to afford the desired product (0.14 g, 98%) as a light orange solid. ESI MS m/z 513 [M+H]$^+$.

Step 2. (Z)-2-((3-benzyl-5-(2-methyl-3-nitrophenyl)pyrazin-2-yl)amino)-3-(furan-2-yl)acrylic acid (JRW-1639)

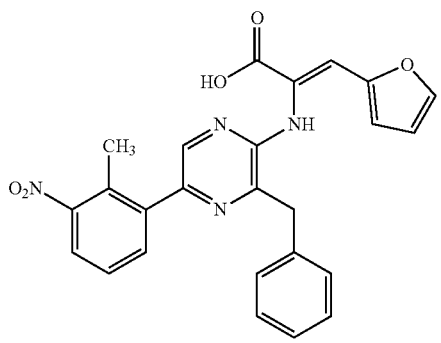 [SMILES: Cc1c(-c2cnc(N/C(=C\c3ccco3)C(=O)O)c(Cc3ccccc3)n2)cccc1[N+](=O)[O-]]

Following general procedure D, tert-butyl (Z)-2-((3-benzyl-5-(2-methyl-3-nitrophenyl)pyrazin-2-yl)amino)-3-(furan-2-yl)acrylate (0.14 g, 0.27 mmol) was reacted with trifluoroacetic acid (1 mL) to afford the crude product as an orange oil. ESI MS m/z 457 [M+H]$^+$.

Step 3. (Z)-8-benzyl-2-(furan-2-ylmethylene)-6-(2-methyl-3-nitrophenyl)imidazo[1,2-a]pyrazin-3(2H)-one (JRW-1640)

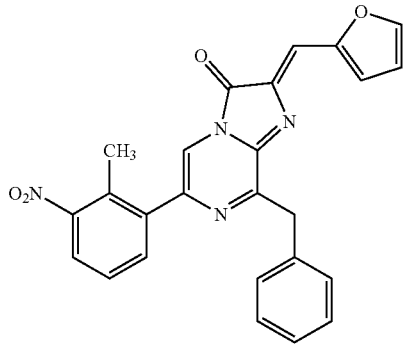

Following general procedure E, (Z)-2-((3-benzyl-5-(2-methyl-3-nitrophenyl)pyrazin-2-yl)amino)-3-(furan-2-yl) acrylic acid (0.27 mmol) was reacted with di(1H-imidazol-1-yl)methanone (0.087 g, 0.54 mmol) to afford the crude product. ESI MS m/z 439 [M+H]$^+$.

Step 4. 8-benzyl-2-(furan-2-ylmethyl)-6-(2-methyl-3-nitrophenyl)imidazo[1,2-a]pyrazin-3(7H)-one (JRW-1641)

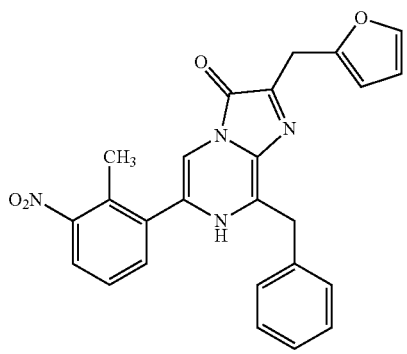

Following general procedure F, (Z)-8-benzyl-2-(furan-2-ylmethylene)-6-(2-methyl-3-nitrophenyl)imidazo[1,2-a]pyrazin-3(2H)-one (0.27 mmol) was reacted with sodium borohydride (0.051 g, 1.3 mmol) to afford the crude product. ESI MS m/z 441 [M+H]$^+$.

Step 5. 6-(3-amino-2-methylphenyl)-8-benzyl-2-(furan-2-ylmethyl)imidazo[1,2-a]pyrazin-3(7H)-one (JRW-1642)

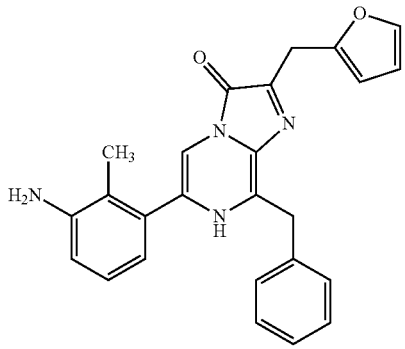 [SMILES: Cc1c(-c2cn3c(=O)c(Cc4ccco4)nc-3c(Cc3ccccc3)[nH]2)cccc1[N+](=O)[O-]]

Following general procedure H, 8-benzyl-2-(furan-2-yl-methyl)-6-(2-methyl-3-nitrophenyl)imidazo[1,2-a]pyrazin-3(7H)-one (0.27 mmol) was reacted with hydrogen (1 atm) to obtain the desired product (0.061 g, 55% over 4 steps) as a brown orange solid. $^1$H NMR (400 MHz, Methanol-d4) δ 7.45-7.35 (m, 4H), 7.35-7.20 (m, 3H), 7.07 (t, J=7.8 Hz, 1H), 6.87 (dd, 1=7.8, 1.3 Hz, 1H), 6.74 (dd, J=7.4, 1.3 Hz, 1H), 6.35 (dd, 1=3.2, 1.9 Hz, 1H), 6.15 (dd, J=3.2, 1.0 Hz, 1H), 4.37 (s, 2H), 4.23 (s, 2H), 1.97 (s, 3H); ESI MS m/z 411 [M+H]$^+$.

Example 33. 8-benzyl-2-(furan-2-ylmethyl)-6-(3-hydroxy-2-methylphenyl)imidazo[1,2-a]pyrazin-3(7H)-one (JRW-1645)

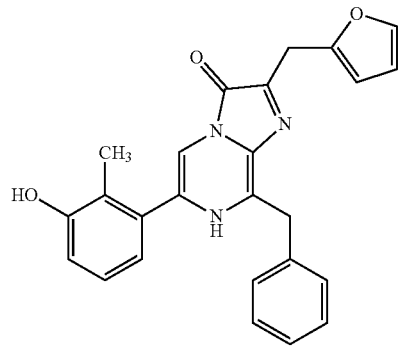 [SMILES: Cc1c(O)cccc1-c1cn2c(=O)c(Cc3ccco3)nc-2c(Cc2ccccc2)[nH]1]

Step 1. Tert-butyl (Z)-2-((3-benzyl-5-(3-hydroxy-2-methylphenyl)pyrazin-2-yl)amino)-3-(furan-2-yl)acrylate (JRW-1636)

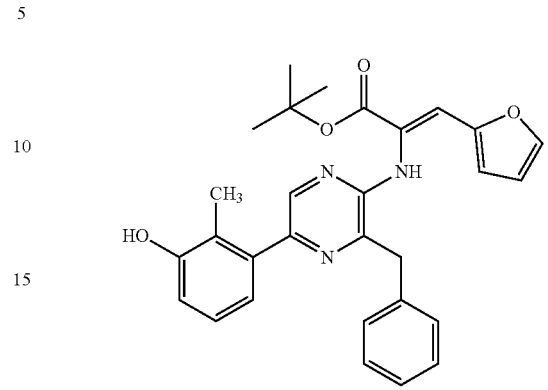

Following general procedure C, tert-butyl (Z)-2-((3-benzyl-5-bromopyrazin-2-yl)amino)-3-(furan-2-yl)acrylate (0.19 g, 0.42 mmol) was reacted with 2-methyl-3-(4,4,5,5-tetramethyl-1,3,2-dioxaborolan-2-yl)phenol (0.14 g, 0.62 mmol) to afford the desired product (0.17 g, 84%) as a light red foam. ESI MS m/z 484 [M+H]$^+$.

Step 2. (Z)-2-((3-benzyl-5-(3-hydroxy-2-methylphenyl)pyrazin-2-yl)amino)-3-(furan-2-yl)acrylic acid (JRW-1643)

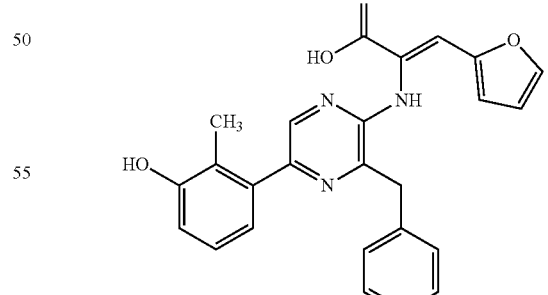

Following general procedure D, tert-butyl (Z)-2-((3-benzyl-5-(3-hydroxy-2-methylphenyl)pyrazin-2-yl)amino)-3-(furan-2-yl)acrylate (0.35 mmol) was reacted with trifluoroacetic acid (1 mL) to afford the crude product as a brown orange oil. ESI MS m/z 428 [M+H]$^+$.

Step 3. (Z)-8-benzyl-2-(furan-2-ylmethylene)-6-(3-hydroxy-2-methylphenyl)imidazo[1,2-a]pyrazin-3(2H)-one (JRW-1644)

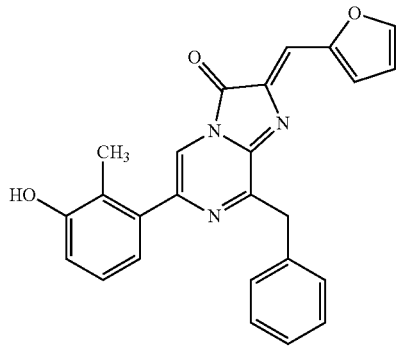 [SMILES: Cc1c(O)cccc1C1=CN2C(=O)/C(=C/c3ccco3)N=C2C(Cc2ccccc2)=N1]

Following general procedure E, (Z)-2-((3-benzyl-5-(3-hydroxy-2-methylphenyl)pyrazin-2-yl)amino)-3-(furan-2-yl)acrylic acid (0.35 mmol) was reacted with di(1H-imidazol-1-yl)methanone (0.056 g, 0.35 mmol) to afford the crude product as a red solid. ESI MS m/z 410 [M+H]⁺.

Step 4. 8-benzyl-2-(furan-2-ylmethyl)-6-(3-hydroxy-2-methylphenyl)imidazo[1,2-a]pyrazin-3(7H)-one (JRW-1645)

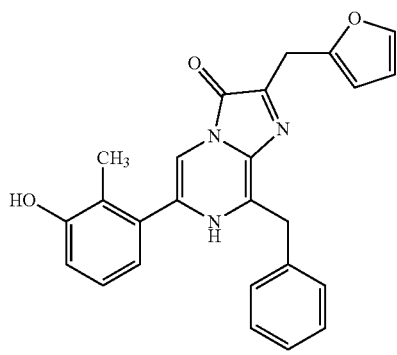 [SMILES: Cc1c(O)cccc1-c1cn2c(=O)c(Cc3ccco3)nc-2c(Cc2ccccc2)[nH]1]

Following general procedure F, (Z)-8-benzyl-2-(furan-2-ylmethylene)-6-(3-hydroxy-2-methylphenyl)imidazo[1,2-a]pyrazin-3(2H)-one (0.35 mmol) was reacted with sodium borohydride (0.066 g, 1.7 mmol) to afford the desired product (0.10 g, 71% over three steps). ¹H NMR (400 MHz, Methanol-d4) δ 7.45-7.35 (m, 4H), 7.35-7.20 (m, 3H), 7.12 (t, J=7.8 Hz, 1H), 6.94-6.83 (m, 2H), 6.35 (dd, J=3.2, 1.9 Hz, 1H), 6.15 (dd, J=3.2, 1.0 Hz, 1H), 4.37 (s, 2H), 4.23 (s, 2H), 2.03 (s, 3H); ESI MS m/z 412 [M+H]⁺.

Example 34. 6-(3-amino-2-fluorophenyl)-8-(2-fluorobenzyl)-2-(furan-2-ylmethyl)imidazo[1,2-a]pyrazin-3(7H)-one (JRW-1667)

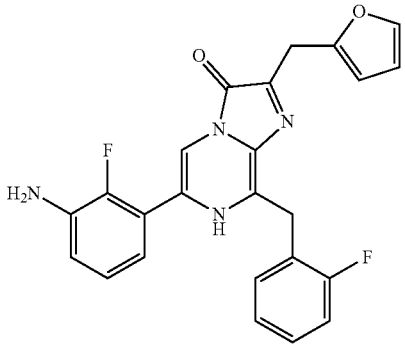

Step 1. 5-bromo-3-(2-fluorobenzyl)pyrazin-2-amine (JRW-1648)

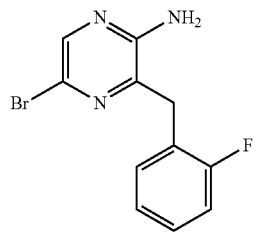 [SMILES: Nc1ncc(Br)nc1Cc1ccccc1F]

A suspension of zinc dust (5.2 g, 79.4 mmol) in HCl (20 mL, 1M) was stirred for 10 min. The solid was filtered, washed with methanol and THF, transferred to a flask, and dried under vacuum for 18 h. A solution of 1-(bromomethyl)-2-fluorobenzene (5.0 g, 26.5 mmol) in THF (50 mL) was added to the zinc dust. The mixture was heated to reflux for 2 h, then cooled, and allow to settle. The supernatant was added to a solution of 3,5-dibromopyrazin-2-amine (3.0 g, 12.0 mmol) and bis(triphenylphosphine)palladium(II) dichloride (0.42 g, 0.60 mmol) in THF (50 mL). The suspension was heated to 50° C. for 18 h. The mixture was diluted with ethyl acetate and water, and the aqueous layer was extracted with ethyl acetate. The organic layers were combined, dried with sodium sulfate, filtered, concentrated, and purified with silica gel chromatography to obtain the desired product (1.3 g, 38%) as a light yellow solid. ESI MS m/z 283 [M+H]⁺.

Step 2. Tert-butyl 2-((5-bromo-3-(2-fluorobenzyl)pyrazin-2-yl)amino)-2-(diethoxyphosphoryl)acetate (JRW-1652)

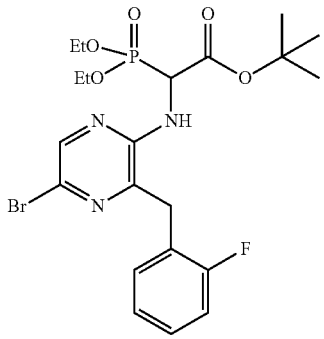 [SMILES: CCOP(=O)(OCC)C(Nc1ncc(Br)nc1Cc1ccccc1F)C(=O)OC(C)(C)C]

Following general procedure A, 5-bromo-3-(2-fluorobenzyl)pyrazin-2-amine (1.3 g, 4.6 mmol) was reacted with tert-butyl 2-diazo-2-(diethoxyphosphoryl)acetate (1.9 g, 6.9 mmol) to afford the desired product (2.2 g, 87%) as a brown solid. ESI MS m/z 533 [M+H]$^+$.

Step 3. Tert-butyl (Z)-2-((5-bromo-3-(2-fluorobenzyl)pyrazin-2-yl)amino)-3-(furan-2-yl)acrylate (TV-1301)

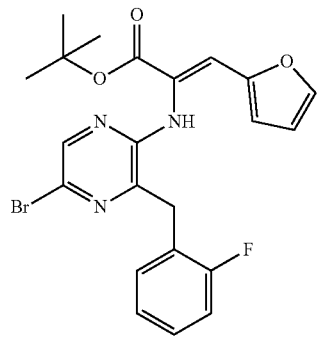 [SMILES: CC(C)(C)OC(=O)/C(=C/c1ccco1)Nc1ncc(Br)nc1Cc1ccccc1F]

Following general procedure B, tert-butyl 2-((5-bromo-3-(2-fluorobenzyl)pyrazin-2-yl)amino)-2-(diethoxyphosphoryl)acetate (1.1 g, 2.1 mmol) was reacted with furfural (0.25 g, 2.6 mmol) to afford the desired product (0.61 g, 61%) as a yellow oil. ESI MS m/z 475 [M+H]$^+$.

Step 4. Tert-butyl (Z)-2-((5-(2-fluoro-3-nitrophenyl)-3-(2-fluorobenzyl)pyrazin-2-yl)amino)-3-(furan-2-yl)acrylate (JRW-1657)

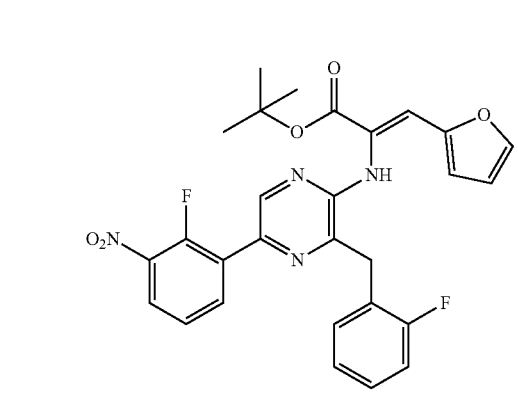 [SMILES: CC(C)(C)OC(=O)/C(=C/c1ccco1)Nc1ncc(-c2cccc([N+](=O)[O-])c2F)nc1Cc1ccccc1F]

Following general procedure C, tert-butyl (Z)-2-((5-bromo-3-(2-fluorobenzyl)pyrazin-2-yl)amino)-3-(furan-2-yl)acrylate (0.20 g, 0.42 mmol) was reacted with 2-(2-fluoro-3-nitrophenyl)-4,4,5,5-tetramethyl-1,3,2-dioxaborolane (0.17 g, 0.63 mmol) to afford the desired product (0.14 g, 62%) as an orange foam. ESI MS m/z 535 [M+H]$^+$.

Step 5. (Z)-2-((5-(2-fluoro-3-nitrophenyl)-3-(2-fluorobenzyl)pyrazin-2-yl)amino)-3-(furan-2-yl)acrylic acid (JRW-1659)

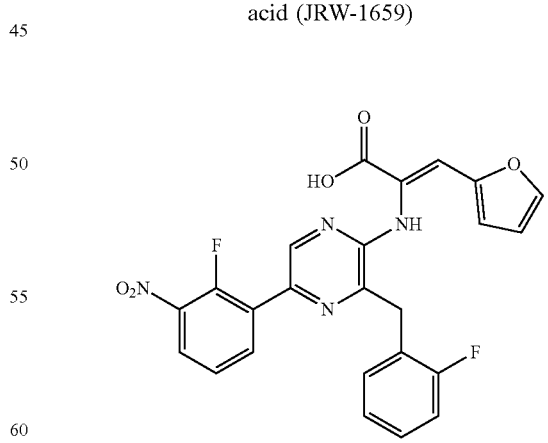

Following general procedure D, tert-butyl (Z)-2-((5-(2-fluoro-3-nitrophenyl)-3-(2-fluorobenzyl)pyrazin-2-yl)amino)-3-(furan-2-yl)acrylate (0.14 g, 0.26 mmol) was reacted with trifluoroacetic acid (1 mL) to afford the crude product as a brown oil. ESI MS m/z 479 [M+H]$^+$.

Step 6. (Z)-6-(2-fluoro-3-nitrophenyl)-8-(2-fluorobenzyl)-2-(furan-2-ylmethylene)imidazo[1,2-a]pyrazin-3(2H)-one (JRW-1661)

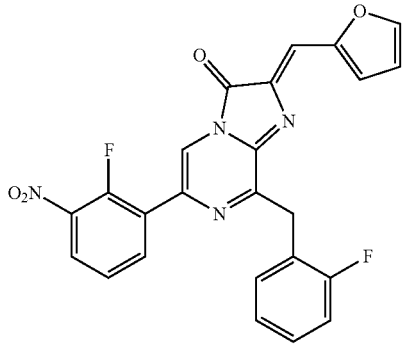 [SMILES: O=C1/C(=C/c2ccco2)N=C2C(Cc3ccccc3F)=NC(c3cccc([N+](=O)[O-])c3F)=CN12]

Following general procedure E, (Z)-2-((5-(2-fluoro-3-nitrophenyl)-3-(2-fluorobenzyl)pyrazin-2-yl)amino)-3-(furan-2-yl)acrylic acid (0.26 mmol) was reacted with di(1H-imidazol-1-yl)methanone (0.084 g, 0.52 mmol) to afford the crude product as a red solid. ESI MS m/z 461 [M+H]$^+$.

Step 7. 6-(2-fluoro-3-nitrophenyl)-8-(2-fluorobenzyl)-2-(furan-2-ylmethyl)imidazo[1,2-a]pyrazin-3(7H)-one (JRW-1663)

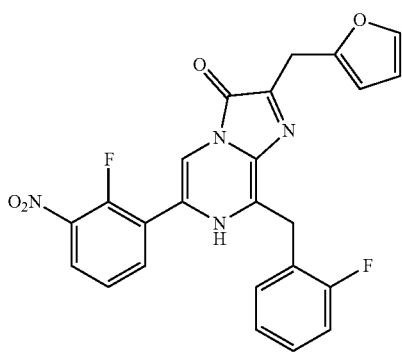 [SMILES: Nc1cccc(-c2cn3c(=O)c(Cc4ccco4)nc-3c(Cc3ccccc3F)[nH]2)c1F]

Following general procedure F, (Z)-6-(2-fluoro-3-nitrophenyl)-8-(2-fluorobenzyl)-2-(furan-2-ylmethylene)imidazo[1,2-a]pyrazin-3(2H)-one (0.26 mmol) was reacted with sodium borohydride (0.049 g, 1.3 mmol) to afford the crude product. ESI MS m/z 463 [M+H]$^+$.

Step 8. 6-(3-amino-2-fluorophenyl)-8-(2-fluorobenzyl)-2-(furan-2-ylmethyl)imidazo[1,2-a]pyrazin-3(7H)-one (JRW-1667)

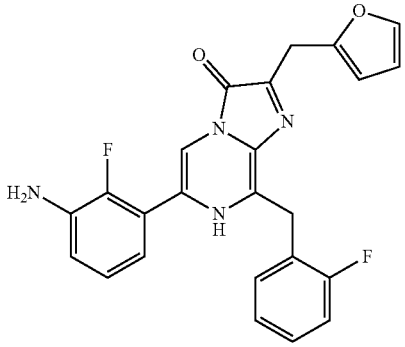

Following general procedure H, 6-(2-fluoro-3-nitrophenyl)-8-(2-fluorobenzyl)-2-(furan-2-ylmethyl)imidazo[1,2-a]pyrazin-3(7H)-one (0.26 mmol) was reacted with hydrogen (1 atm) to obtain the desired product (0.023 g, 20% over 4 steps) as an orange brown foam. $^1$H NMR (400 MHz, Methanol-d4) δ 7.81 (s, 1H), 7.39 (d, J=1.8 Hz, 1H), 7.36-7.25 (m, 2H), 7.19-7.08 (m, 2H), 7.06-6.81 (m, 3H), 6.33 (dd, J=3.2, 1.9 Hz, 1H), 6.11 (dd, J=3.2, 1.0 Hz, 1H), 4.49 (s, 2H), 4.20 (s, 2H); ESI MS m/z 433 [M+H]$^+$.

Example 35. 6-(2-fluoro-3-hydroxyphenyl)-8-(2-fluorobenzyl)-2-(furan-2-ylmethyl)imidazo[1,2-a]pyrazin-3(7H)-one (JRW-1668)

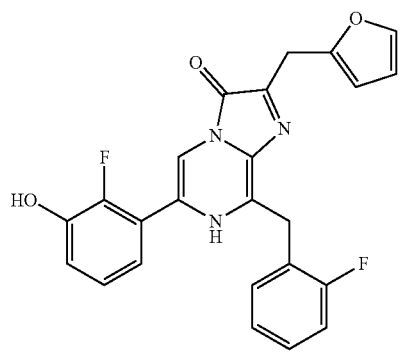

Step 1. Tert-butyl (Z)-2-((5-(3-((tert-butyldimethyl-silyl)oxy)-2-fluorophenyl)-3-(2-fluorobenzyl)pyrazin-2-yl)amino)-3-(furan-2-yl)acrylate (JRW-1658)

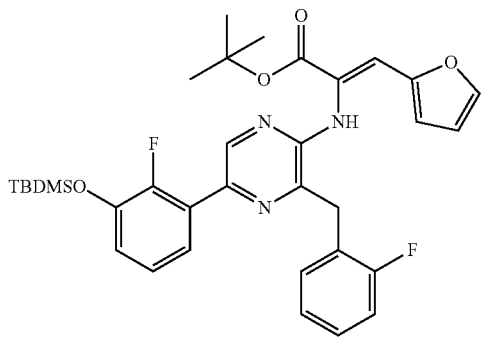 [SMILES: CC(C)(C)OC(=O)/C(=C/c1ccco1)Nc1ncc(-c2cccc(O[Si](C)(C)C(C)(C)C)c2F)nc1Cc1ccccc1F]

Following general procedure C, tert-butyl (Z)-2-((5-bromo-3-(2-fluorobenzyl)pyrazin-2-yl)amino)-3-(furan-2-yl)acrylate (0.20 g, 0.42 mmol) was reacted with tert-butyl (2-fluoro-3-(4,4,5,5-tetramethyl-1,3,2-dioxaborolan-2-yl)phenoxy)dimethylsilane (0.22 g, 0.63 mmol) to afford the desired product (0.21 g, 80%) as an orange oil. ESI MS m/z 620 [M+H]$^+$.

Step 2. (Z)-2-((5-(3-((tert-butyldimethylsilyl)oxy)-2-fluorophenyl)-3-(2-fluorobenzyl)pyrazin-2-yl)amino)-3-(furan-2-yl)acrylic acid (JRW-1660)

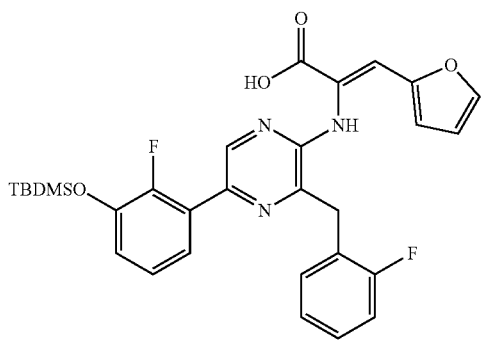 [SMILES: CC(C)(C)[Si](C)(C)Oc1cccc(-c2cnc(N/C(=C\c3ccco3)C(=O)O)c(Cc3ccccc3F)n2)c1F]

Following general procedure D, tert-butyl (Z)-2-((5-(3-((tert-butyldimethylsilyl)oxy)-2-fluorophenyl)-3-(2-fluorobenzyl)pyrazin-2-yl)amino)-3-(furan-2-yl)acrylate (0.21 g, 0.34 mmol) was reacted with trifluoroacetic acid (1 mL) to afford the crude product as a red oil. ESI MS m/z 564 [M+H]$^+$.

Step 3. (Z)-6-(3-((tert-butyldimethylsilyl)oxy)-2-fluorophenyl)-8-(2-fluorobenzyl)-2-(furan-2-ylmethylene)imidazo[1,2-a]pyrazin-3(2H)-one (JRW-1662)

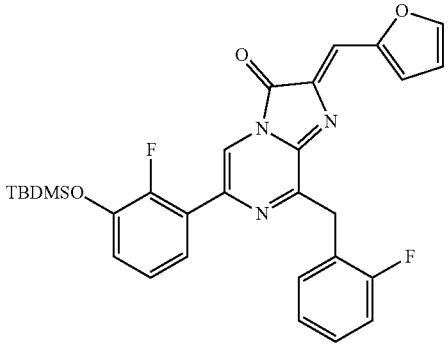 [SMILES: CC(C)(C)[Si](C)(C)Oc1cccc(C2=CN3C(=O)/C(=C/c4ccco4)N=C3C(Cc3ccccc3F)=N2)c1F]

Following general procedure E, (Z)-2-((5-(3-((tert-butyldimethylsilyl)oxy)-2-fluorophenyl)-3-(2-fluorobenzyl)pyrazin-2-yl)amino)-3-(furan-2-yl)acrylic acid (0.34 mmol) was reacted with di(1H-imidazol-1-yl)methanone (0.11 g, 0.67 mmol) to afford the crude product as a red solid. ESI MS m/z 546 [M+H]$^+$.

Step 4. 6-(3-((tert-butyldimethylsilyl)oxy)-2-fluorophenyl)-8-(2-fluorobenzyl)-2-(furan-2-ylmethyl)imidazo[1,2-a]pyrazin-3(7H)-one (JRW-1664)

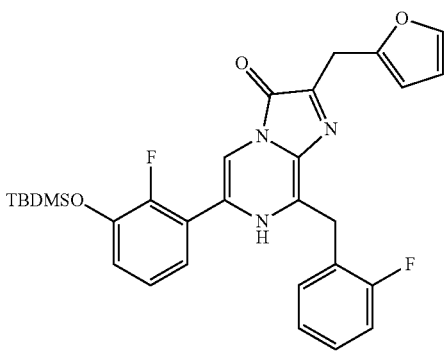 [SMILES: CC(C)(C)[Si](C)(C)Oc1cccc(-c2cn3c(=O)c(Cc4ccco4)nc-3c(Cc3ccccc3F)[nH]2)c1F]

Following general procedure F, (Z)-6-(3-((tert-butyldimethylsilyl)oxy)-2-fluorophenyl)-8-(2-fluorobenzyl)-2-(furan-2-ylmethylene)imidazo[1,2-a]pyrazin-3(2H)-one (0.34 mmol) was reacted with sodium borohydride (0.064 g, 1.7 mmol) to afford the crude product as an orange solid. ESI MS m/z 548 [M+H]$^+$.

Step 5. 6-(2-fluoro-3-hydroxyphenyl)-8-(2-fluorobenzyl)-2-(furan-2-ylmethyl)imidazo[1,2-a]pyrazin-3(7H)-one (JRW-1668)

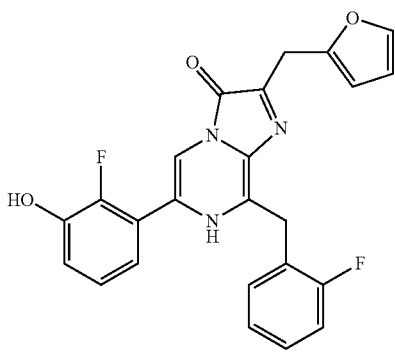 [SMILES: O=c1c(Cc2ccco2)nc2c(Cc3ccccc3F)[nH]c(-c3cccc(O)c3F)cn1-2]

Following general procedure G, 6-(3-(((tert-butyldimethylsilyl)oxy)-2-fluorophenyl)-8-(2-fluorobenzyl)-2-(furan-2-ylmethyl)imidazo[1,2-a]pyrazin-3(7H)-one (0.34 mmol) was reacted with HCl (1 mL, 6M) to afford the desired product (0.050 g, 34% over 4 steps). $^1$H NMR (400 MHz, Methanol-d4) δ 7.88 (s, 1H), 7.40 (d, J=2.0 Hz, 1H), 7.36-7.26 (m, 2H), 7.19-6.97 (m, 5H), 6.33 (dd, J=3.2, 1.9 Hz, 1H), 6.12 (dd, J=3.2, 1.0 Hz, 1H), 4.50 (s, 2H), 4.20 (s, 2H); ESI MS m/z 434 [M+H]$^+$.

Example 36. 6-(3-amino-2-fluorophenyl)-8-(2,6-difluorobenzyl)-2-(furan-2-ylmethyl)imidazo[1,2-a]pyrazin-3(7H)-one (JRW-1747)

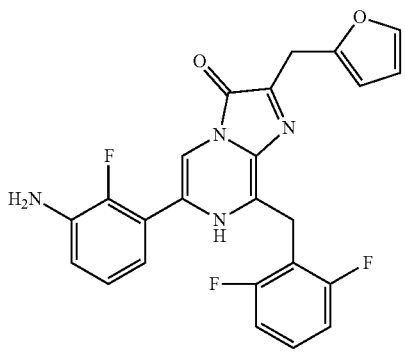 [SMILES: Nc1cccc(-c2cn3c(=O)c(Cc4ccco4)nc-3c(Cc3c(F)cccc3F)[nH]2)c1F]

Step 1. 5-bromo-3-(2,6-difluorobenzyl)pyrazin-2-amine (JRW-1727)

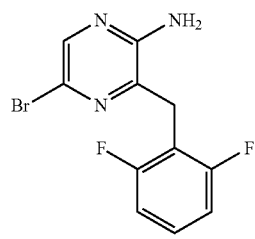

A suspension of zinc dust (9.5 g, 145 mmol) in HCl (20 mL, 1M) was stirred for 10 min. The solid was filtered, washed with methanol and THF, transferred to a flask, and dried under vacuum for 18 h. A solution of 2-(bromomethyl)-1,3-difluorobenzene (10.0 g, 48.3 mmol) in THF (50 mL) was added to the zinc dust. The mixture was heated to reflux for 2 h, then cooled, and allowed to settle. The supernatant was added to a solution of 3,5-dibromopyrazin-2-amine (5.6 g, 22.0 mmol) and bis(triphenylphosphine)palladium(II) dichloride (0.77 g, 1.1 mmol) in THF (50 mL). The suspension was heated to 50° C. for 18 h. The mixture was diluted with ethyl acetate and water, and the aqueous layer was extracted with ethyl acetate. The organic layers were combined, dried with sodium sulfate, filtered, concentrated, and purified with silica gel chromatography to obtain the desired product (4.2 g, 63%) as a light yellow solid. ESI MS m/z 301 [M+H]$^+$.

Step 2. Tert-butyl 2-((5-bromo-3-(2,6-difluorobenzyl)pyrazin-2-yl)amino)-2-(diethoxyphosphoryl)acetate (JRW-1730)

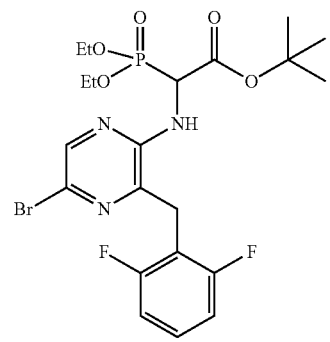 [SMILES: CCOP(=O)(OCC)C(Nc1ncc(Br)nc1Cc1c(F)cccc1F)C(=O)OC(C)(C)C]

Following general procedure A, 5-bromo-3-(2,6-difluorobenzyl)pyrazin-2-amine (1.0 g, 3.3 mmol) was reacted with tert-butyl 2-diazo-2-(diethoxyphosphoryl)acetate (1.4 g, 5.0 mmol) to afford the desired product as a brown solid. ESI MS m/z 551 [M+H]$^+$.

Step 3. Tert-butyl (Z)-2-((5-bromo-3-(2,6-difluorobenzyl)pyrazin-2-yl)amino)-3-(furan-2-yl)acrylate (JRW-1733)

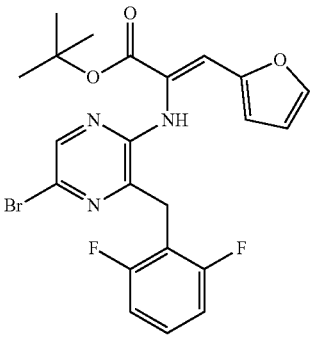 [SMILES: CC(C)(C)OC(=O)/C(=C/c1ccco1)Nc1ncc(Br)nc1Cc1c(F)cccc1F]

Following general procedure B, tert-butyl 2-((5-bromo-3-(2,6-difluorobenzyl)pyrazin-2-yl)amino)-2-(diethoxyphosphoryl)acetate (3.3 mmol) was reacted with furfural (0.38 g, 4.0 mmol) to afford the desired product (1.0 g, 65% over two steps) as a red foam. ESI MS m/z 493 [M+H]+.

Step 4. Tert-butyl (Z)-2-((3-(2,6-difluorobenzyl)-5-(2-fluoro-3-nitrophenyl)pyrazin-2-yl)amino)-3-(furan-2-yl)acrylate (JRW-1740)

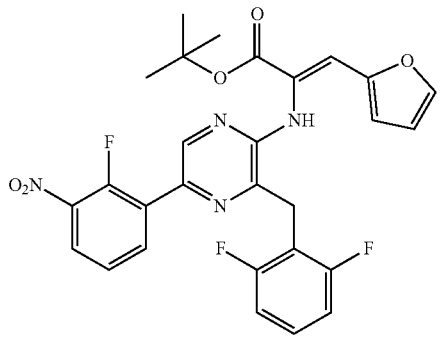 [SMILES: CC(C)(C)OC(=O)/C(=C/c1ccco1)Nc1ncc(-c2cccc([N+](=O)[O-])c2F)nc1Cc1c(F)cccc1F]

Following general procedure C, tert-butyl (Z)-2-((5-bromo-3-(2,6-difluorobenzyl)pyrazin-2-yl)amino)-3-(furan-2-yl)acrylate (0.21 g, 0.42 mmol) was reacted with 2-(2-fluoro-3-nitrophenyl)-4,4,5,5-tetramethyl-1,3,2-dioxaborolane (0.17 g, 0.64 mmol) to afford the desired product (0.087 g, 37%) as an orange oil. ESI MS m/z 553 [M+H]+.

Step 5. (Z)-2-((3-(2,6-difluorobenzyl)-5-(2-fluoro-3-nitrophenyl)pyrazin-2-yl)amino)-3-(furan-2-yl) acrylic acid (JRW-1742)

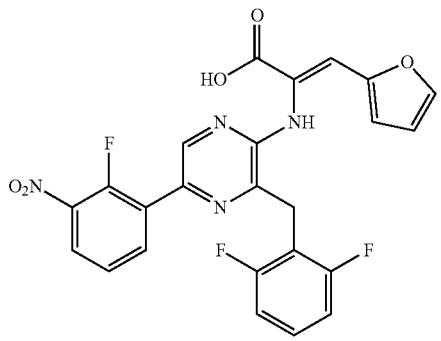 [SMILES: O=C(O)/C(=C/c1ccco1)Nc1ncc(-c2cccc([N+](=O)[O-])c2F)nc1Cc1c(F)cccc1F]

Following general procedure D, tert-butyl (Z)-2-((3-(2,6-difluorobenzyl)-5-(2-fluoro-3-nitrophenyl)pyrazin-2-yl) amino)-3-(furan-2-yl)acrylate (0.087 g, 0.16 mmol) was reacted with trifluoroacetic acid (1 mL) to afford the crude product. ESI MS m/z 497 [M+H]+.

Step 6. (Z)-8-(2,6-difluorobenzyl)-6-(2-fluoro-3-nitrophenyl)-2-(furan-2-ylmethylene)imidazo[1,2-a]pyrazin-3(2H)-one (JRW-1745)

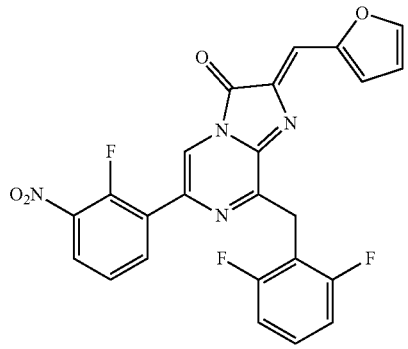 [SMILES: O=C1/C(=C/c2ccco2)N=C2C(Cc3c(F)cccc3F)=NC(c3cccc([N+](=O)[O-])c3F)=CN12]

Following general procedure E, (Z)-2-((3-(2,6-difluorobenzyl)-5-(2-fluoro-3-nitrophenyl)pyrazin-2-yl)amino)-3-(furan-2-yl)acrylic acid (0.16 mmol) was reacted with di(1H-imidazol-1-yl)methanone (0.051 g, 0.31 mmol) to afford the crude product as a red solid. ESI MS m/z 479 [M+H]+.

Step 7. 8-(2,6-difluorobenzyl)-6-(2-fluoro-3-nitrophenyl)-2-(furan-2-ylmethyl)imidazo[1,2-a]pyrazin-3(7H)-one (JRW-1746)

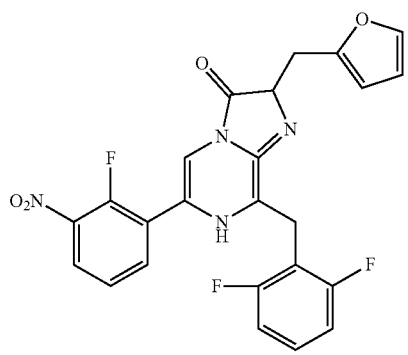

Following general procedure F, (Z)-8-(2,6-difluorobenzyl)-6-(2-fluoro-3-nitrophenyl)-2-(furan-2-ylmethylene) imidazo[1,2-a]pyrazin-3(2H)-one (0.16 mmol) was reacted with sodium borohydride (0.018 g, 0.47 mmol) to afford the crude product as a red solid. ESI MS m/z 481 [M+H]+.

Step 8. 6-(3-amino-2-fluorophenyl)-8-(2,6-difluorobenzyl)-2-(furan-2-ylmethyl)imidazo[1,2-a]pyrazin-3(7H)-one (JRW-1747)

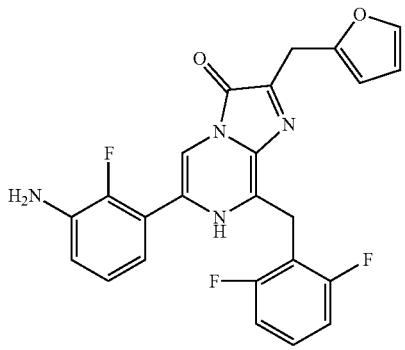 [SMILES: Nc1cccc(-c2cn3c(=O)c(Cc4ccco4)nc-3c(Cc3c(F)cccc3F)[nH]2)c1F]

Following general procedure H, 8-(2,6-difluorobenzyl)-6-(2-fluoro-3-nitrophenyl)-2-(furan-2-ylmethyl)imidazo[1,2-a]pyrazin-3(7H)-one (0.16 mmol) was reacted with hydrogen (1 atm) to obtain the desired product (0.014 g, 20% over 4 steps) as an orange solid. $^1$H NMR (400 MHz, Methanol-d4) δ 8.45-7.78 (m, 1H), 7.45-7.30 (m, 2H), 7.07-6.84 (m, 5H), 6.34 (t, J=2.6 Hz, 1H), 6.11 (d, J=3.2 Hz, 1H), 4.53 (s, 2H), 4.19 (s, 2H); ESI MS m/z 451 [M+H]$^+$.

Example 37. 8-(2,6-difluorobenzyl)-6-(2-fluoro-3-hydroxyphenyl)-2-(furan-2-ylmethyl)imidazo[1,2-a]pyrazin-3(7H)-one (JRW-1759)

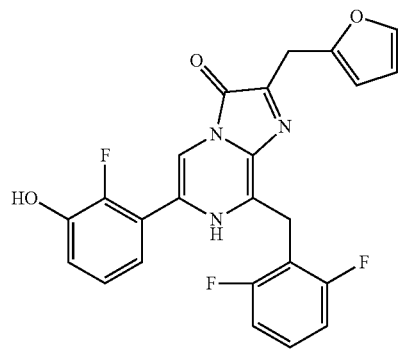 [SMILES: O=c1c(Cc2ccco2)nc2c(Cc3c(F)cccc3F)[nH]c(-c3cccc(O)c3F)cn1-2]

Step 1. Tert-butyl (Z)-2-((5-(3-((tert-butyldimethylsilyl)oxy)-2-fluorophenyl)-3-(2,6-difluorobenzyl)pyrazin-2-yl)amino)-3-(furan-2-yl)acrylate (JRW-1752)

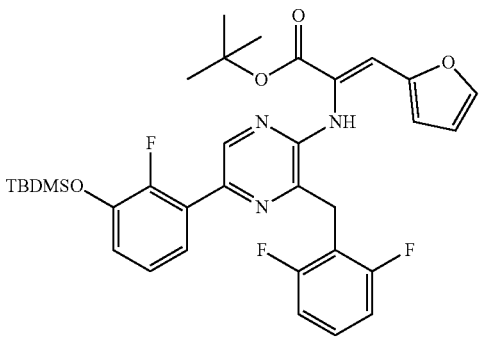 [SMILES: CC(C)(C)OC(=O)/C(=C/c1ccco1)Nc1ncc(-c2cccc(O[Si](C)(C)C(C)(C)C)c2F)nc1Cc1c(F)cccc1F]

Following general procedure C, tert-butyl (Z)-2-((5-bromo-3-(2,6-difluorobenzyl)pyrazin-2-yl)amino)-3-(furan-2-yl)acrylate (0.20 g, 0.41 mmol) was reacted with tert-butyl (2-fluoro-3-(4,4,5,5-tetramethyl-1,3,2-dioxaborolan-2-yl)phenoxy)dimethylsilane (0.21 g, 0.61 mmol) to afford the desired product (0.095 g, 36%) as a foam. ESI MS m/z 638 [M+H]$^+$.

Step 2. (Z)-2-((5-(3-((tert-butyldimethylsilyl)oxy)-2-fluorophenyl)-3-(2,6-difluorobenzyl)pyrazin-2-yl)amino)-3-(furan-2-yl)acrylic acid (JRW-1754)

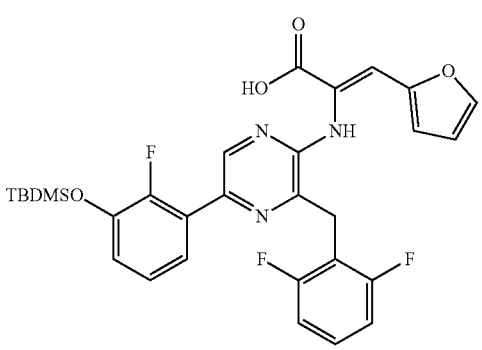 [SMILES: CC(C)(C)[Si](C)(C)Oc1cccc(-c2cnc(N/C(=C\c3ccco3)C(=O)O)c(Cc3c(F)cccc3F)n2)c1F]

Following general procedure D, tert-butyl (Z)-2-((5-(3-((tert-butyldimethylsilyl)oxy)-2-fluorophenyl)-3-(2,6-difluorobenzyl)pyrazin-2-yl)amino)-3-(furan-2-yl)acrylate (0.095 g, 0.15 mmol) was reacted with trifluoroacetic acid (1 mL) to afford the crude product as a red foam. ESI MS m/z 582 [M+H]$^+$.

Step 3. (Z)-6-(3-((tert-butyldimethylsilyl)oxy)-2-fluorophenyl)-8-(2,6-difluorobenzyl)-2-(furan-2-ylmethylene)imidazo[1,2-a]pyrazin-3(2H)-one (JRW-1757)

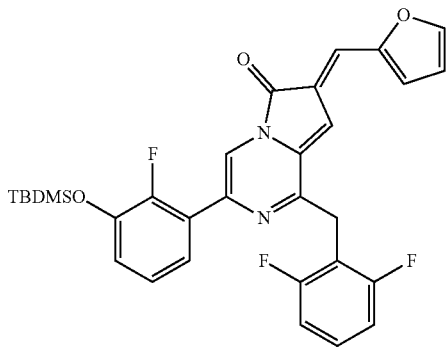 [SMILES: CC(C)(C)[Si](C)(C)Oc1cccc(C2=CN3C(=O)/C(=C/c4ccco4)C=C3C(Cc3c(F)cccc3F)=N2)c1F]

Following general procedure E, (Z)-2-((5-(3-((tert-butyldimethylsilyl)oxy)-2-fluorophenyl)-3-(2,6-difluorobenzyl)pyrazin-2-yl)amino)-3-(furan-2-yl)acrylic acid (0.15 mmol) was reacted with di(1H-imidazol-1-yl)methanone (0.048 g, 0.30 mmol) to afford the crude product as a red solid. ESI MS m/z 564 [M+H]$^+$.

Step 4. 6-(3-((tert-butyldimethylsilyl)oxy)-2-fluorophenyl)-8-(2,6-difluorobenzyl)-2-(furan-2-ylmethyl)imidazo[1,2-a]pyrazin-3(7H)-one (JRW-1758)

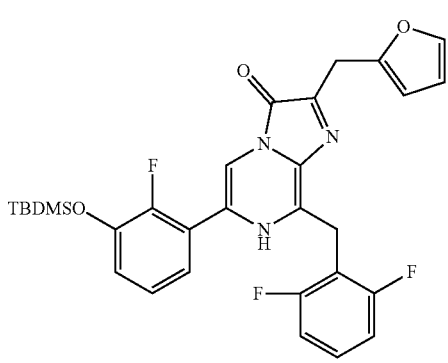 [SMILES: CC(C)(C)[Si](C)(C)Oc1cccc(-c2cn3c(=O)c(Cc4ccco4)nc-3c(Cc3c(F)cccc3F)[nH]2)c1F]

Following general procedure F, (Z)-6-(3-((tert-butyldimethylsilyl)oxy)-2-fluorophenyl)-8-(2,6-difluorobenzyl)-2-(furan-2-ylmethylene)imidazo[1,2-a]pyrazin-3(2H)-one (0.15 mmol) was reacted with sodium borohydride (0.017 g, 0.44 mmol) to afford the crude product as an orange solid. ESI MS m/z 566 [M+H]$^+$.

Step 5. 8-(2,6-difluorobenzyl)-6-(2-fluoro-3-hydroxyphenyl)-2-(furan-2-ylmethyl)imidazo[1,2-a]pyrazin-3(7H)-one (JRW-1759)

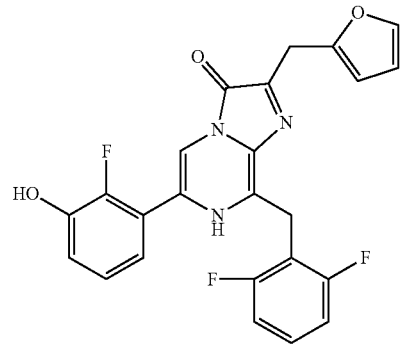 [SMILES: O=c1c(Cc2ccco2)nc2c(Cc3c(F)cccc3F)[nH]c(-c3cccc(O)c3F)cn1-2]

Following general procedure G, 6-(3-((tert-butyldimethylsilyl)oxy)-2-fluorophenyl)-8-(2,6-difluorobenzyl)-2-(furan-2-ylmethyl)imidazo[1,2-a]pyrazin-3(7H)-one (0.15 mmol) was reacted with HCl (1 mL, 6M) to afford the desired product (0.030 g, 45% over 4 steps). $^1$H NMR (400 MHz, Methanol-d4) δ 8.21 (s, 1H), 7.44-7.31 (m, 2H), 7.23-7.11 (m, 1H), 7.07-6.93 (m, 4H), 6.34 (t, J=2.5 Hz, 1H), 6.11 (d, J=3.2 Hz, 1H), 4.54 (s, 2H), 4.20 (s, 2H); ESI MS m/z 434 [M+H]$^+$.

Example 38. Luminescent Properties

Luminescence Assay Procedure:

Each compound to be screened was dissolved in DMSO (5 mM) and then further diluted to 100 μM in NANO-GEO® Luciferase Assay Buffer. A two-fold dilution series was prepared for each substrate by serially diluting 500 μl of the substrate solution with 500 μl of NANO-GLO® Luciferase Assay Buffer. Each diluted substrate titration was then combined in equal volumes with purified NANOLUC® Luciferase diluted into $CO_2$ independent media+10% FBS. Initial light output for each substrate was measured in a GLOMAX®-Multi+ luminometer three minutes after substrate addition and then at five minute intervals as a means to determine signal half-life. Signal half-life was calculated using GraphPad Prism One Phase Decay regression and Km and Vmax were calculated using GraphPad Prism using Michaelis-Menten regression.

The synthesized coelenterazine analogues (compounds of formula (I) and (II)) were evaluated for their suitability as luciferase substrates. NANOLUC® luciferase was employed for the screening because it is a small (19 kDa), stable, and particularly bright enzyme. Table 1 demonstrates that the synthesized compounds possess relative light unit (RLUs) and half-life data that is comparable to a known coelenterazine analogue, 8-benzyl-2-(furan-2-ylmethyl)-6-phenylimidazo[1,2-a]pyrazin-3(7H)-one (furimazine), which is known to be superior to coelenterazine as a luciferase substrate. RLU, half-life, and Km values are for furimazine is set to 1.0.

TABLE 1

Summary of RLU, half-life and kinetic data for the coelenterazine analogues.

| Compound | RLU (@100 μM) | Half-life @100 μM | Km |
|---|---|---|---|
| Furimazine | 1 | 1 | 1 |
| JRW-0372 | 0.00033 | NA | 8.5 |
| JRW-0373 | 0.27 | 2 | 2 |
| JRW-0777 | 0.45 | 1 | 4.3 |
| JRW-0786 | 0.88 | 0.5 | 2.7 |
| JRW-0805 | 0.17 | 1 | 3.6 |
| JRW-1040 | 0.8 | 0.4 | 2.3 |
| JRW-1043 | 0.8 | 0.6 | 2.7 |
| JRW-1047 | 0.5 | 1.2 | 3.2 |
| JRW-1052 | 0.4 | 0.8 | 2.7 |
| JRW-1056 | 1.1 | 0.3 | 2.5 |
| JRW-1180 | 0.42 | 0.1 | 1.1 |
| JRW-1368 | 0.032 | 2.8 | 1.1 |
| JRW-1370 | 0.036 | 2.5 | 1.5 |
| JRW-1404 | 1.2 | 1.1 | 1 |
| JRW-1405 | 1.0 | 1.1 | 1 |
| JRW-1411 | 0.001 | 6.6 | 3.6 |
| JRW-1424 | 0.14 | 3.3 | 4.6 |
| JRW-1479 | 0.43 | 2.3 | 6.7 |
| JRW-1482 | 1.7 | 0.8 | 1 |
| JRW-1483 | 0.008 | 4 | 3 |
| JRW-1488 | 0.31 | 1.5 | 1.5 |
| JRW-1498 | 0.049 | 3.4 | 1.3 |
| JRW-1525 | 0.4 | 1.4 | 1.2 |
| JRW-1526 | 1.0 | 1.5 | 2.2 |
| JRW-1535 | 0.73 | 3.5 | 2.6 |
| JRW-1536 | 0.08 | 2.0 | 3.2 |
| JRW-1609 | 0.44 | 1.7 | 1.7 |
| JRW-1610 | 0.71 | 1.3 | 2.6 |
| JRW-1619 | 0.85 | 1.0 | 2.7 |
| JRW-1624 | 0.84 | 1.7 | 1.4 |
| JRW-1634 | 1.0 | 0.77 | 2.7 |
| JRW-1635 | 1.0 | 0.89 | 1.6 |
| JRW-1642 | 0.04 | 3.5 | 4.1 |
| JRW-1645 | 0.07 | 4.7 | 1.8 |
| JRW-1667 | 2.1 | 0.52 | 1.3 |
| JRW-1668 | 1.5 | 0.75 | 2.0 |
| JRW-1747 | 2.1 | 0.3 | 2.8 |
| JRW-1759 | 1.0 | 0.6 | 3.3 |

Example 39. Half-Life Improvements

Signal decay was compared for compounds having a hydroxyl at either the para or meta position of the 6-position phenyl of the coelenterazine core. Moving the hydroxyl group (or amino group, etc.) from the para to the meta-position resulted in more than a 10-fold increase in signal kinetics, thereby enabling these substrates for broader uses. The structures and half-life values for representative examples are compared below, relative to furimazine, set to 1.

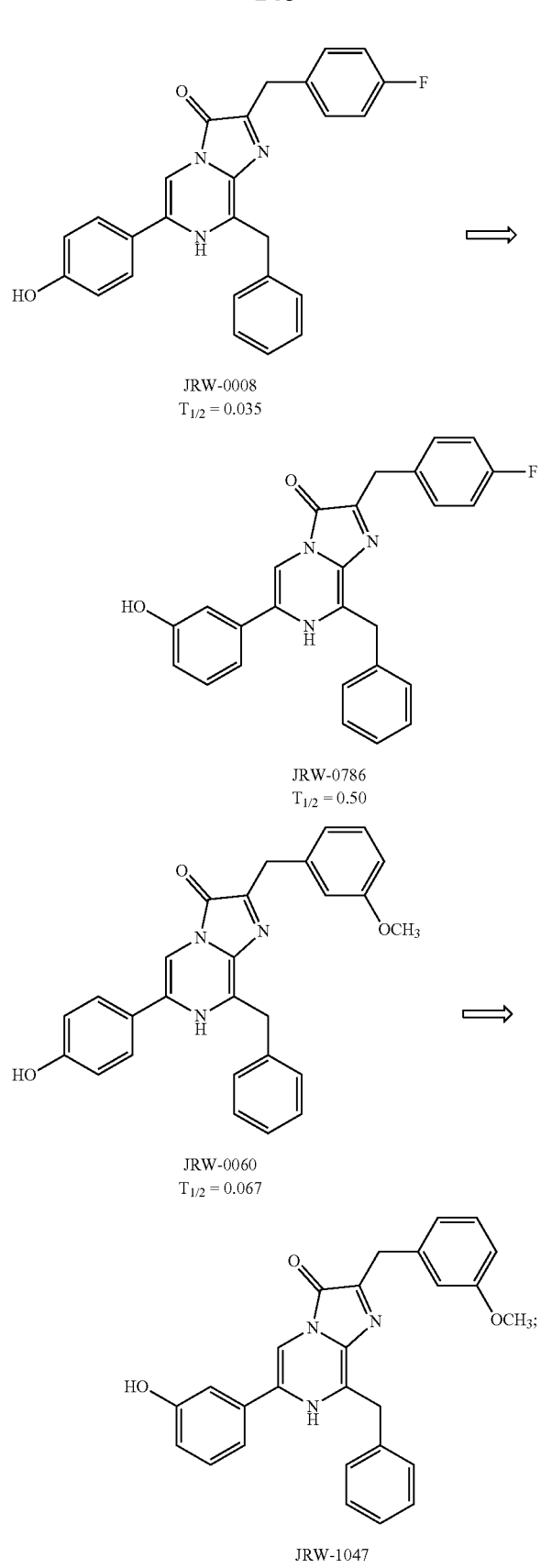

JRW-0008
$T_{1/2} = 0.035$

JRW-0786
$T_{1/2} = 0.50$

JRW-0060
$T_{1/2} = 0.067$

JRW-1047
$T_{1/2} = 1.2$

149
-continued

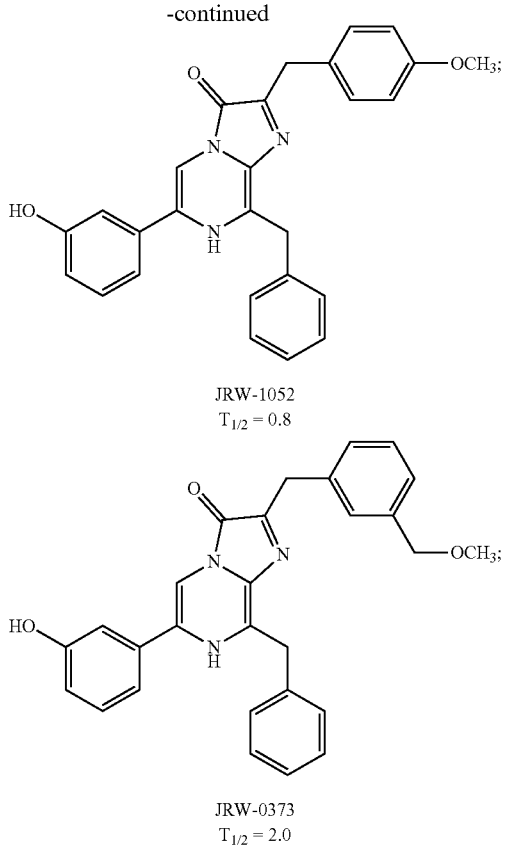

JRW-1052
$T_{1/2} = 0.8$

JRW-0373
$T_{1/2} = 2.0$

Example 40. Solubility Testing

To assess solubility, test compounds were dissolved in a mixture of ethanol/propylene glycol (1:1) at 43 mM. This 5× stock solution was then added to a solution of hydroxypropyl-β-cyclodextrin/water/PEG400 to give a formulation mixture of 8.7 mM in ethanol/propylene glycol/hydroxypropyl-β-cyclodextrin/PEG 400/water (10:10:10:35:35). The mixture was vortexed and centrifuged. Supernatant was sampled and measured in a UV-Vis spectrometer. The mixture was filtered through a 0.2 micron syringe filter and the filtrate was measured and compared to the supernatant.

Figure 2:
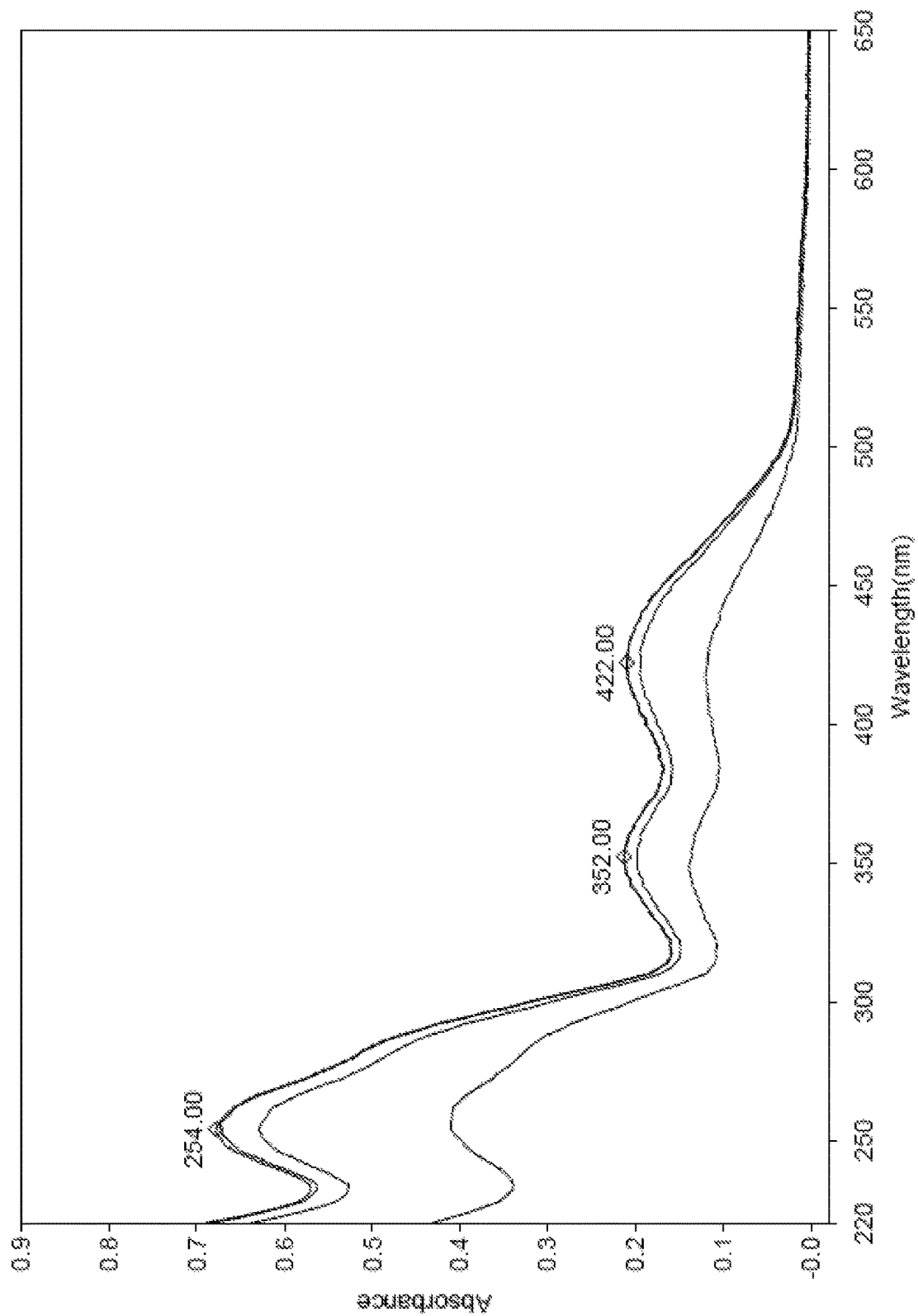
FIG. 2 shows UV absorbance spectra for 8.7 mM furimazine in ethanol/propylene glycol/hydroxypropyl-β-cyclodextrin/PEG 400/water (10:10:10:35:35) before (supernatant) and after filtration (filtrate).

Shown in FIG. 1 are UV spectra of JRW-1040 in the formulation, comparing supernatant and filtrate. The two UV spectra are superimposed, showing JRW-1040 is fully soluble in the formulation. Shown in FIG. 2 is the same experiment with furimazine. The differences in the spectra show furimazine is not fully soluble in the formulation. This is an example showing improvements in solubility compared to furimazine.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

150
What is claimed is:
1. A compound of formula (II)

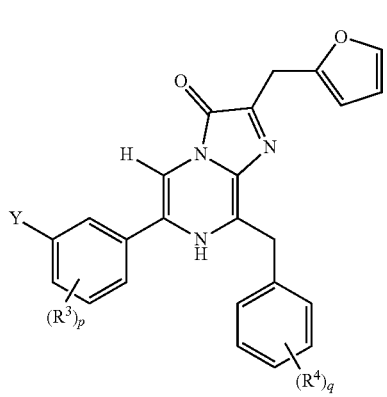

(II)

or a tautomer or a salt thereof, wherein:
Y is nitro, or —$NR^{y1}R^{y2}$;
p is 0, 1, 2, 3, or 4;
q is 0, 1, 2, 3, 4, or 5;
p+q is 1, 2, 3, 4, 5, 6, 7, 8, or 9;
$R^3$, at each occurrence, is independently halogen, CN, nitro, $C_{1-10}$alkyl, $C_{1-10}$haloalkyl, —$OR^{A3}$, or —$NR^{B3}R^{C3}$;
$R^4$, at each occurrence, is independently halogen, CN, nitro, $C_{1-10}$alkyl, $C_{1-10}$haloalkyl, —$OR^{A4}$, or —$NR^{B4}R^{C4}$;
$R^{A3}$ and $R^{A4}$, at each occurrence, are independently H, $C_{1-10}$haloalkyl, $C_{3-12}$cycloalkyl, —$C(O)C_{1-10}$alkyl, —$C(O)C_{3-12}$cycloalkyl, or —$C(O)C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;
$R^{B3}$, $R^{B4}$, $R^{C3}$, and $R^{C4}$, at each occurrence, are independently H, $C_{1-10}$haloalkyl, $C_{3-12}$cycloalkyl, —$C(O)C_{1-10}$alkyl, —$C(O)C_{3-12}$cycloalkyl, —$C(O)C_{1-3}$alkylene-$C_{3-12}$cycloalkyl, —$SO_2C_{1-10}$alkyl, —$SO_2C_{3-12}$cycloalkyl, or —$SO_2C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl;
alternatively, $R^{B3}$ and $R^{C3}$ and/or $R^{B4}$ and $R^{C4}$, together with the nitrogen atom to which each attaches form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl;
$R^{y1}$ and $R^{y2}$, at each occurrence, are independently H, $C_{1-10}$alkyl, $C_{1-10}$haloalkyl, $C_{3-12}$cycloalkyl, or —$C_{1-3}$alkylene-$C_{3-12}$cycloalkyl, wherein each cycloalkyl is optionally substituted with 1-4 substituents independently selected from the group consisting of halogen, $C_{1-4}$alkyl, and $C_{1-4}$haloalkyl; and
alternatively, $R^{y1}$ and $R^{y2}$ together with the nitrogen atom to which each attaches form a 4- to 8-membered saturated or partially unsaturated heterocyclic ring, optionally substituted with 1-4 substituents independently selected from the group consisting of $C_{1-4}$alkyl, $C_{1-4}$haloalkyl, oxo, —OH, and —$OC_{1-4}$alkyl.

2. The compound of claim 1, or a tautomer or a salt thereof, wherein q is 0, 1, or 2.

3. The compound of claim 1, or a tautomer or a salt thereof, wherein $R^{y1}$ and $R^{y2}$ are H.

4. The compound of claim 1, or a tautomer or a salt thereof, wherein p+q is 1 or 2.

5. The compound of claim 1, or a tautomer or a salt thereof, wherein p is 1 and $R^3$ is halogen.

6. The compound of claim 5, or a tautomer or salt thereof, wherein $R^3$ is fluorine.

7. The compound of claim 1, or a tautomer or salt thereof, wherein $R^4$, at each occurrence, is halogen.

8. The compound of claim 7, or a tautomer or a salt thereof, wherein the halogen is fluorine.

9. The compound of claim 1, or a tautomer or salt thereof, wherein q is 1 or 2 and $R^4$ is fluorine.

10. The compound of claim 1, or a tautomer or a salt thereof, wherein q is 1 and $R^4$ is $C_{1-10}$alkyl.

11. The compound of claim 1, or a tautomer or salt thereof, selected from the group consisting of:

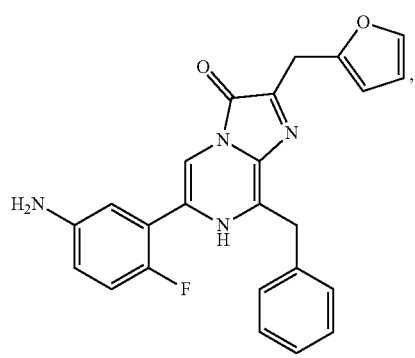

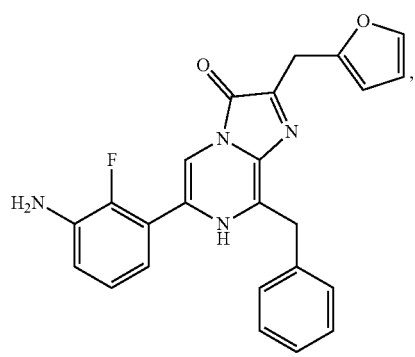

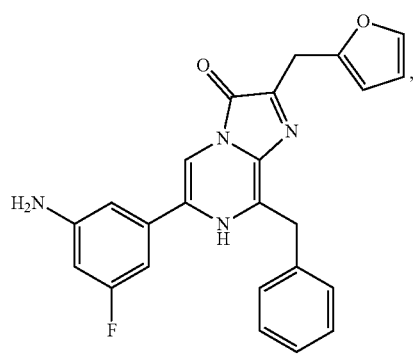

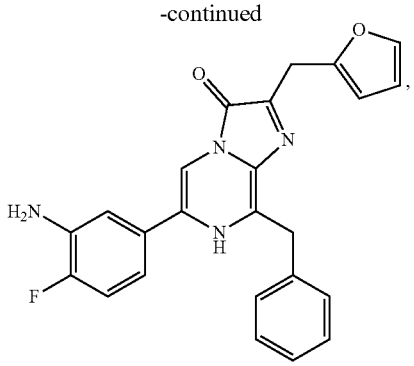

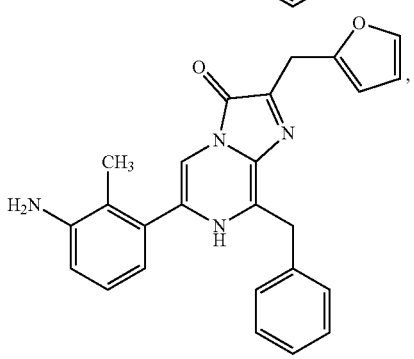

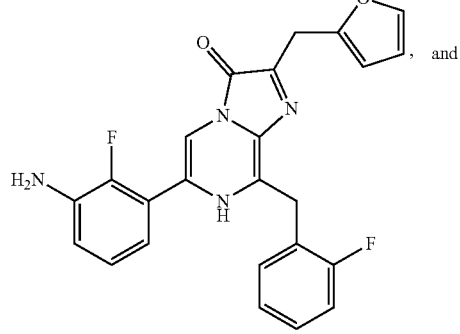

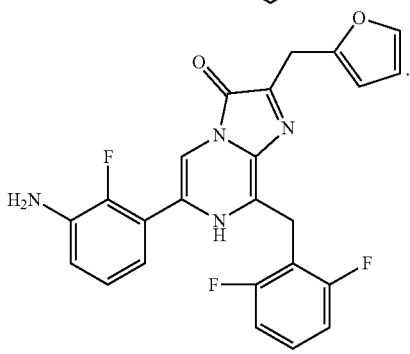

12. A kit comprising the compound of claim 1, or a tautomer or a salt thereof.

13. A method for detecting luminescence in a sample, the method comprising
    contacting a sample with the compound of claim 1, or a tautomer or a salt thereof;
    contacting the sample with a coelenterazine-utilizing luciferase, if it is not present in the sample; and
    detecting luminescence.

14. A method for detecting luminescence in a transgenic animal comprising
    administering the compound of claim 1, or a tautomer or a salt thereof, to a transgenic animal; and detecting luminescence;
wherein the transgenic animal expresses a coelenterazine-utilizing luciferase.

15. The compound of claim 1, or a tautomer or a salt thereof, wherein:
Y is nitro, or NR$^{y1}$R$^{y2}$;
p is 0, 1, or 2;
q is 0, 1, or 2;
p+q is 1 or 2;
R$^3$, at each occurrence, is independently halogen or C$_{1-4}$alkyl; and
R$^4$, at each occurrence, is independently halogen or C$_{1-4}$alkyl.

16. The compound of claim 15, or a tautomer or a salt thereof, wherein:
p is 0 or 1;
Y is NR$^{y1}$R$^{y2}$;
R$^{y1}$ and R$^{y2}$ are H;
R$^3$, at each occurrence, is independently fluorine or methyl; and
R$^4$, at each occurrence, is independently fluorine or methyl.

17. A compound of formula:

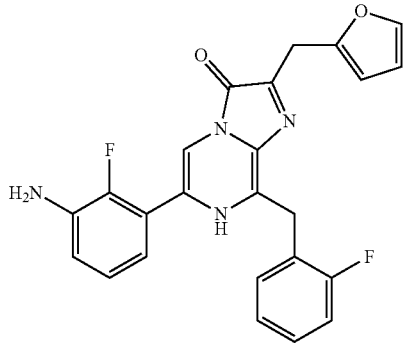 [SMILES: Nc1cccc(-c2cn3c(=O)c(Cc4ccco4)nc-3c(Cc3ccccc3F)[nH]2)c1F]

or a tautomer or salt thereof.

* * * * *